United States Patent
Ho et al.

(10) Patent No.: US 10,308,707 B2
(45) Date of Patent: Jun. 4, 2019

(54) BISPECIFIC HIV-1-NEUTRALIZING ANTIBODIES

(71) Applicant: Aaron Diamond AIDS Research Center, New York, NY (US)

(72) Inventors: David D. Ho, Chappaqua, NY (US); Yaoxing Huang, Brooklyn, NY (US); Jian Yu, New Providence, NJ (US)

(73) Assignee: AARON DIAMOND AIDS RESEARCH CENTER, New York, NY (US)

( * ) Notice: Subject to any disclaimer, the term of this patent is extended or adjusted under 35 U.S.C. 154(b) by 0 days.

(21) Appl. No.: 15/850,832

(22) Filed: Dec. 21, 2017

(65) Prior Publication Data
US 2018/0237505 A1 Aug. 23, 2018

Related U.S. Application Data

(60) Continuation-in-part of application No. 15/414,822, filed on Jan. 25, 2017, now Pat. No. 9,884,905, which is a division of application No. 14/558,341, filed on Dec. 2, 2014, now Pat. No. 9,587,012.

(60) Provisional application No. 61/910,685, filed on Dec. 2, 2013.

(51) Int. Cl.
| *C07K 16/10* | (2006.01) |
| *C07K 16/28* | (2006.01) |
| *A61P 31/18* | (2006.01) |
| *A61K 39/42* | (2006.01) |
| *A61K 39/00* | (2006.01) |

(52) U.S. Cl.
CPC .......... *C07K 16/1063* (2013.01); *A61K 39/42* (2013.01); *A61P 31/18* (2018.01); *C07K 16/2812* (2013.01); *C07K 16/2866* (2013.01); *A61K 2039/505* (2013.01); *C07K 2317/24* (2013.01); *C07K 2317/31* (2013.01); *C07K 2317/52* (2013.01); *C07K 2317/567* (2013.01); *C07K 2317/66* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| 7,122,185 | B2 | 10/2006 | Olson et al. |
| 8,333,971 | B2 | 12/2012 | Goldenberg et al. |
| 8,637,024 | B2 | 1/2014 | Ho et al. |
| 2012/0121597 | A1 | 5/2012 | Ho et al. |

FOREIGN PATENT DOCUMENTS

| EP | 2246364 | 11/2010 |
| WO | 2012065055 | 5/2012 |
| WO | 2013163427 | 10/2013 |
| WO | 2014100139 | 6/2014 |

OTHER PUBLICATIONS

Burkly et al., "Inhibition of HIV Infection by a Novel CD4 Domain 2-Specific Monoclonal Antibody," The Journal of Immunology, vol. 149, pp. 1779-1787, No. 5, Sep. 1, 1992.
Fendly et al., "Characterization of Murine Monoclonal Antibodies Reactive to Either the Human Epidermal Growth Factor Receptor or HER2/neu Gene Product," Cancer Research 50, pp. 1550-1558, Mar. 1, 1990.
Huang et al., "Broad and potent neutralization of HIV-1 by a gp41-specific human antibody," Nature, vol. 491, pp. 406-414, Nov. 15, 2012.
Moore et al., "A Monoclonal Antibody to CD4 Domain 2 Blocks Soluble CD4-Induced Conformational Changes in the Envelope Glycoproteins of Human Immunodeficiency Virus Type 1 (HIV-1) and HIV-1 Infection of CD4+ Cells," Journal of Virology, vol. 66, No. 8, pp. 4784-4793, Aug. 1992.
Olson et al., "Differential Inhibition of Human Immunodeficiency Virus Type 1 Fusion, gp120 Binding, and CC-Chemokine Activity by Monoclonal Antibodies to CCR5," Journal of Virology, vol. 73, No. 5, pp. 4145-4155, May 1999.
Reimann et al., "A Humanized Form of a CD4-Specific Monoclonal Antibody Exhibits Decreased Antigenicity and Prolonged Plasma Half-Life in Rhesus Monkeys While Retaining Its Unique Biological and Antiviral Properties," Aids Research and Human Retroviruses, vol. 13, No. 11, pp. 933-943, 1997.
Rudicell et al., "Bispecific antibodies targeting different epitopes on the HIV-1 envelope exhibit broad and potent neutralization," Journal of Virology Accepted Manuscript Posted Online, doi:10.1128/JVI.02097-15, pp. 1-32, Oct. 7, 2015.
Schaefer et al., "Immunoglobulin domain crossover as a generic approach for the production of bispecific IgG antibodies," Proceedings of the National Academy of Sciences, vol. 108, No. 27, pp. 11187-11192, Jul. 5, 2011.
Scheid et al., "Sequence and Structural Convergence of Broad and Potent HIV Antibodies That Mimic CD4 Binding," Science, vol. 333, pp. 1633-1637, Sep. 16, 2011.
Trkola et al., "Potent, Broad-Spectrum Inhibition of Human Immunodeficiency Virus Type 1 by the CCR5 Monoclonal Antibody PRO 140," Journal of Virology, vol. 75, No. 2, pp. 579-588, Jan. 2001.
Walker et al., "Broad neutralization coverage of HIV by multiple highly potent antibodies," Nature, vol. 477, pp. 466-470, Sep. 22, 2011.
International Search Report and Written Opinion, International Appln. No. PCT/US14/68183, dated Apr. 16, 2015, 11 pages.
Markowitz, "Setting the Stage: Long-acting agents for PrEP," Aaron Diamond AIDS Research Center, Rockefeller University, <URL: http://www.adarc.org/files/May_6_2013_Presentations/Markowitz.pdf>; pp. 1-36, May 6, 2013.
Pace et al., "Bispecific antibodies directed to CD4 domain 2 and HIV envelope exhibit exceptional breadth and picomolar potency against HIV-1," Proceedings of the National Academy of Sciences, vol. 110, No. 33, pp. 13540-13545, Aug. 13, 2013.

(Continued)

*Primary Examiner* — Nicole Kinsey White
(74) *Attorney, Agent, or Firm* — Morgan, Lewis & Bockius LLP

(57) ABSTRACT

In various embodiments, the present invention relates generally to using bispecific antibodies in the prevention and treatment of HIV.

5 Claims, 49 Drawing Sheets
Specification includes a Sequence Listing.

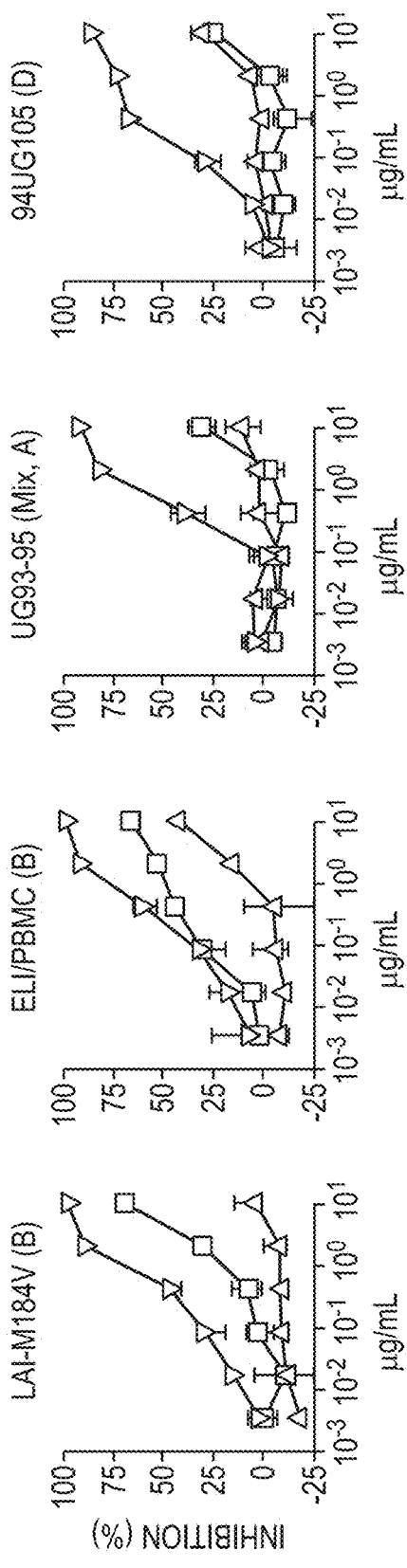
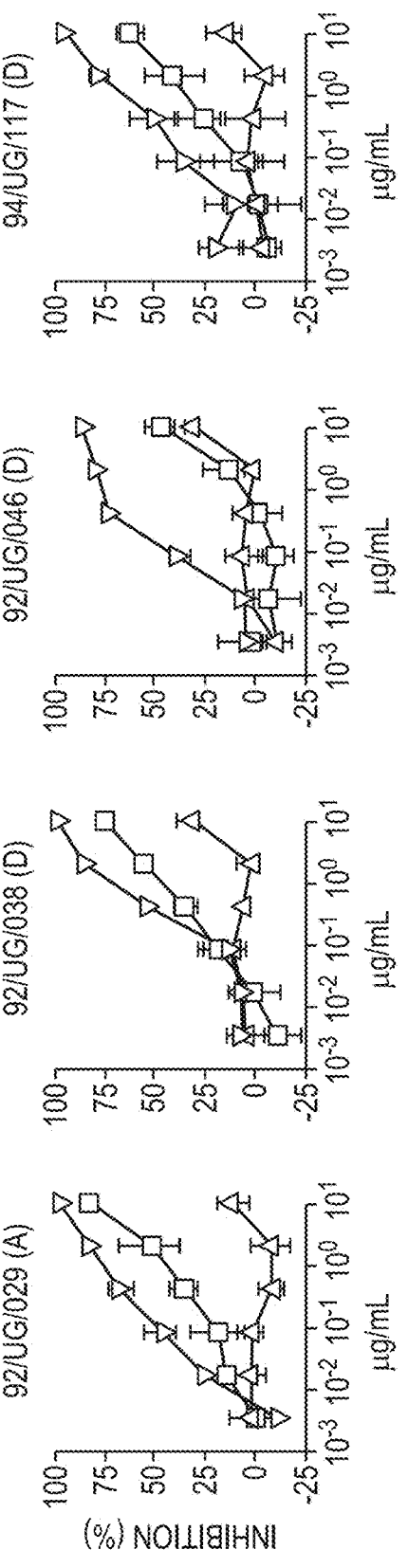

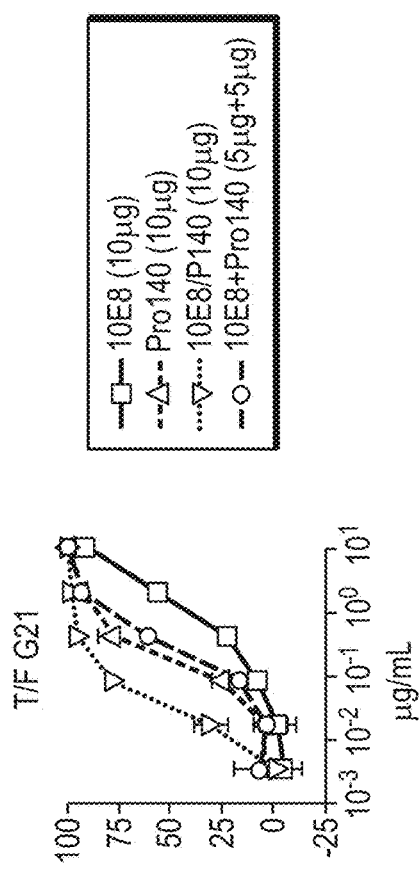
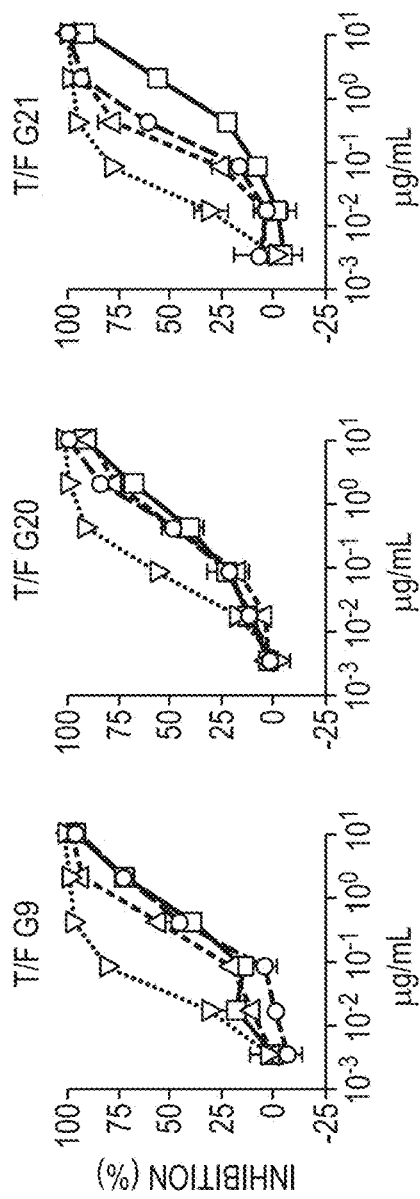
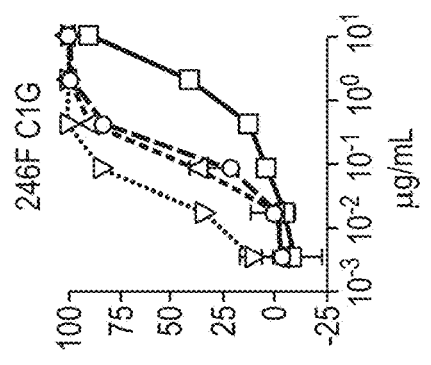
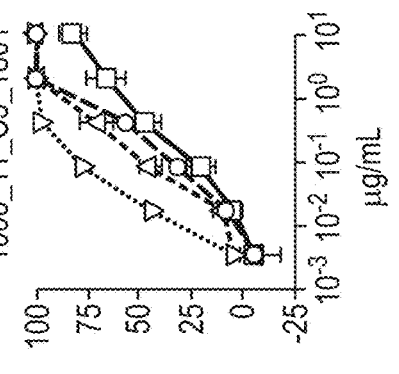
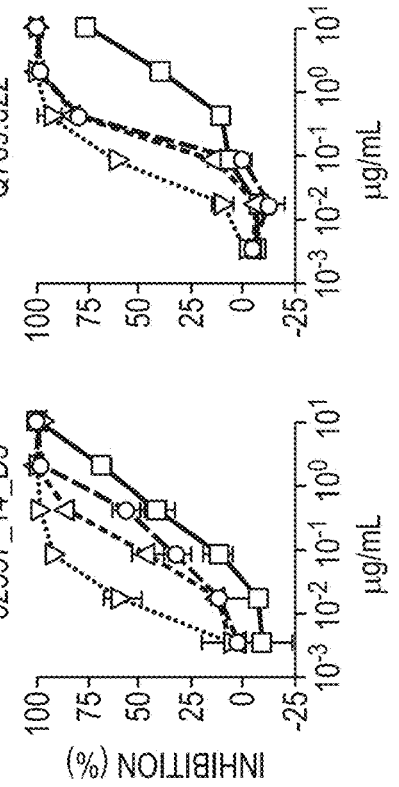

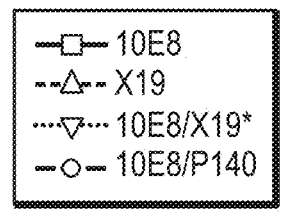
*NON-MEMBRANE BOUND Ab

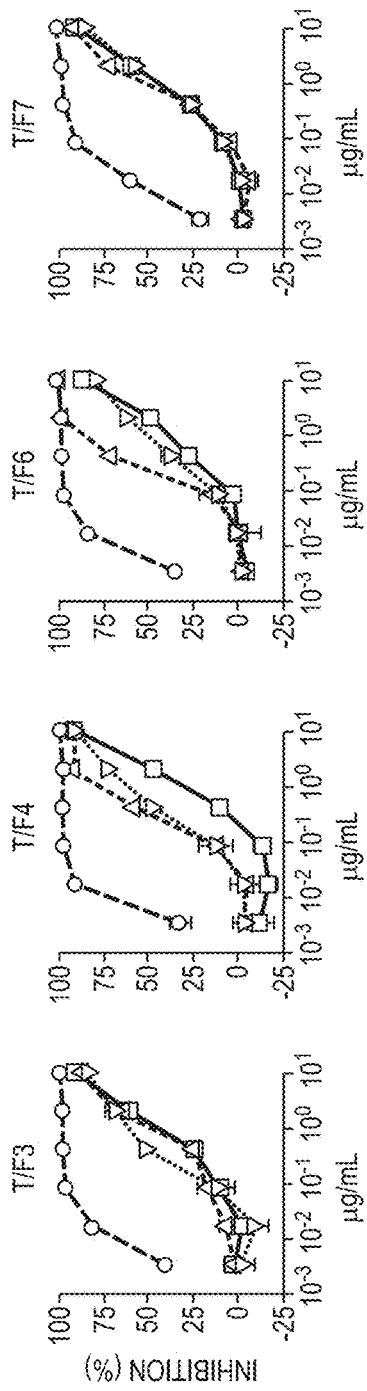

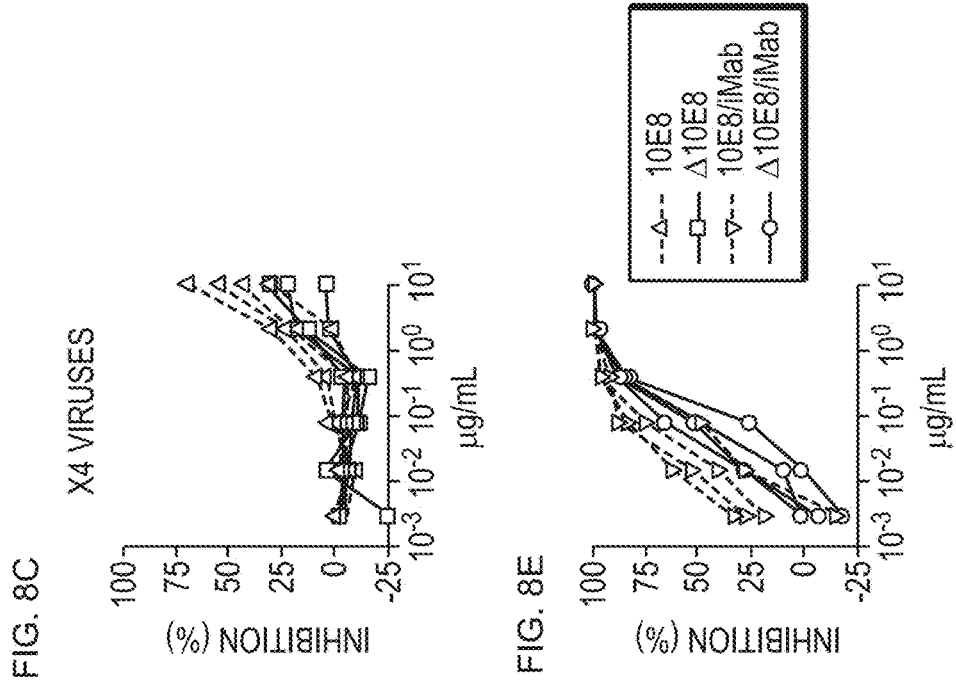
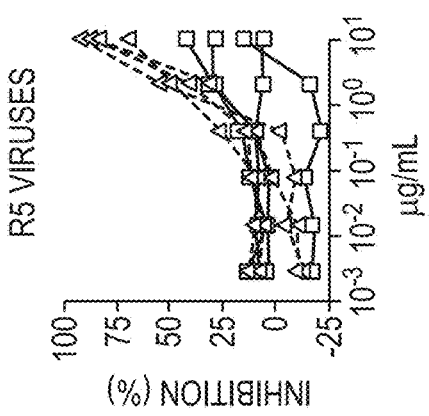
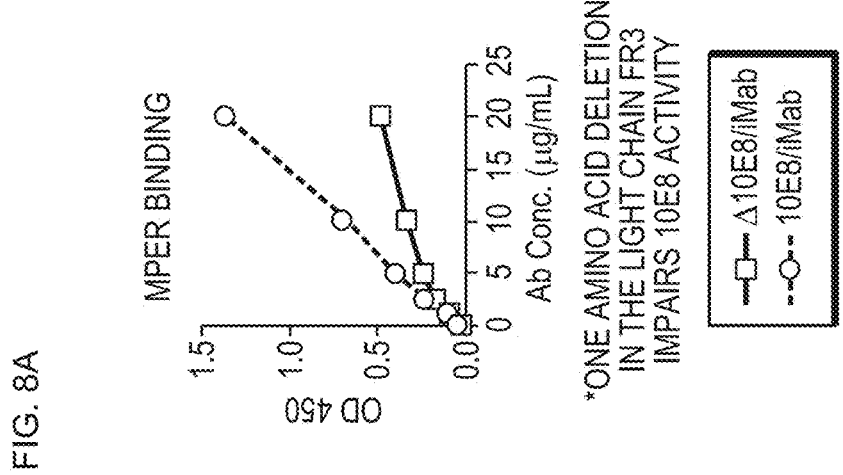

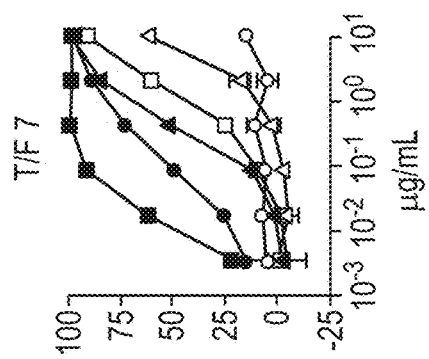
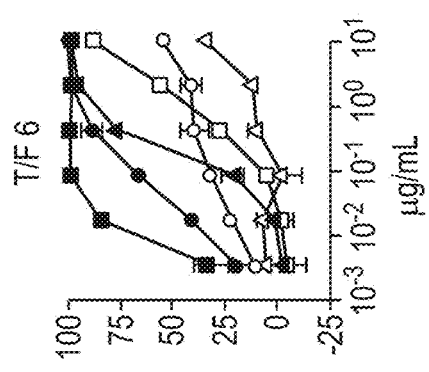
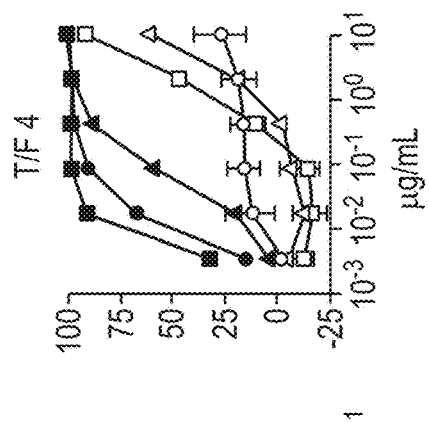
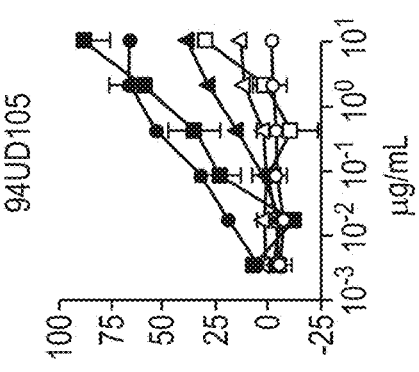
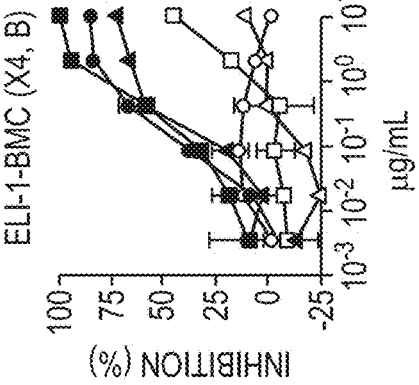

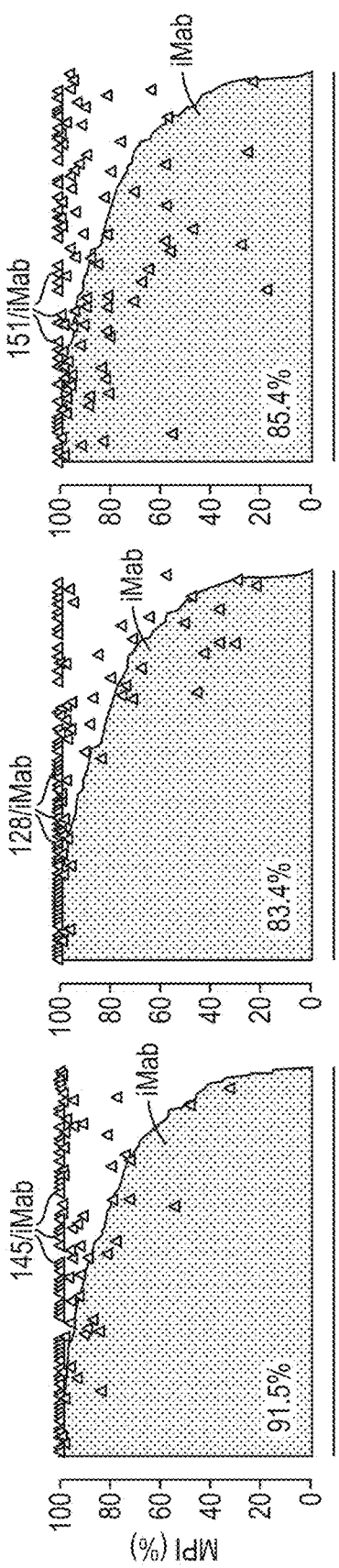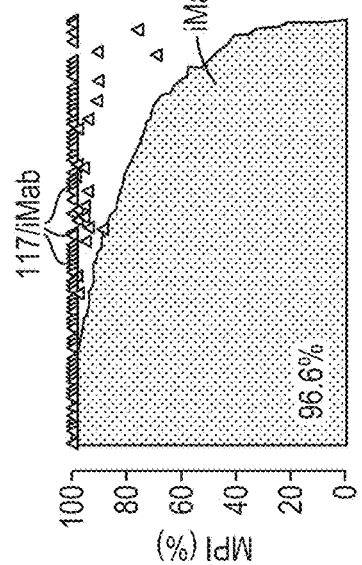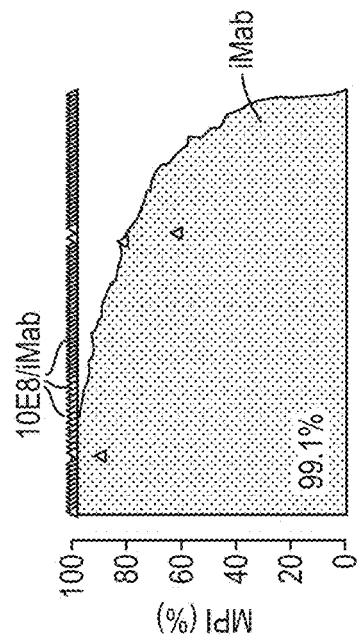

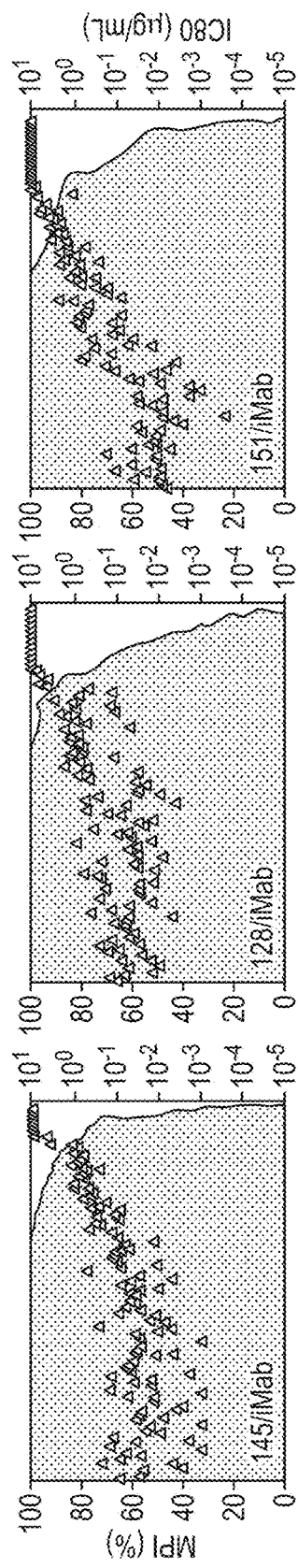
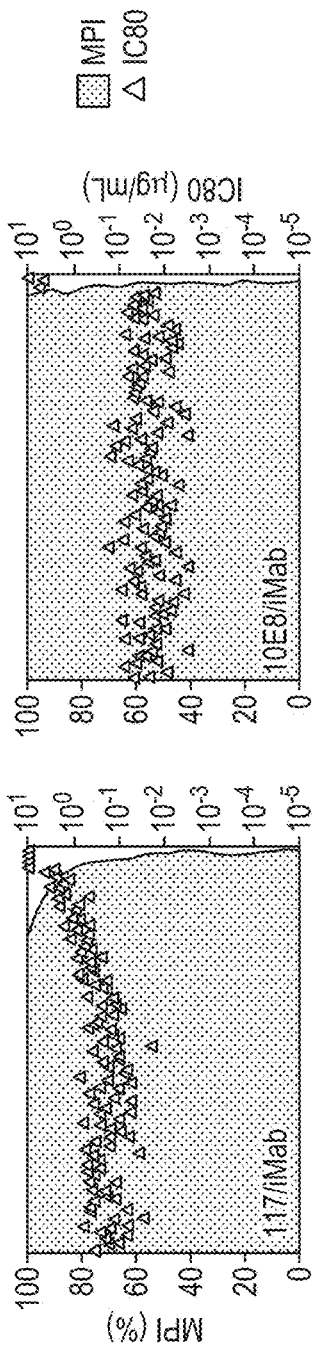
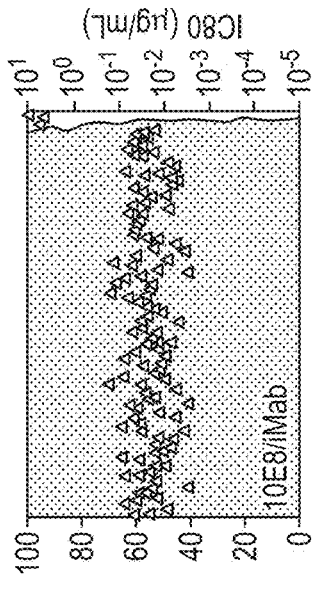
FIG. 12A  FIG. 12B  FIG. 12C  FIG. 12D  FIG. 12E

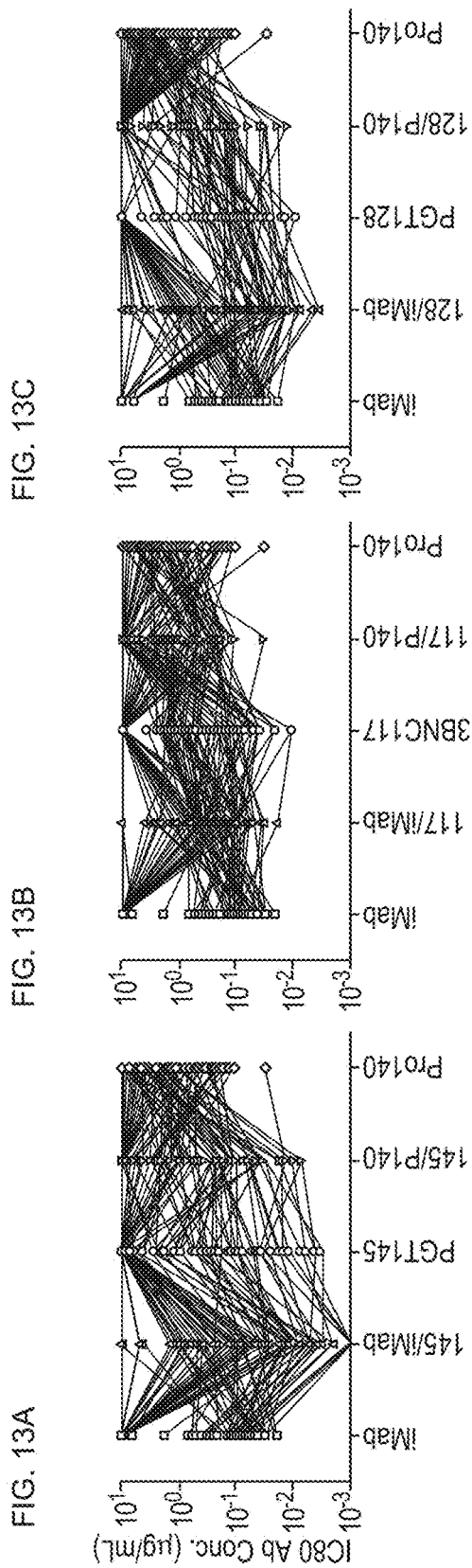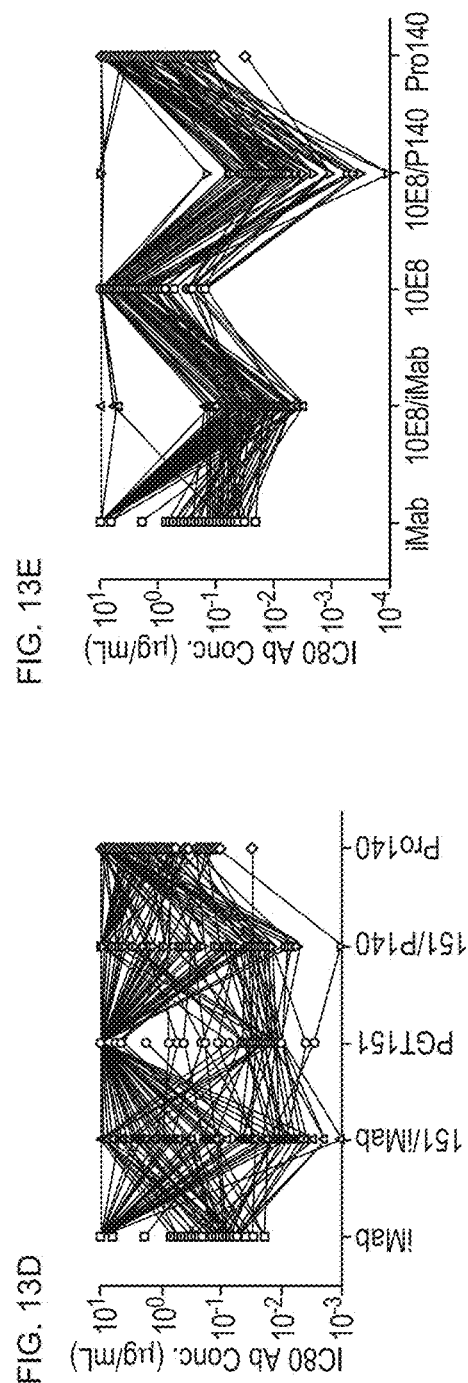
FIG. 13A
FIG. 13B
FIG. 13C
FIG. 13D
FIG. 13E

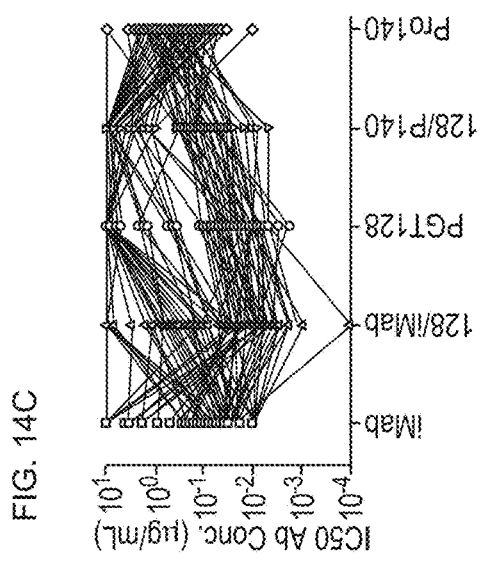
FIG. 14A  FIG. 14B  FIG. 14C
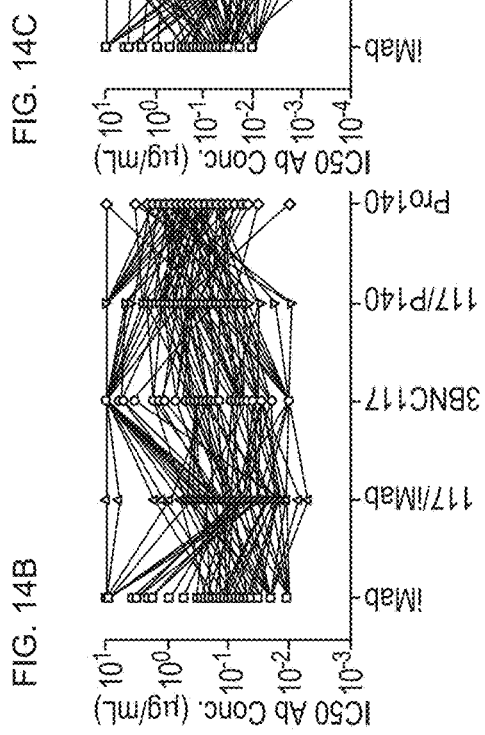
FIG. 14D
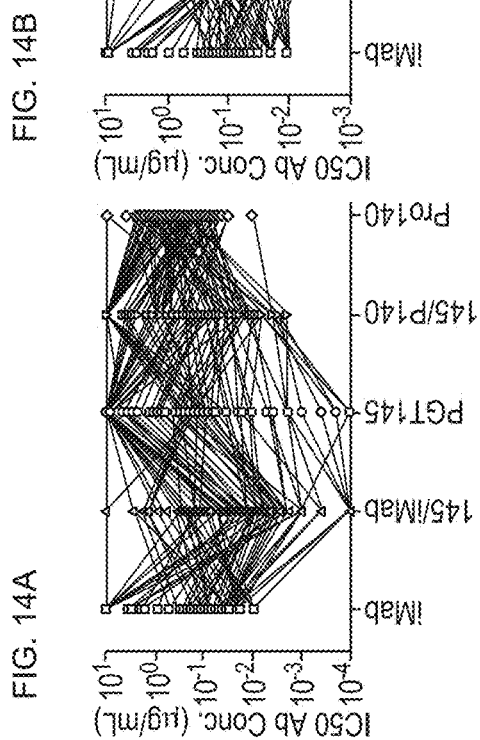
FIG. 14E
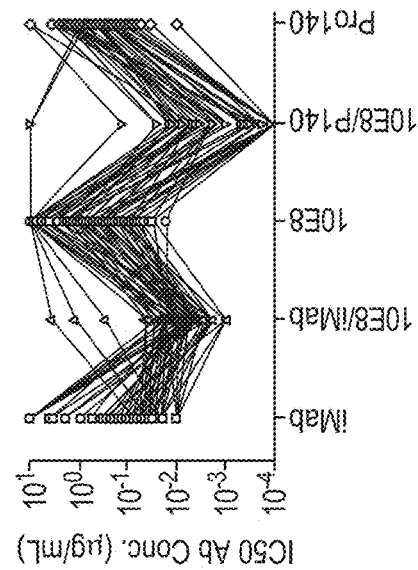
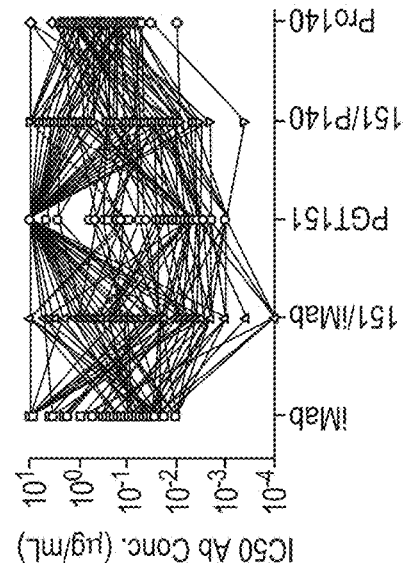

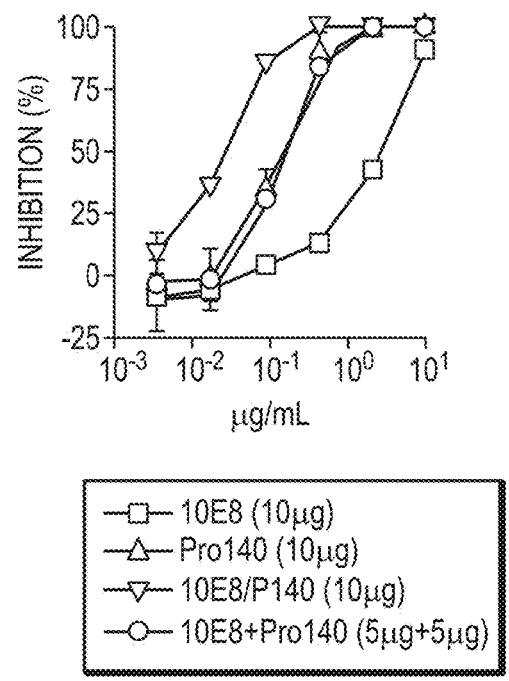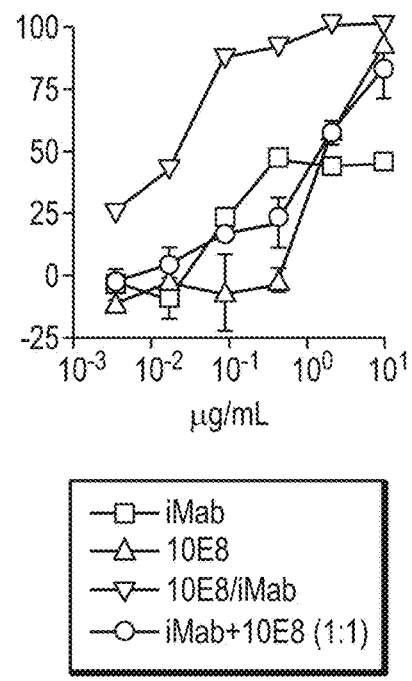

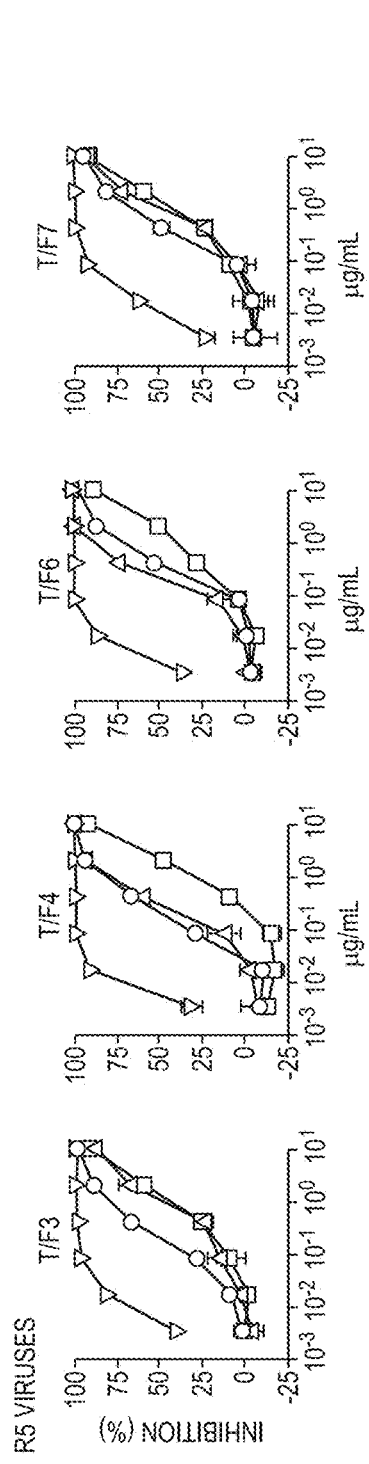

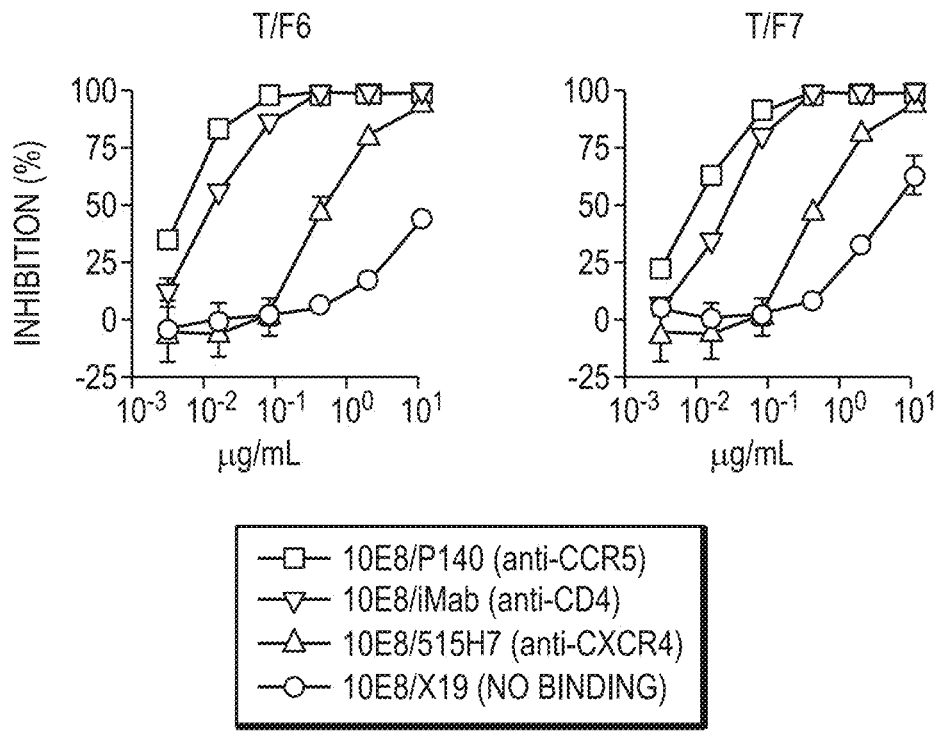

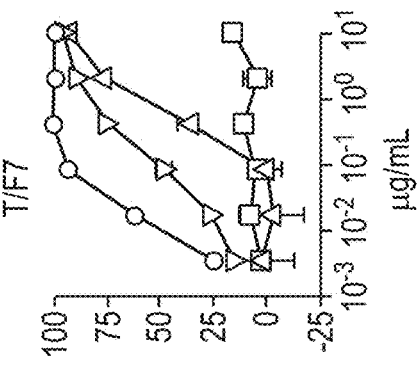
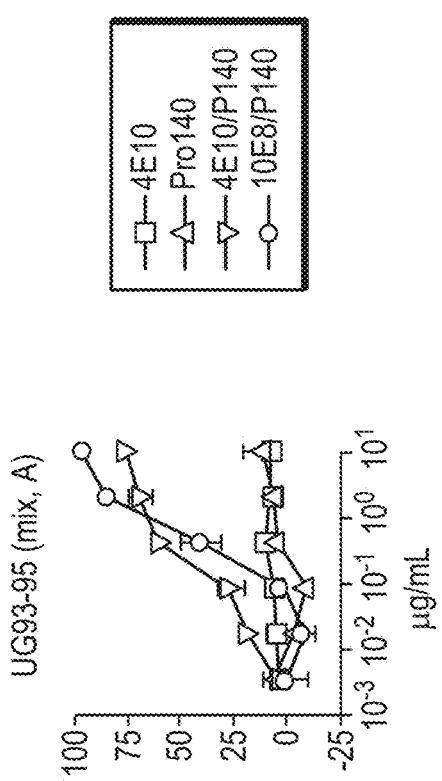
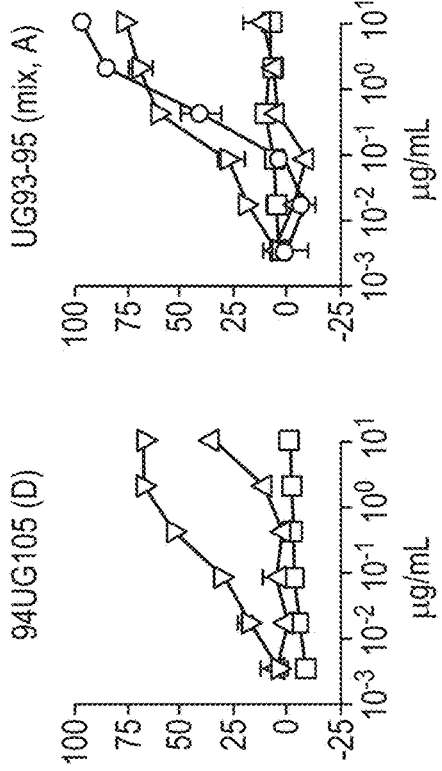
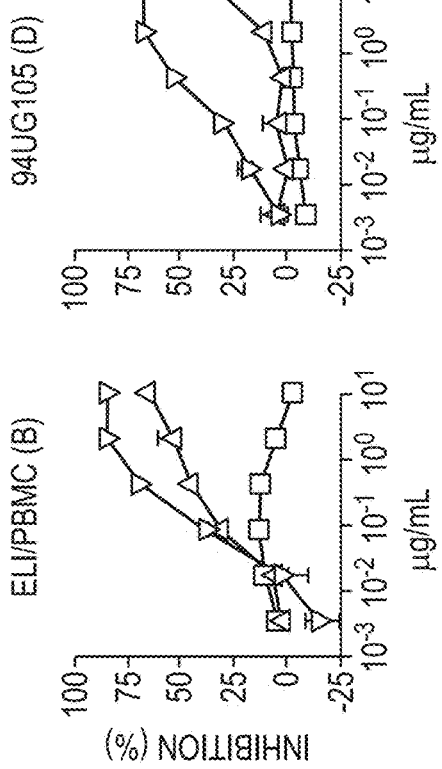
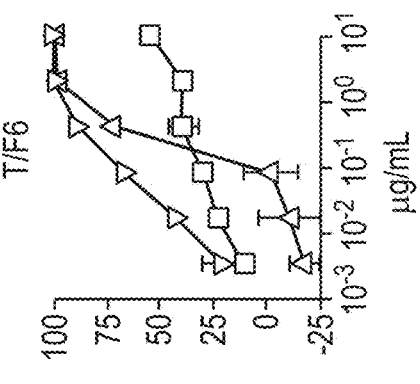
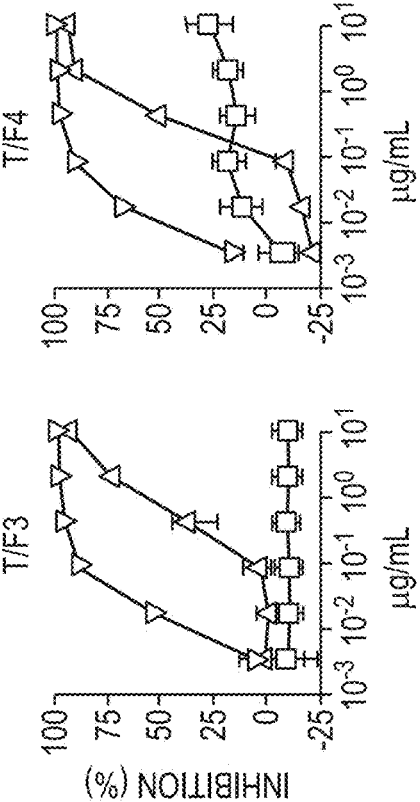

FIG. 25
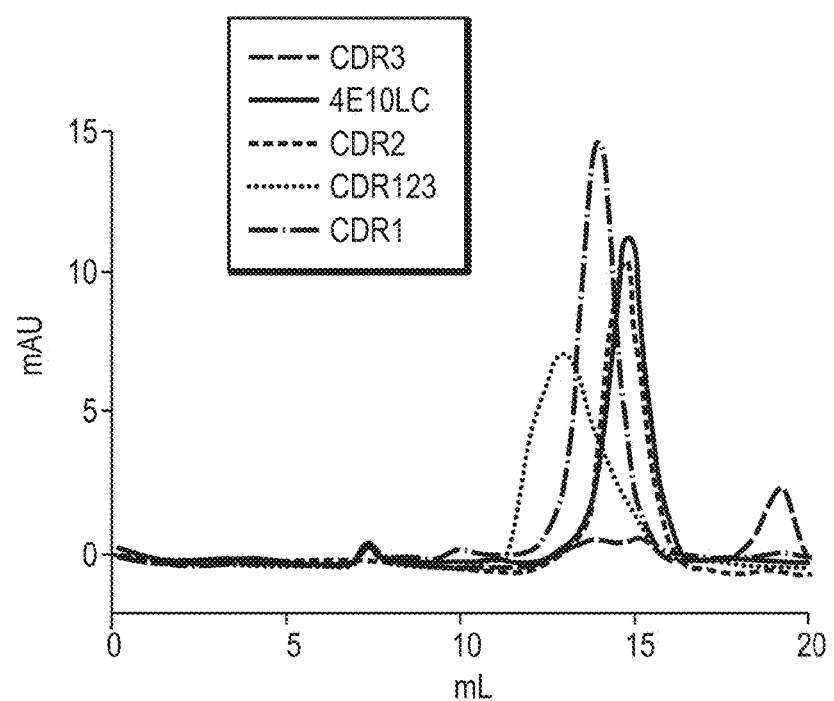
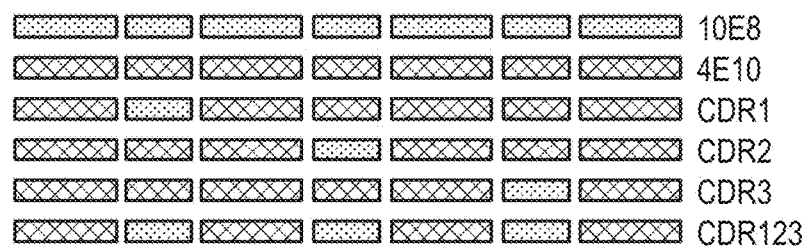

| MODIFICATIONS | EXPRESSION | MPER BINDING | SEC | NEUTRALIZATION |
|---|---|---|---|---|
| 10E8-H/germline-L CDR123 (10E8) | √ | ↓ | √ | ↓ |
| 10E8-H/germline-L FW123 (10E8) | √ | ↓ | √ | ↓ |

FIG. 46

| Construct | H-Chain | L-Chain | Activity | SEC | PK |
|---|---|---|---|---|---|
| 10E8/P140 | | | +++++ | X | X |
| 10E8v1.0/P140 | | | ++ | ✓ | ✓ |
| 10E8v1.1/P140 | | | ++++ | ✓ | ✓ |
| 10E8v2.0/P140 | | | +++ | X | ND |
| 10E8v3.0/P140 | | | +++++ | ✓ | X |
| 10E8/iMab | | | +++ | X | X |
| 10E8v1.0/iMab | | | +++ | X | X |
| 10E8v1.1/iMab | | | +++ | X | X |
| 10E8v2.0/iMab | | | +++++ | ✓ | ✓ |
| 10E8v3.0/iMab | | | ++++ | ✓ | X |

BISPECIFIC HIV-1-NEUTRALIZING ANTIBODIES

CROSS-REFERENCE TO RELATED APPLICATIONS

This application is a continuation-in-part of U.S. Pat. No. 9,884,905, filed Jan. 25, 2017, which is a divisional of U.S. patent application Ser. No. 14/558,341, filed Dec. 2, 2014, which is patented as U.S. Pat. No. 9,587,012, which claims priority to and the benefit of U.S. Provisional Patent Application No. 61/910,685, filed Dec. 2, 2013, each of which is hereby incorporated by reference in its entirety.

FIELD OF THE INVENTION

In various embodiments, the present invention relates generally to using bispecific antibodies in the prevention and treatment of HIV.

SEQUENCE LISTING

The instant application contains a Sequence Listing which has been submitted in ASCII format via EFS-Web and is hereby incorporated by reference in its entirety. Said ASCII copy, created Dec. 21, 2017, is named ADR-001CP_ST25.txt and is 145,851 bytes in size.

BACKGROUND

Passive immunization with antibodies (Abs) is a recognized method of prophylaxis and treatment of infectious diseases. This approach may involve preparing human immunoglobulins from donors who recovered from an infectious disease and utilizing such preparations, containing Abs specific for the infectious organism, to protect a recipient against the same disease. Alternatively, therapeutic antibodies can be made by immunizing mice with an antigen, and then engineering/humanizing the mouse Ab into a human version. Monoclonal antibodies (mAbs) are homogeneous in terms of physical characteristics and immunochemical reactivity, and so offer the possibility of absolute specific activity.

That specificity can ultimately be a limitation for some targets, so practitioners have developed "bispecific" mAbs composed of fragments of two different mAbs and which bind to two different types of antigen. This facilitates binding to antigens expressed only weakly, for example. Some bispecific mAbs can stimulate strong immune responses, limiting their clinical application. One recent approach to ameliorating this effect is "CrossMab" methodology, a bispecific antibody format that adopts a more native antibody-like structure.

The prospects for generating a highly potent bispecific or bivalent antibody against a pathogen, such as HIV, for clinical use involves many uncertainties. The low spike density and spike structure on HIV may impede bivalent binding of antibodies to HIV, for example, and the geometry and spatial relationship of cell surface anchoring are not well-characterized. Nor is it known whether sufficient epitope accessibility on the HIV envelope exists. CrossMab bispecific antibodies that are anchored to a host cell membrane offer the possibility of improved local antibody concentration, targeting of sequential and/or interdependent entry steps, and compensating for monovalent binding.

Further still, large-scale, commercial production of antibodies remains challenging. For example, the production of therapeutic antibodies often requires the use of very large cell cultures followed by extensive purification steps, under Good Manufacturing Practice conditions, thereby resulting in extremely high production costs. Other limitations such as poor insolubility, protein aggregation, and protein instability can also make manufacturing of antibodies less than optimal.

Accordingly, there remains a need for therapeutically effective HIV antibodies that can be easily produced at a commercial scale.

SUMMARY

In one aspect, the present invention pertains to a bispecific antibody for neutralizing HIV. The bispecific antibody includes portions of a first and a second antibody, in which the first antibody binds to a HIV envelope protein. In certain embodiments, the first antibody is selected from PGT145, PG9, PGT128, PGT121, 10-1074, 3BNC117, VRC01, PGT151, 4E10, 10E8 and a variant thereof. In certain embodiments, the bispecific antibody includes portions of a second antibody, in which the second antibody binds to a cell membrane protein. For example, the second antibody binds to a cell receptor protein or a cell membrane co-receptor protein. In an embodiment, the second antibody is selected from a CD4 antibody, a CCR5 antibody and a CXCR4 antibody, such as Pro 140, ibalizumab, 515H7, or a variant thereof. In various embodiments, the bispecific antibody has a CrossMab format.

In another aspect, the present invention provides a bispecific antibody including portions of a first antibody and a second antibody, wherein the first antibody binds to a HIV envelope protein and the second antibody binds to a cell membrane protein. In various embodiments, the bispecific antibody has a CrossMab format.

In various embodiments, pharmaceutical compositions including the bispecific antibodies disclosed herein are also provided. The pharmaceutical composition may be formulated for oral, intranasal, pulmonary, intradermal, transdermal, subcutaneous, intramuscular, intraperitoneal, or intravenous delivery.

In a further aspect, methods for neutralizing HIV are provided. The methods include the steps of contacting an antigen binding site with a bispecific antibody that binds a HIV envelope protein and contacting another antigen binding site with a bispecific antibody that binds a cell membrane protein.

In another aspect, methods for treating a patient infected with HIV are also provided. The methods include administering to the patient any of the bispecific antibodies or pharmaceutical compositions as disclosed herein. In an embodiment, the patient is human.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which:

FIGS. 4A-J are a series of graphs comparing the inhibition of various strains of X4 and dual-tropic HIV using varying concentrations of 10E8, Pro 140 or 10E8/P140 antibodies. P140 is shorthand for Pro 140.

FIGS. 5A-G are a series of graphs comparing the inhibition of various strains of HIV using varying concentrations of 10E8, Pro 140, 10E8/P140 or a combination of the individual 10E8 and Pro 140 monoclonal antibodies.

FIGS. 7A-H are a series of graphs comparing the inhibition of various strains of HIV using varying concentrations of 10E8, Pro 140, 10E8/P140 and 10E8/αHer2 antibodies.

FIG. 8A is a graph comparing the binding of CrossMab bispecific antibodies 10E8/iMab and Δ10E8/iMab to the HIV-1 glycoprotein MPER.

FIGS. 8B-E are a series of graphs comparing the inhibition percentages of 10E8 (light gray lines) and Δ10E8 (dark gray lines) against iMab resistant R5 viruses (FIG. 8B) and X4 viruses (FIG. 8C), as well as the inhibition percentages of 10E8/iMab (light gray lines) and Δ10E8/iMab (dark gray lines) against iMab resistant R5 viruses (FIG. 8D) and X4 viruses (FIG. 8E).

FIGS. 9A-G are a series of graphs comparing the inhibition of various strains of HIV using varying concentrations of 10E8, Δ10E8, 4E10, 10E8/P140, Δ10E8/P140 and 4E10/P140 antibodies.

FIGS. 11A-E are a series of graphs comparing the maximum percentage inhibition (MPI) of a large panel of HIV envelope pseudotyped viruses with the monoclonal antibody iMab (grey bars in all panels) and the CrossMab antibodies PGT145/ibalizumab (145/iMab; FIG. 11A), PGT128/ibalizumab (128/iMab; FIG. 11B), PGT151/ibalizumab (151/iMab; FIG. 11C), 3BNC117/ibalizumab (117/iMab; FIG. 11D) and 10E8/ibalizumab (10E8/iMab; FIG. 11E).

FIGS. 12A-E are a series of graphs comparing the maximum percentage inhibition (MPI) and IC80 antibody concentrations of the CrossMab antibodies PGT145/ibalizumab (145/iMab; FIG. 12A), PGT128/ibalizumab (128/iMab; FIG. 12B), PGT151/ibalizumab (151/iMab; FIG. 12C), 3BNC117/ibalizumab (117/iMab; FIG. 12D) and 10E8/ibalizumab (10E8/iMab; FIG. 12E) against a large panel of HIV envelope pseudotyped viruses.

FIGS. 13A-E are a series of graphs comparing the IC80 antibody concentrations for iMab- and Pro140-based CrossMab bispecific antibodies and their parent antibodies for PGT145/iMab and PGT145/Pro140 (FIG. 13A), 3BNC117/iMab and 3BNC117/Pro140 (FIG. 13B), PGT128/iMab and PGT128/Pro140 (FIG. 13C), PGT151/iMab and PGT151/Pro140 (FIG. 13D) and 10E8/iMab and 10E8/Pro140 (FIG. 13E).

FIGS. 14A-E are a series of graphs comparing the IC50 antibody concentrations for iMab- and Pro140-based CrossMab bispecific antibodies and their parent antibodies for PGT145/iMab and PGT145/Pro140 (FIG. 14A), 3BNC117/iMab and 3BNC117/Pro140 (FIG. 14B), PGT128/iMab and PGT128/Pro140 (FIG. 14C), PGT151/iMab and PGT151/Pro140 (FIG. 14D) and 10E8/iMab and 10E8/Pro140 (FIG. 14E).

FIG. 17A is a graph comparing the inhibition of an HIV strain against varying concentrations of 10E8, Pro 140, 10E8/P140 CrossMab bispecific antibody, and a combination of individual 10E8 and Pro 140 monoclonal antibodies.

FIG. 17B is a graph comparing the inhibition of an HIV strain against varying concentrations of iMab, 10E8, 10E8/iMab CrossMab bispecific antibody, and a combination of individual 10E8 and iMab monoclonal antibodies.

FIGS. 18A-D are a series of graphs comparing the inhibition of various HIV R5 strains against varying concentrations of 10E8, Pro140, 10E8/P140 and 10E8/515H7 antibodies.

FIGS. 18E-H are a series of graphs comparing the inhibition of various HIV X4 strains against various concentrations of 10E8, 515H7 and 10E8/515H7 antibodies.

FIGS. 19A-B are a series of graphs comparing inhibition of various HIV strains against varying concentrations of 10E8/Pro140, 10E8/iMab, 10E8/515H7 and 10E8/X19 antibodies.

FIG. 19C indicates the density of CD4, CCR5 and CXCR4 receptors present on TZM-bl cells.

FIGS. 21A-G are a series of graphs comparing the inhibition of various strains of HIV against varying concentrations of 4E10, Pro140 and 4E10/P140 and 10E8/P140 antibodies.

FIG. 25 is a size exclusion chromatography graph of the monoclonal antibody 4E10 and 4E10 mutants genetically grafted with the light regions of 10E8 that included the CDR1 region, CDR2 region, CDR3 region, or combined CDR1, CDR2 and CDR3 regions.

FIG. 37A demonstrates that some of the 10E8.2/iMab variants retained functional activity in an in vitro HIV-1 neutralization assay. FIG. 37B shows that 10E8.2/iMab and some of the 10E8.2/iMab variants have similar in vivo pharmacokinetic profiles. FIG. 37C shows the precipitation profiles of 10E8.2/iMab and some of the 10E8.2/iMab variants under thermal stress-inducing conditions.

FIG. 46 is a graph showing exemplary variants of 10E8 antibodies that are stable while retaining anti-HIV activity.

DETAILED DESCRIPTION

Embodiments of the present invention provide for inhibition of HIV. In various implementations, bispecific antibodies are formed, each including heavy chain and light chain components from two different parent antibodies. In various embodiments, one parent antibody specifically binds HIV, for example, the HIV envelope protein Env. In various embodiments, the other parent antibody specifically binds a cell membrane protein, for example CD4 and CCR5.

Figure 1:
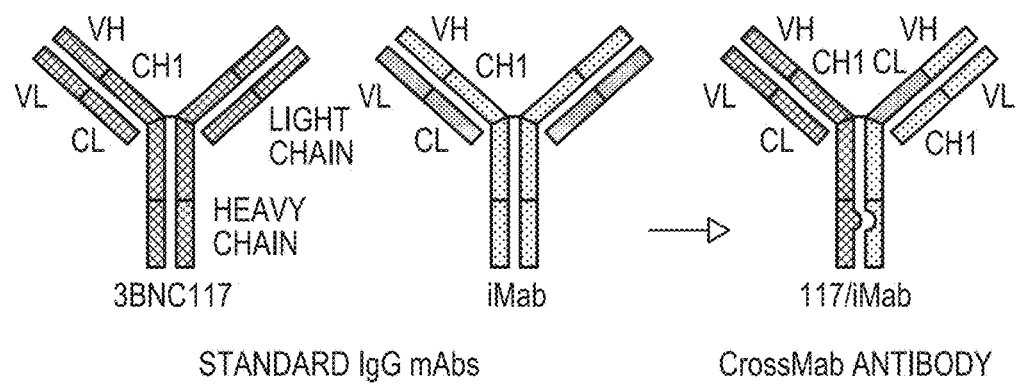
FIG. 1 is a diagram illustrating a CrossMab antibody derived from two IgG monoclonal antibodies.

In various embodiments, the bispecific antibody (e.g., a HIV CrossMab antibody) of the present invention has the natural architecture of an IgG molecule, but with bispecificity. In a bispecific antibody, a heavy chain and light chain from each of two parental antibodies are combined, providing an antibody in which the antigen binding sites of fragment antigen-binding 1 (Fab1) and Fab2 have different binding specificities. In certain embodiments, the bispecific antibody is a CrossMab format antibody, as shown in FIG. 1. In a CrossMab format, one heavy chain includes a "knob" structure and the other heavy chain includes a corresponding "hole" structure, and the positions of the constant domains (i.e., CL and CH1) from one parental antibody are switched, which together ensure correct pairing of heavy chains and light chains during assembly.

Figure 2A:
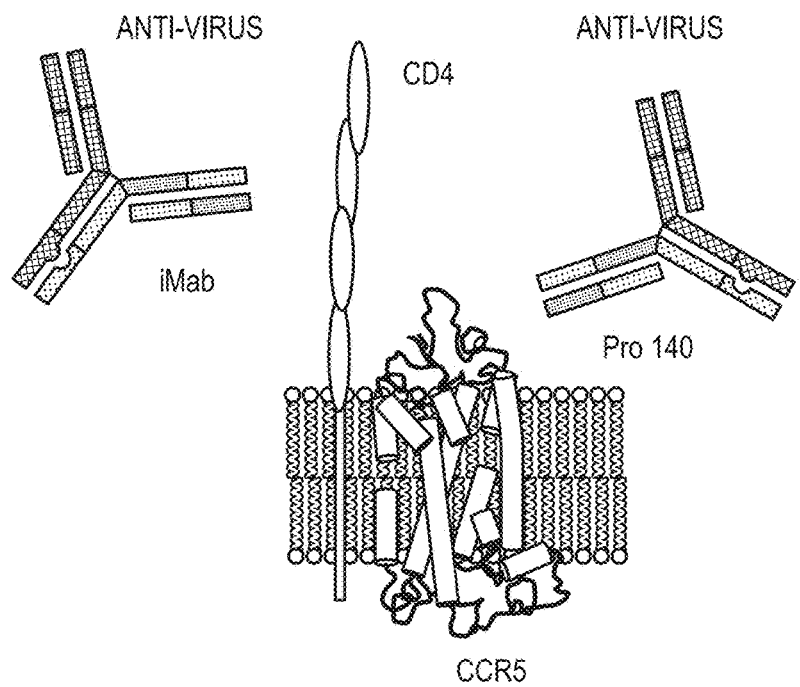
FIG. 2A is a diagram illustrating an iMab antibody (shorthand for the monoclonal antibody ibalizumab) that targets CD4 and a Pro 140 antibody that targets CCR5.
Figure 2B:
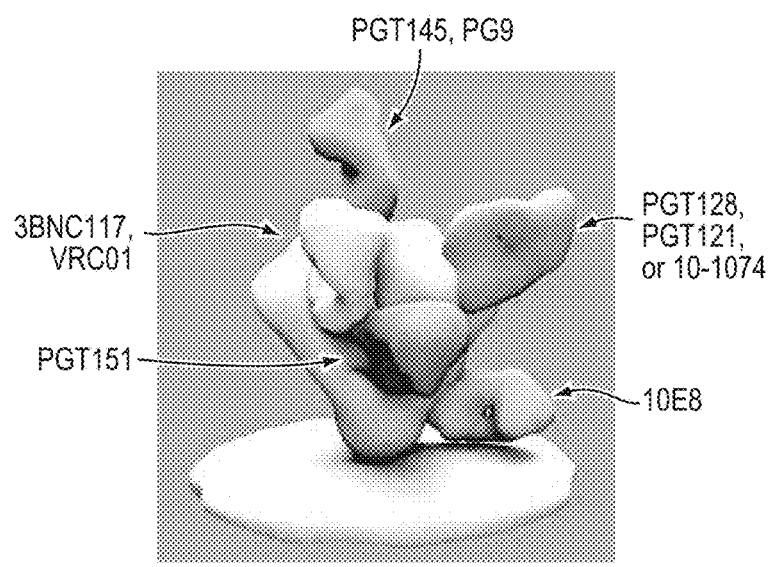
FIG. 2B is a diagram illustrating mAbs that target the HIV envelope gp120.
Figure 10:
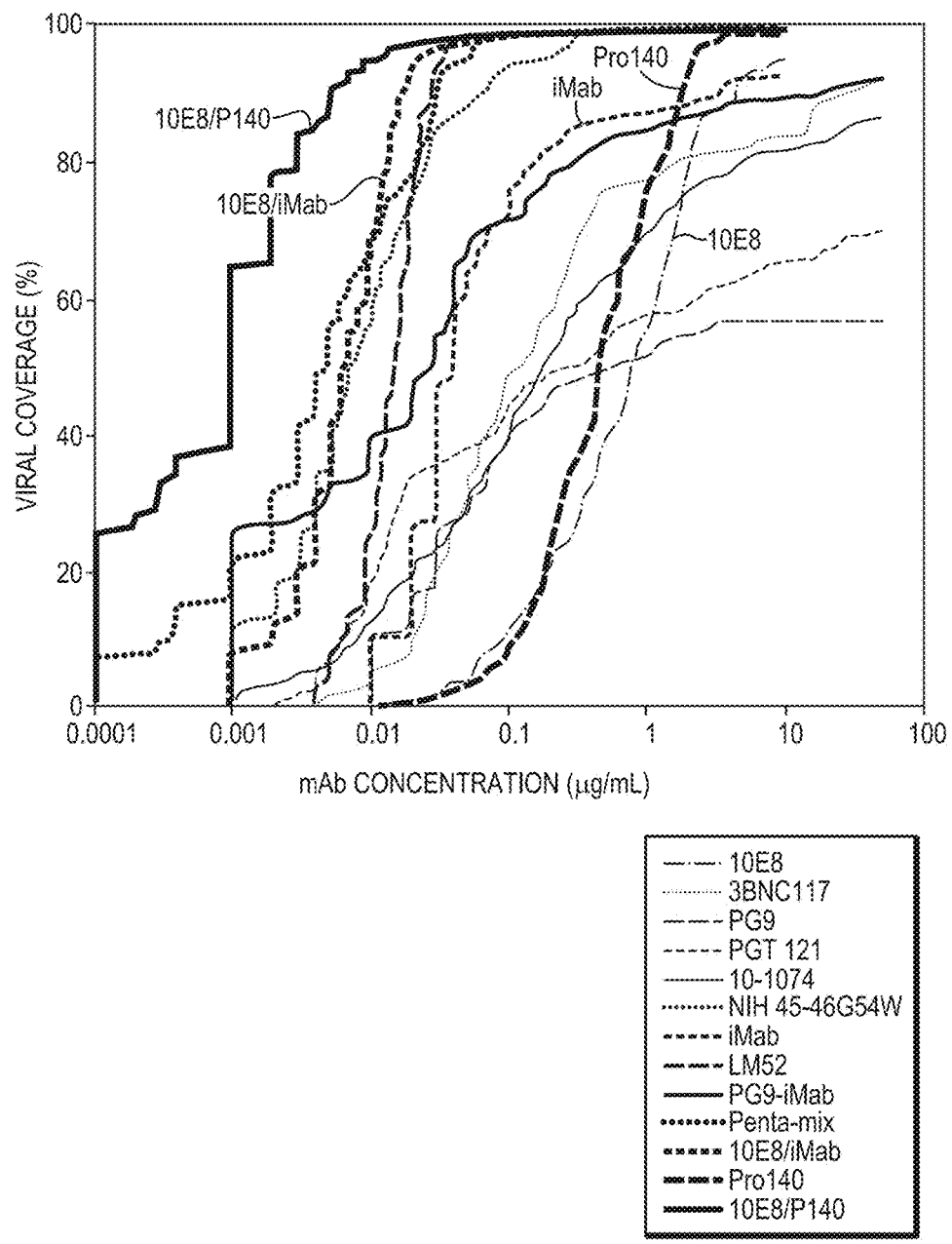
FIG. 10 is a graph comparing the antiviral coverage of the CrossMab antibodies 10E8/Pro140 and 10E8/iMab, their parental monoclonal antibodies 10E8, Pro140 and iMab, and various other HIV envelope-targeting monoclonal antibodies against a large panel of HIV envelope pseudotyped viruses.
Figure 15A:
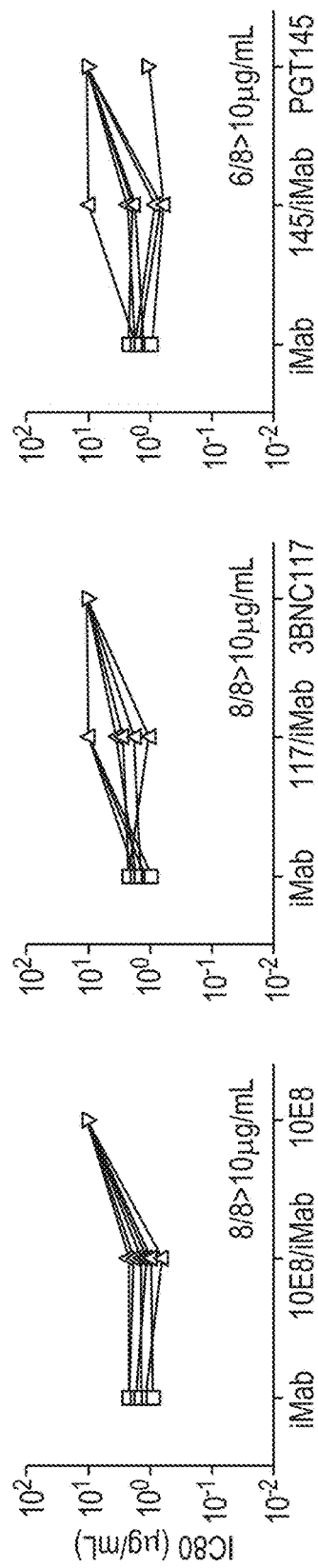
FIGS. 15A-E are graphs displaying the IC80 antibody concentrations for iMab-based CrossMab bispecific antibodies and their parent antibodies against cell-to-cell transmission of HIV for 10E8/iMab (FIG. 15A), 3BNC117/iMab (FIG. 15B), PGT145/iMab (FIG. 15C), PGT128/iMab (FIG. 15D) and PGT151/iMab (FIG. 15E).
Figure 15B:
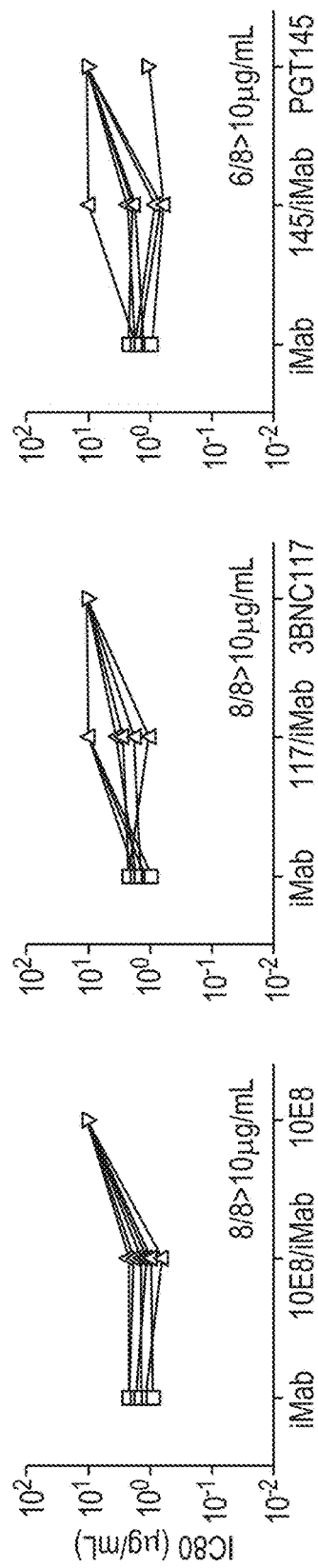
Figure 15C:
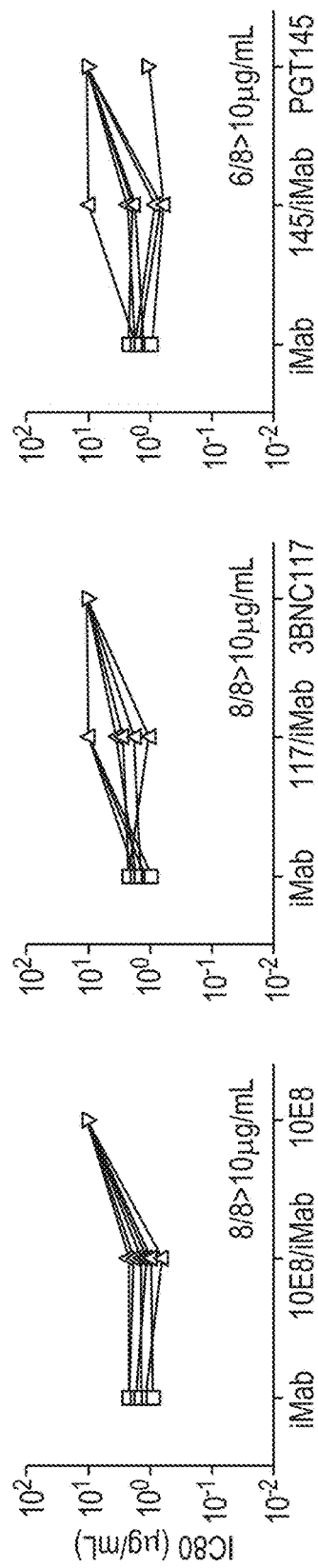
Figure 15D:
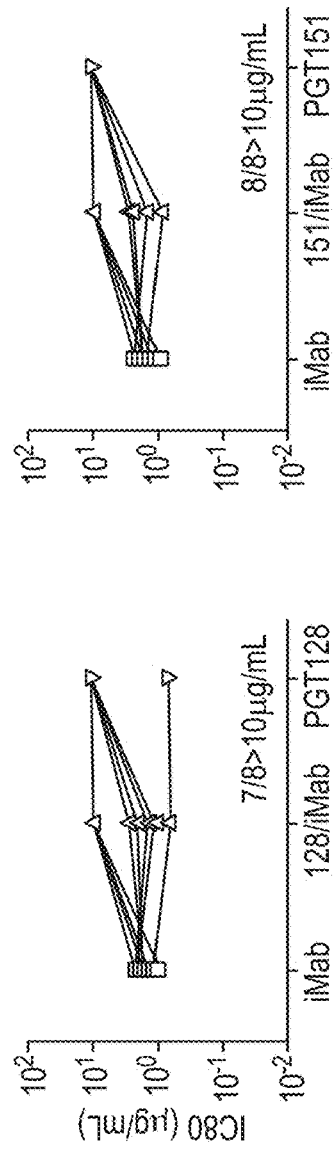
Figure 15E:
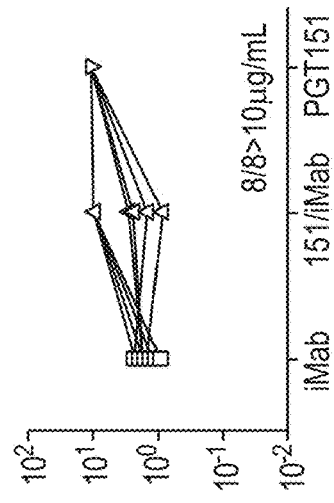

Various mAbs have been shown to block HIV infection by targeting and binding to the HIV envelope protein Env (FIGS. 2B and 10). These mAbs include, for example, PGT145, PG9, PGT128, PGT121, 10-1074, 3BNC117, VRC01, PGT151, 4E10, and 10E8. FIG. 2B (adapted from www.scripps.edu/news/press/2014/20140424hiv.html) illustrates how the mAb PGT145 targets the V1/V2 epitope on the HIV viral envelope gp120; how mAb PGT128 targets the glycan on the V3 stem region of HIV gp120; how mAb 3BNC117 targets the CD4 binding site of HIV gp120; how mAb 10E8 targets the membrane proximal external region (MPER) of HIV gp41; and how mAb PGT151 targets an epitope on both HIV gp120 and HIV gp41.

In addition, monoclonal antibodies Pro 140 ("P140"), Ibalizumab ("iMab") and 515H7 have been shown to block HIV infection by targeting and binding to CCR5, CD4 and CXCR4 human cell membrane proteins, respectively (FIG. 2A). Specifically, FIG. 2A shows how iMab targets CD4, the primary receptor for HIV-1 entry that is expressed on human T-cells; and how Pro 140 targets CCR5, a co-receptor for HIV-1 entry by CCR5 tropic HIV-1.

Although the ensuing discussion focuses on the use of bispecific antibodies directed to Env and the cell membrane proteins CD4 and CCR5, it is to be understood that this is solely for ease of presentation, and that any suitable antibody directed to any HIV epitope and any suitable antibody directed to any suitable cell membrane protein may be used and are within the scope of the invention.

Accordingly, in various embodiments, the present invention provides bispecific antibodies that target and bind to the HIV Env protein as well as the cell membrane proteins CCR5, CD4 and/or CXCR4. In certain embodiments, the bispecific antibodies include sequences (for example, heavy and light chain sequences) derived from, but not limited to, the PGT145, PG9, PGT128, PGT121, 10-1074, 3BNC117, VRC01, PGT151, 4E10, and/or 10E8 antibodies and variants thereof.

The amino acid sequences defining the heavy and light chains of the PGT145 antibody can be found, for example, at www.ncbi.nlm.nih.gov/protein/3U1S_H and http://www.ncbi.nlm.nih.gov/protein/3U1S_L, respectively, the entire contents of which are incorporated herein by reference.

The amino acid sequences defining the heavy and light chains of the PG9 antibody can be found, for example, at www dot ncbi dot nlm dot nih dot gov/protein/3U4E_H and www dot ncbi dot nlm dot nih dot gov/protein/3MUH_L, respectively, the entire contents of which are incorporated herein by reference.

The amino acid sequences defining the heavy and light chains of the PGT128 antibody can be found, for example, at www dot ncbi dot nlm dot nih dot gov/protein/3TYG_H and www dot ncbi dot nlm dot nih dot gov protein/3TYG_L, respectively, the entire contents of which are incorporated herein by reference.

The amino acid sequences defining the heavy and light chains of the PGT121 antibody can be found, for example, at www dot ncbi dot nlm dot nih dot gov/protein/4FQC_H and www dot ncbi dot nlm dot nih dot gov/protein/4FQC_L, respectively, the entire contents of which are incorporated herein by reference.

The amino acid sequences defining the heavy and light chains of the 10-1074 antibody can be found, for example, in Mouquet H., et al., (2012) PNAS, 109(47): E3268-77 (including supplementary information), the entire contents of which are incorporated herein by reference.

The amino acid sequences defining the heavy and light chains of the 3BNC117 antibody can be found, for example, at www dot ncbi dot nlm dot nih dot gov/protein/4LSV_H and www dot ncbi dot nlm dot nih dot gov/protein/4LSV_L, respectively, the entire contents of which are incorporated herein by reference.

The amino acid sequences defining the heavy and light chains of the VRC01 antibody can be found, for example, at www dot ncbi dot nlm dot nih dot gov/protein/4LST_H and www dot ncbi dot nlm dot nih dot gov/protein/4LST_L, respectively, the entire contents of which are incorporated herein by reference.

The amino acid sequences defining the heavy and light chains of the PGT151 antibody can be found, for example, at www dot ncbi dot nlm dot nih dot gov/protein/4NUG_H and www dot ncbi dot nlm dot nih dot gov/protein/4NUG_L, respectively, the entire contents of which are incorporated herein by reference.

The amino acid sequences defining the heavy and light chains of the 4E10 antibody can be found, for example, at www dot ncbi dot nlm dot nih dot gov/protein/4LLV_H and www dot ncbi dot nlm dot nih dot gov/protein/4LLV_L, respectively, the entire contents of which are incorporated herein by reference.

The amino acid sequences defining the heavy and light chains of the 10E8 antibody can be found, for example, at www dot ncbi dot nlm dot nih dot gov/protein/4G6F_B and www dot ncbi dot nlm dot nih dot gov/protein/4G6F_D, respectively, the entire contents of which are incorporated herein by reference.

In certain embodiments, the bispecific antibodies include sequences (for example, heavy and light chain sequences) derived from, but not limited to, the P140, iMab (or the MV1 variant) and/or 515H7 antibodies and variants thereof. The heavy and light chain sequences of the Pro 140, iMab (or its MV1 variant), and 515H7 antibodies are further described, for example, in Olson, W. C. et al., (1999) J Virol., 73(5): 4145-55, Trkola, A. et al., (2001) J Virol., 75(2):579-88, U.S. Pat. No. 7,122,185, Burkly L. C. et al., (1992) J Immunol., 149(5):1779-87, Moore J. P. et al., (1992) J Virol., 66(8): 4784-93, Reimann K. A., et al., (1997) AIDS Res Hum Retroviruses, 13(11):933-43, International Patent Publication No. WO2014100139, and European Patent Publication No. EP2246364, the entire contents of all of which are incorporated herein by reference.

As used herein, an antibody "variant" refers to an antibody which has an amino acid sequence which differs from the amino acid sequence of a parent antibody from which it is derived. In various embodiments, the variant has one or more amino acid alterations with respect to the parent antibody.

In various embodiments, the bispecific antibody of the present invention includes a heavy and light chain sequence from the PGT145, PG9, PGT128, PGT121, 10-1074, 3BNC117, VRC01, PGT151, 4E10, or 10E8 antibody or a variant thereof and a heavy and light chain sequence from the P140, iMab (or the MV1 variant), or 515H7 antibody or a variant thereof.

In exemplary embodiments, a series of HIV CrossMab antibodies have been constructed including but not limited to, for example, 145/MV1, 117/MV1, 128/MV1, 10E8/MV1, 145/P140, 128/P140, 117/P140, 10E8/P140, 10E8/alpha-Her2, 10E8/X19, and 4E10/P140. PGT145 ("145"), 3BNC117 ("117"), PGT128 ("128"), and 10E8 are four different HIV envelope antibodies. Pro 140 ("P140") is a mAb that binds to the cell surface receptor CCR5. MV1 is a CD4 antibody that is a modified variant of the mAb Ibalizumab ("iMab"; see, for example, International Patent Publication No. WO2014100139, incorporated herein by reference in its entirety). X19 is one of the antibody variants of the anti-cell surface receptor CXCR4 (see, for example, U.S. Pat. No. 8,329,178, incorporated herein by reference in its entirety) that does not bind to cells expressing CXCR4 (and is therefore used as a non-surface binding control). Alpha-Her2 is a mAb that binds to the Her2 receptor expressed on cells. Many of these CrossMab antibodies increase the breadth of HIV neutralization as compared to their parental antibodies (i.e., monoclonal antibodies MV1, 145, 117 or 10E8). In various embodiments, the bispecific antibodies of the invention significantly increase the potency of neutralization against HIV as compared to their parental antibodies.

The amino acid sequences defining the heavy and light chains of various exemplary HIV CrossMab antibodies are shown below.

145/MV1 antibody:

Amino acid sequence defining the MV1 derived light chain of the 145/MV1 antibody—MV1-VLCH1 (SEQ ID NO:1):

DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the MV1 derived heavy chain of the 145/MV1 antibody—MV1-HC-Hole-Cross (SEQ ID NO:2):

QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the PGT145 derived light chain of the 145/MV1 antibody—PGT145-LC (SEQ ID NO:3):

EVVITQSPLFLPVTPGEAASLSCKCSHSLQHSTGANYLAWYLQRPGQTPR

LLIHLATHRASGVPDRFSGSGSGTDFTLKISRVESDDVGTYYCMQGLHSP

WTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

Amino acid sequence defining the PGT145 derived heavy chain of the 145/MV1 antibody—PGT145-HC-Knob (SEQ ID NO:4):

QVQLVQSGAEVKKPGSSVKVSCKASGNSFSNHDVHWVRQATGQGLEWMGW

MSHEGDKTGLAQKFQGRVTITRDSGASTVYMELRGLTADDTAIYYCLTGS

KHRLRDYFLYNEYGPNYEEWGDYLATLDVWGHGTAVTVSSASTKGPSVFP

LAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCP

PCPAPEFEGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPASIEKTISKAKGQPREPQVYTLPPCRDELTKNQVSLWCLVKGFYPSDI

AVEWESNGQPENNYKTTPPVLDSDGSFFLYSKLTVDKSRWQQGNVFSCSV

LHEALHSHYTQKSLSLSPGK

117/MV1 antibody:

Amino acid sequence defining the MV1 derived light chain of the 117/MV1 antibody—MV1-VLCH1 (SEQ ID NO:1):

DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the MV1 derived heavy chain of the 117/MV1 antibody—MV1-HC-Hole-Cross (SEQ ID NO:2):

QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the 3BNC117 derived light chain of the 117/MV1 antibody—3BNC117-LC (SEQ ID NO:5):

DIQMTQSPSSLSASVGDTVTITCQANGYLNWYQQRRGKAPKLLIYDGSKL

ERGVPSRFSGRRWGQEYNLTINNLQPEDIATYFCQVYEFVVFGQGTKVQV

DIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSP

VTKSFNRGEC

Amino acid sequence defining the 3BNC117 derived heavy chain of the 117/MV1 antibody—3BNC117-HC-Knob (SEQ ID NO:6):

QVQLLQSGAAVTKPGASVRVSCEASGYNIRDYFIHWWRQAPGQGLQWVGW

INPKTGQPNNPRQFQGRVSLTRHASWDFDTFSFYMDLKALRSDDTAVYFC

ARQRSDYWDFDVWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPKSCDKTHTCPPCPAPEFEGGPSVFLFP

PKPKDTLMISRTPEVTCVVVDVSHEDPEVKFNWYVDGVEVHNAKTKPREE

-continued

QYNSTYRVVSVLTVLHQDWLNGKEYKCKVSNKALPASIEKTISKAKGQPR

EPQVYTLPPCRDELTKNQVSLWCLVKGFYPSDIAVEWESNGQPENNYKTT

PPVLDSDGSFFLYSKLTVDKSRWQQGNVFSCSVLHEALHSHYTQKSLSLS

PGK

128/MV1 antibody:
Amino acid sequence defining the MV1 derived light chain of the 128/MV1 antibody—MV1-VLCH1 (SEQ ID NO:1):

DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the MV1 derived heavy chain of the 128/MV1 antibody—MV1-HC-Hole-Cross (SEQ ID NO:2):

QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the PGT128 derived light chain of the 128/MV1 antibody—PGT128-LC (SEQ ID NO:7):

QSALTQPPSASGSPGQSITISCTGTSNNFVSWYQQHAGKAPKLVIYDVNK

RPSGVPDRFSGSKSGNTASLTVSGLQTDDEAVYYCGSLVGNWDVIFGGGT

KLTVLGQPKAAPSVTLFPPSSEELQANKATLVCLISDFYPGAVTVAWKAD

SSPVKAGVETTTPSKQSNNKYAASSYLSLTPEQWKSHRSYSCQVTHEGST

VEKTVAPTECS

Amino acid sequence defining the PGT128 derived heavy chain of the 128/MV1 antibody—PGT128-HC-Knob (SEQ ID NO:8):

QPQLQESGPTLVEASETLSLTCAVSGDSTAACNSFWGWVRQPPGKGLEWV

GSLSHCASYWNRGWTYHNPSLKSRLTLALDTPKNLVFLKLNSVTAADTAT

YYCARFGGEVLRYTDWPKPAWVDLWGRGTLVTVSSASTKGPSVFPLAPSS

KSTSGGTAALGCLVKDYFPEPVTVSWNSGALTSGVHTFPAVLQSSGLYSL

-continued

SSVVTVPSSSLGTQTYICNVNHKPSNTKVDKKVEPKSCDKTHTCPPCPAP

EFEGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPASI

EKTISKAKGQPREPQVYTLPPCRDELTKNQVSLWCLVKGFYPSDIAVEWE

SNGQPENNYKTTPPVLDSDGSFFLYSKLTVDKSRWQQGNVFSCSVLHEAL

HSHYTQKSLSLSPGK

10E8/MV1 antibody:
Amino acid sequence defining the MV1 derived light chain of the 10E8/MV1 antibody—MV1-VLCH1 (SEQ ID NO:1):

DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the MV1 derived heavy chain of the 10E8/MV1 antibody—MV1-HC-Hole-Cross (SEQ ID NO:2):

QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the 10E8 derived light chain of the 10E8/MV1 antibody—10E8-LC (SEQ ID NO:9):

YELTQETGVSVALGRTVTITCRGDSLRSHYASWYQKKPGQAPILLFYGKN

NRPSGVPDRFSGSASGNRASLTISGAQAEDDAEYYCSSRDKSGSRLSVFG

GGTKLTVLSQPKAAPSVTLFPPSSEELQANKATLVCLISDFYPGAVTVAW

KADSSPVKAGVETTTPSKQSNNKYAASSYLSLTPEQWKSHRSYSCQVTHE

GSTVEKTVAPTECS

Amino acid sequence defining the 10E8 derived heavy chain of the 10E8/MV1 antibody—10E8-HC-Knob (SEQ ID NO:10):

EVQLVESGGGLVKPGGSLRLSCSASGFDFDNAWMTWVRQPPGKGLEWVGR

ITGPGEGWSVDYAAPVEGRFTISRLNSINFLYLEMNNLRMEDSGLYFCAR

-continued

TGKYYDFWSGYPPGEEYFQDWGRGTLVTVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK

Δ10E8/MV1 antibody

Amino acid sequence defining the MV1 derived light chain of the Δ10E8/MV1 antibody MV1-VLCH1 (SEQ ID NO:1):

DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the MV1 derived heavy chain of the Δ10E8/MV1 antibody MV1-HC-Hole-Cross (SEQ ID NO:2):

QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the Δ10E8 derived light chain of the Δ10E8/MV1 antibody Δ10E8-LC (SEQ ID NO:21):

YELTQETGVSVALGRTVTITCRGDSLRSHYASWYQKKPGQAPILLFYGKN

NRPSGVPDRFSGASGNRASLTISGAQAEDDAEYYCSSRDKSGSRLSVFGG

GTKLTVLSQPKAAPSVTLFPPSSEELQANKATLVCLISDFYPGAVTVAWK

ADSSPVKAGVETTTPSKQSNNKYAASSYLSLTPEQWKSHRSYSCQVTHEG

STVEKTVAPTECS

Amino acid sequence defining the Δ10E8 derived heavy chain of the Δ10E8/MV1 antibody 10E8-HC-Knob (SEQ ID NO:22):

EVQLVESGGGLVKPGGSLRLSCSASGFDFDNAWMTWVRQPPGKGLEWVGR

ITGPGEGWSVDYAAPVEGRFTISRLNSINFLYLEMNNLRMEDSGLYFCAR

TGKYYDFWSGYPPGEEYFQDWGRGTLVTVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK

151/MV1 antibody

Amino acid sequence defining the MV1 derived light chain of the 151/MV1 antibody—MV1-VLCH1 (SEQ ID NO:1):

DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the MV1 derived heavy chain of the 151/MV1 antibody MV1-HC-Hole-Cross (SEQ ID NO:2):

QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the PGT151 derived light chain of the 151/MV1 antibody PGT151-LC (SEQ ID NO:23):

DIVMTQTPLSLSVTPGQPASISCKSSESLRQSNGKTSLYWYRQKPGQSPQ

LLVFEVSNRFSGVSDRFVGSGSGTDFTLRISRVEAEDVGFYYCMQSKDFP

LTFGGGTKVDLKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

Amino acid sequence defining the PGT151 derived heavy chain of the 151/MV1 antibody PGT151-HC-Knob (SEQ ID NO:24):

RVQLVESGGGVVQPGKSVRLSCVVSDFPFSKYPMYWVRQAPGKGLEWVAA

ISGDAWHVVYSNSVQGRFLVSRDNVKNTLYLEMNSLKIEDTAVYRCARMF

QESGPPRLDRWSGRNYYYYSGMDVWGQGTTVTVSSASTKGPSVFPLAPSS

KSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAP

EFEGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPASI

EKTISKAKGQPREPQVYTLPPCRDELTKNQVSLWCLVKGFYPSDIAVEWE

SNGQPENNYKTTPPVLDSDGSFFLYSKLTVDKSRWQQGNVFSCSVLHEAL

HSHYTQKSLSLSPGK

145/P140 antibody:
Amino acid sequence defining the Pro 140 derived light chain of the 145/P140 antibody—PRO140-VLCH1 (SEQ ID NO:11):

DIVMTQSPLSLPVTPGEPASISCRSSQRLLSSYGHTYLHWYLQKPGQSPQ

LLIYEVSNRFSGVPDRFSGSGSGTDFTLKISRVEAEDVGVYYCSQSTHVP

LTFGQGTKVEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the Pro 140 derived heavy chain of the 145/P140 antibody—PRO140-HC-Hole-Cross (SEQ ID NO:12):

EVQLVESGGGLVKPGGSLRLSCAASGYTFSNYWIGWVRQAPGKGLEWIGD

IYPGGNYIRNNEKFKDKTTLSADTSKNTAYLQMNSLKTEDTAVYYCGSSF

GSNYVFAWFTYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the PGT145 derived light chain of the 145/P140 antibody—PGT145-LC (SEQ ID NO:3):

EVVITQSPLFLPVTPGEAASLSCKCSHSLQHSTGANYLAWYLQRPGQTPR

LLIHLATHRASGVPDRFSGSGSGTDFTLKISRVESDDVGTYYCMQGLHSP

WTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

Amino acid sequence defining the PGT145 derived heavy chain of the 145/P140 antibody—PGT145-HC-Knob (SEQ ID NO:4):

QVQLVQSGAEVKKPGSSVKVSCKASGNSFSNHDVHWVRQATGQGLEWMGW

MSHEGDKTGLAQKFQGRVTITRDSGASTVYMELRGLTADDTAIYYCLTGS

KHRLRDYFLYNEYGPNYEEWGDYLATLDVWGHGTAVTVSSASTKGPSVFP

LAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCP

PCPAPEFEGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPASIEKTISKAKGQPREPQVYTLPPCRDELTKNQVSLWCLVKGFYPSDI

AVEWESNGQPENNYKTTPPVLDSDGSFFLYSKLTVDKSRWQQGNVFSCSV

LHEALHSHYTQKSLSLSPGK

117/P140 antibody:
Amino acid sequence defining the Pro 140 derived light chain of the 117/P140 antibody—PRO140-VLCH1 (SEQ ID NO:11):

DIVMTQSPLSLPVTPGEPASISCRSSQRLLSSYGHTYLHWYLQKPGQSPQ

LLIYEVSNRFSGVPDRFSGSGSGTDFTLKISRVEAEDVGVYYCSQSTHVP

LTFGQGTKVEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the Pro 140 derived heavy chain of the 117/P140 antibody—PRO140-HC-Hole-Cross (SEQ ID NO:12):

EVQLVESGGGLVKPGGSLRLSCAASGYTFSNYWIGWVRQAPGKGLEWIGD

IYPGGNYIRNNEKFKDKTTLSADTSKNTAYLQMNSLKTEDTAVYYCGSSF

GSNYVFAWFTYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the 3BNC117 derived light chain of the 117/P140 antibody—3BNC117-LC (SEQ ID NO:5):

DIQMTQSPSSLSASVGDTVTITCQANGYLNWYQQRRGKAPKLLIYDGSKL

ERGVPSRFSGRRWGQEYNLTINNLQPEDIATYFCQVYEFVVFGQGTKVQV

DIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSP

VTKSFNRGEC

Amino acid sequence defining the 3BNC117 derived heavy chain of the 117/P140 antibody—3BNC117-HC-Knob (SEQ ID NO:6):

QVQLLQSGAAVTKPGASVRVSCEASGYNIRDYFIHWWRQAPGQGLQWVGW

INPKTGQPNNPRQFQGRVSLTRHASWDFDTFSFYMDLKALRSDDTAVYFC

ARQRSDYWDFDVWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPKSCDKTHTCPPCPAPEFEGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPASIEKTISKAKGQPR

EPQVYTLPPCRDELTKNQVSLWCLVKGFYPSDIAVEWESNGQPENNYKTT

PPVLDSDGSFFLYSKLTVDKSRWQQGNVFSCSVLHEALHSHYTQKSLSLS

PGK

128/P140 antibody:
Amino acid sequence defining the Pro 140 derived light chain of the 128/P140 antibody—PRO140-VLCH1 (SEQ ID NO:11):

DIVMTQSPLSLPVTPGEPASISCRSSQRLLSSYGHTYLHWYLQKPGQSPQ

LLIYEVSNRFSGVPDRFSGSGSGTDFTLKISRVEAEDVGVYYCSQSTHVP

LTFGQGTKVEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the Pro 140 derived heavy chain of the 128/P140 antibody—PRO140-HC-Hole-Cross (SEQ ID NO:12):

EVQLVESGGGLVKPGGSLRLSCAASGYTFSNYWIGWVRQAPGKGLEWIGD

IYPGGNYIRNNEKFKDKTTLSADTSKNTAYLQMNSLKTEDTAVYYCGSSF

GSNYVFAWFTYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the PGT128 derived light chain of the 128/P140 antibody—PGT128-LC (SEQ ID NO:7):

QSALTQPPSASGSPGQSITISCTGTSNNFVSWYQQHAGKAPKLVIYDVNK

RPSGVPDRFSGSKSGNTASLTVSGLQTDDEAVYYCGSLVGNWDVIFGGGT

KLTVLGQPKAAPSVTLFPPSSEELQANKATLVCLISDFYPGAVTVAWKAD

SSPVKAGVETTTPSKQSNNKYAASSYLSLTPEQWKSHRSYSCQVTHEGST

VEKTVAPTECS

Amino acid sequence defining the PGT128 derived heavy chain of the 128/P140 antibody—PGT128-HC-Knob (SEQ ID NO:8):

QPQLQESGPTLVEASETLSLTCAVSGDSTAACNSFWGWVRQPPGKGLEWV

GSLSHCASYWNRGWTYHNPSLKSRLTLALDTPKNLVFLKLNSVTAADTAT

YYCARFGGEVLRYTDWPKPAWVDLWGRGTLVTVSSASTKGPSVFPLAPSS

KSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAP

EFEGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPASI

EKTISKAKGQPREPQVYTLPPCRDELTKNQVSLWCLVKGFYPSDIAVEWE

SNGQPENNYKTTPPVLDSDGSFFLYSKLTVDKSRWQQGNVFSCSVLHEAL

HSHYTQKSLSLSPGK

10E8/P140 antibody:
Amino acid sequence defining the Pro 140 derived light chain of the 10E8/P140 antibody—PRO140-VLCH1 (SEQ ID NO:11):

DIVMTQSPLSLPVTPGEPASISCRSSQRLLSSYGHTYLHWYLQKPGQSPQ

LLIYEVSNRFSGVPDRFSGSGSGTDFTLKISRVEAEDVGVYYCSQSTHVP

LTFGQGTKVEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the Pro 140 derived heavy chain of the 10E8/P140 antibody—PRO140-HC-Hole-Cross (SEQ ID NO:12):

EVQLVESGGGLVKPGGSLRLSCAASGYTFSNYWIGWVRQAPGKGLEWIGD

IYPGGNYIRNNEKFKDKTTLSADTSKNTAYLQMNSLKTEDTAVYYCGSSF

GSNYVFAWFTYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the 10E8 derived light chain of the 10E8/P140 antibody—10E8-LC (SEQ ID NO:9):

YELTQETGVSVALGRTVTITCRGDSLRSHYASWYQKKPGQAPILLFYGKN

NRPSGVPDRFSGSASGNRASLTISGAQAEDDAEYYCSSRDKSGSRLSVFG

GGTKLTVLSQPKAAPSVTLFPPSSEELQANKATLVCLISDFYPGAVTVAW

KADSSPVKAGVETTTPSKQSNNKYAASSYLSLTPEQWKSHRSYSCQVTHE

GSTVEKTVAPTECS

Amino acid sequence defining the 10E8 derived heavy chain of the 10E8/P140 antibody—10E8-HC-Knob (SEQ ID NO:10):

EVQLVESGGGLVKPGGSLRLSCSASGFDFDNAWMTWVRQPPGKGLEWVGR

ITGPGEGWSVDYAAPVEGRFTISRLNSINFLYLEMNNLRMEDSGLYFCAR

TGKYYDFWSGYPPGEEYFQDWGRGTLVTVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK

Δ10E8/P140 antibody
Amino acid sequence defining the PRO140 derived light chain of the Δ10E8/P140 antibody—PRO140-VLCH1 (SEQ ID NO:11):

DIVMTQSPLSLPVTPGEPASISCRSSQRLLSSYGHTYLHWYLQKPGQSPQ

LLIYEVSNRFSGVPDRFSGSGSGTDFTLKISRVEAEDVGVYYCSQSTHVP

LTFGQGTKVEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the PRO140 derived heavy chain of the Δ10E8/P140 antibody—PRO140-Hole-Cross (SEQ ID NO:12):

EVQLVESGGGLVKPGGSLRLSCAASGYTFSNYWIGWVRQAPGKGLEWIGD

IYPGGNYIRNNEKFKDKTTLSADTSKNTAYLQMNSLKTEDTAVYYCGSSF

GSNYVFAWFTYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the Δ10E8 derived light chain of the Δ10E8/P140 antibody—Δ10E8-LC (SEQ ID NO:21):

YELTQETGVSVALGRTVTITCRGDSLRSHYASWYQKKPGQAPILLFYGKN

NRPSGVPDRFSGASGNRASLTISGAQAEDDAEYYCSSRDKSGSRLSVFGG

GTKLTVLSQPKAAPSVTLFPPSSEELQANKATLVCLISDFYPGAVTVAWK

ADSSPVKAGVETTTPSKQSNNKYAASSYLSLTPEQWKSHRSYSCQVTHEG

STVEKTVAPTECS

Amino acid sequence defining the Δ10E8 derived heavy chain of the Δ10E8/P140 antibody—10E8-HC-Knob (SEQ ID NO:22):

EVQLVESGGGLVKPGGSLRLSCSASGFDFDNAWMTWVRQPPGKGLEWVGR

ITGPGEGWSVDYAAPVEGRFTISRLNSINFLYLEMNNLRMEDSGLYFCAR

TGKYYDFWSGYPPGEEYFQDWGRGTLVTVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK

151/P140 antibody
Amino acid sequence defining the PRO140 derived light chain of the 151/P140 antibody—PRO140-VLCH1 (SEQ ID NO:11):

DIVMTQSPLSLPVTPGEPASISCRSSQRLLSSYGHTYLHWYLQKPGQSPQ

LLIYEVSNRFSGVPDRFSGSGSGTDFTLKISRVEAEDVGVYYCSQSTHVP

LTFGQGTKVEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the PRO140 derived heavy chain of the 151/P140 antibody—PRO140-Hole-Cross (SEQ ID NO:12):

EVQLVESGGGLVKPGGSLRLSCAASGYTFSNYWIGWVRQAPGKGLEWIGD

IYPGGNYIRNNEKFKDKTTLSADTSKNTAYLQMNSLKTEDTAVYYCGSSF

GSNYVFAWFTYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the PGT151 derived light chain of the 151/P140 antibody—PGT151-LC (SEQ ID NO:23):

DIVMTQTPLSLSVTPGQPASISCKSSESLRQSNGKTSLYWYRQKPGQSPQ

LLVFEVSNRFSGVSDRFVGSGSGTDFTLRISRVEAEDVGFYYCMQSKDFP

LTFGGGTKVDLKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

Amino acid sequence defining the PGT151 derived heavy chain of the 151/P140 antibody—PGT151-HC-Knob (SEQ ID NO:24):

RVQLVESGGGVVQPGKSVRLSCVVSDFPFSKYPMYWVRQAPGKGLEWVAA

ISGDAWHVVYSNSVQGRFLVSRDNVKNTLYLEMNSLKIEDTAVYRCARMF

QESGPPRLDRWSGRNYYYSGMDVWGQGTTVTVSSASTKGPSVFPLAPSS

KSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAP

EFEGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPASI

EKTISKAKGQPREPQVYTLPPCRDELTKNQVSLWCLVKGFYPSDIAVEWE

SNGQPENNYKTTPPVLDSDGSFFLYSKLTVDKSRWQQGNVFSCSVLHEAL

HSHYTQKSLSLSPGK

10E8/Alpha-Her2 antibody:
Amino acid sequence defining the alpha-Her2 derived light chain of the 10E8/Alpha-Her2 antibody—antiHer2-VLCH1 (SEQ ID NO:13):

DIVMTQSHKFMSTSVGDRVSITCKASQDVNTAVAWYQQKPGHSPKLLIYS

ASFRYTGVPDRFTGNRSGTDFTFTISSVQAEDLAVYYCQQHYTTPPTFGG

GTKVEIKSSASTKGPSVFPLAPSSKSTSGGTAALGCLVKDYFPEPVTVSW

NSGALTSGVHTFPAVLQSSGLYSLSSVVTVPSSSLGTQTYICNVNHKPSN

TKVDKKVEPKSC

Amino acid sequence defining the alpha-Her2 derived heavy chain of the 10E8/Alpha-Her2 antibody—antiHer2-HC-Hole-Cross (SEQ ID NO:14):

QVQLQQSGPELVKPGASLKLSCTASGFNIKDTYIHWVKQRPEQGLEWIGR

IYPTNGYTRYDPKFQDKATITADTSSNTAYLQVSRLTSEDTAVYYCSRWG

GDGFYAMDYWGQGASVTVSSASTAAPSVFIFPPSDEQLKSGTASVVCLLN

NFYPREAKVQWKVDNALQSGNSQESVTEQDSKDSTYSLSSTLTLSKADYE

KHKVYACEVTHQGLSSPVTKSFNRGECDKTHTCPPCPAPEFEGGPSVFLF

PPKPKDTLMISRTPEVTCVVVDVSHEDPEVKFNWYVDGVEVHNAKTKPRE

EQYNSTYRVVSVLTVLHQDWLNGKEYKCKVSNKALPASIEKTISKAKGQP

REPQVCTLPPSRDELTKNQVSLSCAVKGFYPSDIAVEWESNGQPENNYKT

TPPVLDSDGSFFLVSKLTVDKSRWQQGNVFSCSVLHEALHSHYTQKSLSL

SPGK

Amino acid sequence defining the 10E8 derived light chain of the 10E8/Alpha-Her2 antibody—10E8-LC (SEQ ID NO:9):

YELTQETGVSVALGRTVTITCRGDSLRSHYASWYQKKPGQAPILLFYGKN

NRPSGVPDRFSGSASGNRASLTISGAQAEDDAEYYCSSRDKSGSRLSVFG

GGTKLTVLSQPKAAPSVTLFPPSSEELQANKATLVCLISDFYPGAVTVAW

KADSSPVKAGVETTTPSKQSNNKYAASSYLSLTPEQWKSHRSYSCQVTHE

GSTVEKTVAPTECS

Amino acid sequence defining the 10E8 derived heavy chain of the 10E8/Alpha-Her2 antibody—10E8-HC-Knob (SEQ ID NO:10):

EVQLVESGGGLVKPGGSLRLSCSASGFDFDNAWMTWVRQPPGKGLEWVGR

ITGPGEGWSVDYAAPVEGRFTISRLNSINFLYLEMNNLRMEDSGLYFCAR

TGKYYDFWSGYPPGEEYFQDWGRGTLVTVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK

4E10/P140 antibody:
Amino acid sequence defining the Pro 140 derived light chain of the 4E10/P140 antibody—PRO140-VLCH1 (SEQ ID NO:11):

DIVMTQSPLSLPVTPGEPASISCRSSQRLLSSYGHTYLHWYLQKPGQSPQ

LLIYEVSNRFSGVPDRFSGSGSGTDFTLKISRVEAEDVGVYYCSQSTHVP

LTFGQGTKVEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the Pro 140 derived heavy chain of the 4E10/P140 antibody—PRO140-HC-Hole-Cross (SEQ ID NO:12):

EVQLVESGGGLVKPGGSLRLSCAASGYTFSNYWIGWVRQAPGKGLEWIGD

IYPGGNYIRNNEKFKDKTTLSADTSKNTAYLQMNSLKTEDTAVYYCGSSF

GSNYVFAWFTYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the 4E10 derived light chain of the 4E10/P140 antibody—4E10-LC (SEQ ID NO:17):

EIVLTQSPGTQSLSPGERATLSCRASQSVGNNKLAWYQQRPGQAPRLLIY

GASSRPSGVADRFSGSGSGTDFTLTISRLEPEDFAVYYCQQYGQSLSTFG

QGTKVEVKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Amino acid sequence defining the 4E10 derived heavy chain of the 4E10/P140 antibody—PGT145-HC-Knob (SEQ ID NO:18):

QVQLVQSGAEVKRPGSSVTVSCKASGGSFSTYALSWVRQAPGRGLEWMGG

VIPLLTITNYAPRFQGRITITADRSTSTAYLELNSLRPEDTAVYYCAREG

TTGAGWLGKPIGAFAHWGQGTLVTVSSASTKGPSVFPLAPSSKSTSGGTA

ALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPEFEGGPSV

FLFPPKPKDTLMISRTPEVTCVVVDVSHEDPEVKFNWYVDGVEVHNAKTK

PREEQYNSTYRVVSVLTVLHQDWLNGKEYKCKVSNKALPASIEKTISKAK

GQPREPQVYTLPPCRDELTKNQVSLWCLVKGFYPSDIAVEWESNGQPENN

YKTTPPVLDSDGSFFLYSKLTVDKSRWQQGNVFSCSVLHEALHSHYTQKS

LSLSPGK

10E8/X19 antibody:
Amino acid sequence defining the X19 derived light chain of the 10E8/X19 antibody—X19-VLCH1 (SEQ ID NO:19):

EIVLTQSPATLSVSPGRRATLSCRASQSVNTNLAWYQQKPGQAPRLLIYG

ASSRATGIPDRFSGSGSGTDFTLTISRLEPEDFAVYYCQHYGSSPLTFGG

GTKLEIKSSASTKGPSVFPLAPSSKSTSGGTAALGCLVKDYFPEPVTVSW

NSGALTSGVHTFPAVLQSSGLYSLSSVVTVPSSSLGTQTYICNVNHKPSN

TKVDKKVEPKSC

Amino acid sequence defining the X19 derived heavy chain of the 10E8/X19 antibody—X19-HC-Hole-Cross (SEQ ID NO:20):

QVQLVQSGGGVVQPGRSLRLSCAASGFTFSSYPMHWVRQAPGKGLEWMTV

ISSDGRNKYYPDSVKGRFTISRDNSKNTLYLQMNSLRPEDTAVYYCARGG

YHDFWSGPDYWGQGTLVTVSSASTAAPSVFIFPPSDEQLKSGTASVVCLL

NNFYPREAKVQWKVDNALQSGNSQESVTEQDSKDSTYSLSSTLTLSKADY

EKHKVYACEVTHQGLSSPVTKSFNRGECDKTHTCPPCPAPEFEGGPSVFL

FPPKPKDTLMISRTPEVTCVVVDVSHEDPEVKFNWYVDGVEVHNAKTKPR

EEQYNSTYRVVSVLTVLHQDWLNGKEYKCKVSNKALPASIEKTISKAKGQ

PREPQVCTLPPSRDELTKNQVSLSCAVKGFYPSDIAVEWESNGQPENNYK

TTPPVLDSDGSFFLVSKLTVDKSRWQQGNVFSCSVLHEALHSHYTQKSLS

LSPGK

Amino acid sequence defining the 10E8 derived light chain of the 10E8/X19 antibody—10E8-LC (SEQ ID NO:9):

YELTQETGVSVALGRTVTITCRGDSLRSHYASWYQKKPGQAPILLFYGKN

NRPSGVPDRFSGSASGNRASLTISGAQAEDDAEYYCSSRDKSGSRLSVFG

GGTKLTVLSQPKAAPSVTLFPPSSEELQANKATLVCLISDFYPGAVTVAW

KADSSPVKAGVETTTPSKQSNNKYAASSYLSLTPEQWKSHRSYSCQVTHE

GSTVEKTVAPTECS

Amino acid sequence defining the 10E8 derived heavy chain of the 10E8/X19 antibody—PGT145-HC-Knob (SEQ ID NO:10):

EVQLVESGGGLVKPGGSLRLSCSASGFDFDNAWMTWVRQPPGKGLEWVGR

ITGPGEGWSVDYAAPVEGRFTISRLNSINFLYLEMNNLRMEDSGLYFCAR

TGKYYDFWSGYPPGEEYFQDWGRGTLVTVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK

10E8/515H7 antibody
Amino acid sequence defining the 515H7 derived light chain of the 10E8/515H7 antibody—515H7-VLCH1 (SEQ ID NO:25):

DIVMSQSPSSLAVSAGEKVTMSCKSSQSLFNSRTRKNYLAWYQQKPGQSP

KLLIYWASARDSGVPARFTGSGSETYFTLTISRVQAEDLAVYYCMQSFNL

RTFGGGTKLEIKASTKGPSVFPLAPSSKSTSGGTAALGCLVKDYFPEPVT

VSWNSGALTSGVHTFPAVLQSSGLYSLSSVVTVPSSSLGTQTYICNVNHK

PSNTKVDKKVEPKSC

Amino acid sequence defining the 515H7 derived heavy chain of the 10E8/515H7 antibody—515H7-Hole-Cross (SEQ ID NO:26):

EVNLVESGGGLVQPGGSLRLSCATSGFTFTDNYMSWVRQPPGKALEWLGF

IRNKANGYTTDYSASVRGRFTISRDNSQSILYLQMNALRAEDSATYYCAR

DVGSNYFDYWGQGTTLTVSSASTAAPSVFIFPPSDEQLKSGTASVVCLLN

NFYPREAKVQWKVDNALQSGNSQESVTEQDSKDSTYSLSSTLTLSKADYE

KHKVYACEVTHQGLSSPVTKSFNRGECDKTHTCPPCPAPEFEGGPSVFLF

PPKPKDTLMISRTPEVTCVVVDVSHEDPEVKFNWYVDGVEVHNAKTKPRE

EQYNSTYRVVSVLTVLHQDWLNGKEYKCKVSNKALPASIEKTISKAKGQP

REPQVCTLPPSRDELTKNQVSLSCAVKGFYPSDIAVEWESNGQPENNYKT

TPPVLDSDGSFFLVSKLTVDKSRWQQGNVFSCSVLHEALHSHYTQKSLSL

SPGK

Amino acid sequence defining the 10E8 derived light chain of the 10E8/515H7 antibody—10E8-LC (SEQ ID NO:9):

YELTQETGVSVALGRTVTITCRGDSLRSHYASWYQKKPGQAPILLFYGKN

NRPSGVPDRFSGSASGNRASLTISGAQAEDDAEYYCSSRDKSGSRLSVFG

GGTKLTVLSQPKAAPSVTLFPPSSEELQANKATLVCLISDFYPGAVTVAW

KADSSPVKAGVETTTPSKQSNNKYAASSYLSLTPEQWKSHRSYSCQVTHE

GSTVEKTVAPTECS

Amino acid sequence defining the 10E8 derived heavy chain of the 10E8/515H7 antibody—10E8-HC-Knob (SEQ ID NO:10):

```
EVQLVESGGGLVKPGGSLRLSCSASGFDFDNAWMTWVRQPPGKGLEWVGR

ITGPGEGWSVDYAAPVEGRFTISRLNSINFLYLEMNNLRMEDSGLYFCAR

TGKYYDFWSGYPPGEEYFQDWGRGTLVTVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK
```

Chimeric CDR123 antibody (SEQ ID NO:27):

```
SELTQDPAVSVALGQTVRITCRGDSLRSHYASWYQQKPGQAPVLVIYGKN

NRPSGIPDRFSGSSSGNTASLTITGAQAEDEADYYCSSRDKSGSRLSVFG

GGTKLTVLSQPKAAPSVTLFPPSSEELQANKATLVCLISDFYPGAVTVAW

KADSSPVKAGVETTTPSKQSNNKYAASSYLSLTPEQWKSHRSYSCQVTHE

GSTVEKTVAPTECS
```

Chimeric FW123 (SEQ ID NO:28):

```
YELTQETGVSVALGRTVTITCQGDSLRSYYASWYQKKPGQAPILLFYGKN

NRPSGVPDRFSGSASGNRASLTISGAQAEDDAEYYCNSRDSSGNHLVVFG

GGTKLTVLSQPKAAPSVTLFPPSSEELQANKATLVCLISDFYPGAVTVAW

KADSSPVKAGVETTTPSKQSNNKYAASSYLSLTPEQWKSHRSYSCQVTHE

GSTVEKTVAPTECS
```

10E8V1.0/iMab antibody

Amino acid sequence defining the MV1 derived light chain of the 10E8v1.0/MV1 antibody MV1-VLCH1 (SEQ ID NO:1):

```
DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC
```

Amino acid sequence defining the MV1 derived heavy chain of the 10E8v1.0/MV1 antibody MV1-HC-Hole-Cross (SEQ ID NO:2):

```
QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK
```

Amino acid sequence defining the 10E8v1.0 derived light chain of the 10E8v1.0/iMab antibody—10E8v1.0-LC (SEQ ID NO:29):

```
ASELTQDPAVSVALKQTVTITCRGDSLRSHYVSWYQKKPGQAPVLVFYGK

NNRPSGIPDRFSGSSSGNTASLTIAGAQAEDDADYYCSSRDKSGSRLSVF

GGGTKLTVLSQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS
```

Amino acid sequence defining the 10E8v1.0 derived heavy chain of the 10E8v1.0/iMab antibody—10E8v1.0-HC-Knob (SEQ ID NO:30):

```
EVRLVESGGGLVKPGGSLRLSCSASGFNFDDAWMTWVRQPPGKGLEWVGR

ISGPGEGWSVDYAESVKGRFTISRLNSINFLYLEMNNVRTEDTGYYFCAR

TGKHYDFWSGYPPGEEYFQDWGQGTLVIVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK
```

10E8V1.1/iMab antibody

Amino acid sequence defining the MV1 derived light chain of the 10E8v1.1/iMab antibody MV1-VLCH1 (SEQ ID NO:1):

```
DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC
```

Amino acid sequence defining the MV1 derived heavy chain of the 10E8v1.1/iMab antibody MV1-HC-Hole-Cross (SEQ ID NO:2):

```
QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD
```

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the 10E8v1.1 derived light chain of the 10E8v1.1/iMab antibody—10E8v1.1-LC (SEQ ID NO:31):

ASELTQDPAVSVALKQTVTITCRGDSLRSHYVSWYQKKPGQAPVLVFYGK

NNRPSGIPDRFSGSSSGNTASLTIAGAQAEDDADYYCSSRDKSGSRLSVF

GGGTKLTVLSQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS

Amino acid sequence defining the 10E8v1.1 derived heavy chain of the 10E8v1.1/iMab antibody—10E8v1.1 HC-Knob (SEQ ID NO:32):

EVRLVESGGGLVKPGGSLRLSCSASGFNFDDAWMTWVRQPPGKGLEWVGR

ISGPGEGWSVDYAESVKGRFTISRLNSINFLYLEMNNVRTEDTGYYFCAR

TGKYYDFWSGYPPGEEYFQDWGQGTLVIVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK

10E8V2.0/iMab antibody (also referred to as 10E8.2/iMab antibody)

Amino acid sequence defining the MV1 derived light chain of the 10E8v2.0/iMab antibody MV1-VLCH1 (SEQ ID NO:1):

DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the MV1 derived heavy chain of the 10E8v2.0/iMab antibody MV1-HC-Hole-Cross (SEQ ID NO:2):

QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the 10E8v2.0 derived light chain of the 10E8v2.0/iMab antibody—10E8v2.0-LC (SEQ ID NO:33):

ASELTQDPAVSVALKQTVTITCRGDSLRSHYASWYQKKPGQAPILLFYGK

NNRPSGVPDRFSGSASGNRASLTISGAQAEDDAEYYCSSRDKSGSRLSVF

GGGTKLTVLSQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS

Amino acid sequence defining the 10E8v2.0 derived heavy chain of the 10E8v2.0/iMab antibody—10E8v2.0-HC-Knob (SEQ ID NO:34):

EVRLVESGGGLVKPGGSLRLSCSASGFNFDDAWMTWVRQPPGKGLEWVGR

ISGPGEGWSVDYAESVKGRFTISRLNSINFLYLEMNNVRTEDTGYYFCAR

TGKYHDFWSGYPPGEEYFQDWGQGTLVIVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK

10E8V3.0/iMab antibody

Amino acid sequence defining the MV1 derived light chain of the 10E8v3.0/iMab antibody MV1-VLCH1 (SEQ ID NO:1):

DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the MV1 derived heavy chain of the 10E8v3.0/iMab antibody MV1-HC-Hole-Cross (SEQ ID NO:2):

QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the 10E8v3.0 derived light chain of the 10E8v3.0/iMab antibody—10E8v3.0-LC (SEQ ID NO:15):

SELTQETGVSVALGRTVTITCRGDSLRSHYASWYQKKPGQAPILLFYGKN

NRPSGIHDRFSGSASGNRASLTISGAQAEDDAEYYCSSRDKSGSRLSVFG

GGTKLTVLSQPKAAPSVTLFPPSSEELQANKATLVCLISDFYPGAVTVAW

KADSSPVKAGVETTTPSKQSNNKYAASSYLSLTPEQWKSHRSYSCQVTHE

GSTVEKTVAPTECS

Amino acid sequence defining the 10E8v3.0 derived heavy chain of the 10E8v3.0/iMab antibody—10E8v3.0-HC-Knob (SEQ ID NO:16):

EVQLVESGGDLVKPGGSLRLSCSASGFSFKNTWMTWVRQAPGKGLEWVGR

ITGPGEGWTSDYAATVQGRFTISRNNMIDMLYLEMNRLRTDDTGLYYCVH

TEKYYNFWGGYPPGEEYFQHWGRGTLVIVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK

10E8V1.0/P140 (H6L10/PRO140) antibody

Amino acid sequence defining the PRO140 derived light chain of the 10E8V1.0/P140 antibody—PRO140-VLCH1 (SEQ ID NO:11):

DIVMTQSPLSLPVTPGEPASISCRSSQRLLSSYGHTYLHWYLQKPGQSPQ

LLIYEVSNRFSGVPDRFSGSGSGTDFTLKISRVEAEDVGVYYCSQSTHVP

LTFGQGTKVEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the PRO140 derived heavy chain of the 10E8V1.0/P140 antibody—PRO140-Hole-Cross (SEQ ID NO:12):

EVQLVESGGGLVKPGGSLRLSCAASGYTFSNYWIGWVRQAPGKGLEWIGD

IYPGGNYIRNNEKFKDKTTLSADTSKNTAYLQMNSLKTEDTAVYYCGSSF

GSNYVFAWFTYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the L10 derived light chain of the 10E8V1.0/P140 antibody—L10-LC (SEQ ID NO:29):

ASELTQDPAVSVALKQTVTITCRGDSLRSHYVSWYQKKPGQAPVLVFYGK

NNRPSGIPDRFSGSSSGNTASLTIAGAQAEDDADYYCSSRDKSGSRLSVF

GGGTKLTVLSQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS

Amino acid sequence defining the H6 derived heavy chain of the 10E8V1.0/P140 antibody—H6-HC-Knob (SEQ ID NO:30):

EVRLVESGGGLVKPGGSLRLSCSASGFNFDDAWMTWVRQPPGKGLEWVGR

ISGPGEGWSVDYAESVKGRFTISRLNSINFLYLEMNNVRTEDTGYYFCAR

TGKHYDFWSGYPPGEEYFQDWGQGTLVIVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK

10E8V1.1/P140 antibody

Amino acid sequence defining the PRO140 derived light chain of the 10E8v1.1/P140 antibody PRO140-VLCH1 (SEQ ID NO:11):

DIVMTQSPLSLPVTPGEPASISCRSSQRLLSSYGHTYLHWYLQKPGQSPQ

LLIYEVSNRFSGVPDRFSGSGSGTDFTLKISRVEAEDVGVYYCSQSTHVP

LTFGQGTKVEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the P140 derived heavy chain of the 10E8v1.1/P140 antibody PRO140-HC-Hole-Cross (SEQ ID NO:12):

```
EVQLVESGGGLVKPGGSLRLSCAASGYTFSNYWIGWVRQAPGKGLEWIGD

IYPGGNYIRNNEKFKDKTTLSADTSKNTAYLQMNSLKTEDTAVYYCGSSF

GSNYVFAWFTYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK
```

Amino acid sequence defining the 10E8v1.1 derived light chain of the 10E8v1.1/P140 antibody—10E8v1.1-LC (SEQ ID NO:31):

```
ASELTQDPAVSVALKQTVTITCRGDSLRSHYVSWYQKKPGQAPVLVFYGK

NNRPSGIPDRFSGSSSGNTASLTIAGAQAEDDADYYCSSRDKSGSRLSVF

GGGTKLTVLSQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS
```

Amino acid sequence defining the 10E8v1.1 derived heavy chain of the 10E8v1.1/P140 antibody—10E8v1.1 HC-Knob (SEQ ID NO:32):

```
EVRLVESGGGLVKPGGSLRLSCSASGFNFDDAWMTWVRQPPGKGLEWVGR

ISGPGEGWSVDYAESVKGRFTISRLNSINFLYLEMNNVRTEDTGYYFCAR

TGKYYDFWSGYPPGEEYFQDWGQGTLVIVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK
```

10E8V2.0/P140 antibody

Amino acid sequence defining the PRO140 derived light chain of the 10E8v2.0/P140 antibody PRO140-VLCH1 (SEQ ID NO:11):

```
DIVMTQSPLSLPVTPGEPASISCRSSQRLLSSYGHTYLHWYLQKPGQSPQ

LLIYEVSNRFSGVPDRFSGSGSGTDFTLKISRVEAEDVGVYYCSQSTHVP

LTFGQGTKVEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC
```

Amino acid sequence defining the P140 derived heavy chain of the 10E8v2.0/P140 antibody PRO140-HC-Hole-Cross (SEQ ID NO:12):

```
EVQLVESGGGLVKPGGSLRLSCAASGYTFSNYWIGWVRQAPGKGLEWIGD

IYPGGNYIRNNEKFKDKTTLSADTSKNTAYLQMNSLKTEDTAVYYCGSSF

GSNYVFAWFTYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK
```

Amino acid sequence defining the 10E8v2.0 derived light chain of the 10E8v2.0/P140 antibody—10E8v2.0-LC (SEQ ID NO:33):

```
ASELTQDPAVSVALKQTVTITCRGDSLRSHYASWYQKKPGQAPILLFYGK

NNRPSGVPDRFSGSASGNRASLTISGAQAEDDAEYYCSSRDKSGSRLSVF

GGGTKLTVLSQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS
```

Amino acid sequence defining the 10E8v2.0 derived heavy chain of the 10E8v2.0/P140 antibody—10E8v2.0 HC-Knob (SEQ ID NO:34):

```
EVRLVESGGGLVKPGGSLRLSCSASGFNFDDAWMTWVRQPPGKGLEWVGR

ISGPGEGWSVDYAESVKGRFTISRLNSINFLYLEMNNVRTEDTGYYFCAR

TGKHYDFWSGYPPGEEYFQDWGQGTLVIVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK
```

10E8V3.0/P140 antibody

Amino acid sequence defining the PRO140 derived light chain of the 10E8v3.0/P140 antibody PRO140-VLCH1 (SEQ ID NO:11):

```
DIVMTQSPLSLPVTPGEPASISCRSSQRLLSSYGHTYLHWYLQKPGQSPQ

LLIYEVSNRFSGVPDRFSGSGSGTDFTLKISRVEAEDVGVYYCSQSTHVP

LTFGQGTKVEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC
```

Amino acid sequence defining the P140 derived heavy chain of the 10E8v3.0/P140 antibody PRO140-HC-Hole-Cross (SEQ ID NO:12):

```
EVQLVESGGGLVKPGGSLRLSCAASGYTFSNYWIGWVRQAPGKGLEWIGD

IYPGGNYIRNNEKFKDKTTLSADTSKNTAYLQMNSLKTEDTAVYYCGSSF

GSNYVFAWFTYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK
```

Amino acid sequence defining the 10E8v3.0 derived light chain of the 10E8v3.0/P140 antibody—10E8v3.0-LC (SEQ ID NO:15):

```
SELTQETGVSVALGRTVTITCRGDSLRSHYASWYQKKPGQAPILLFYGKN

NRPSGIHDRFSGSASGNRASLTISGAQAEDDAEYYCSSRDKSGSRLSVFG

GGTKLTVLSQPKAAPSVTLFPPSSEELQANKATLVCLISDFYPGAVTVAW

KADSSPVKAGVETTTPSKQSNNKYAASSYLSLTPEQWKSHRSYSCQVTHE

GSTVEKTVAPTECS
```

Amino acid sequence defining the 10E8v3.0 derived heavy chain of the 10E8v3.0/P140 antibody—10E8v3.0 HC-Knob (SEQ ID NO:16):

```
EVQLVESGGDLVKPGGSLRLSCSASGFSFKNTWMTWVRQAPGKGLEWVGR

ITGPGEGWTSDYAATVQGRFTISRNNMIDMLYLEMNRLRTDDTGLYYCVH

TEKYYNFWGGYPPGEEYFQHWGRGTLVIVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK
```

10E8.2.1/iMab
Amino acid sequence defining the MV1 derived light chain of the 10E8.2/iMab antibody MV1-VLCH1 (SEQ ID NO: 1)

```
DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC
```

Amino acid sequence defining the MV1 derived heavy chain of the 10E8.2/iMab antibody MV1-HC-Hole-Cross (SEQ ID NO: 2)

```
QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK
```

Amino acid sequence defining the 10E8.2 derived light chain of the 10E8.2/iMab antibody—10E8.2-LC (SEQ ID NO: 33)

```
ASELTQDPAVSVALKQTVTITCRGDSLRSHYASWYQKKPGQAPILLFYGK

NNRPSGVPDRFSGSASGNRASLTISGAQAEDDAEYYCSSRDKSGSRLSVF

GGGTKLTVLSQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS
```

Amino acid sequence defining the 10E8.2.1 derived heavy chain of the 10E8.2.1/iMab antibody—10E8.2.1-HC-Knob (SEQ ID NO:35)

```
EVRLVESGGGLVKPGGSLRLSCSASGFNFDDAWMTWVRQPPGKGLEWVGR

ISGPGEGWSVDYAESVKGRFTISRDNTKNTLYLEMNNVRTEDTGYYFCAR

TGKHYDFWSGYPPGEEYFQDWGQGTLVIVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK
```

10E8.2.2/iMab
Amino acid sequence defining the MV1 derived light chain of the 10E8.2/iMab antibody MV1-VLCH1 (SEQ ID NO: 1)

```
DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC
```

Amino acid sequence defining the MV1 derived heavy chain of the 10E8.2/iMab antibody MV1-HC-Hole-Cross (SEQ ID NO: 2)

```
QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK
```

Amino acid sequence defining the 10E8.2 derived light chain of the 10E8.2/iMab antibody—10E8.2-LC (SEQ ID NO: 33)

```
ASELTQDPAVSVALKQTVTITCRGDSLRSHYASWYQKKPGQAPILLFYGK

NNRPSGVPDRFSGSASGNRASLTISGAQAEDDAEYYCSSRDKSGSRLSVF

GGGTKLTVLSQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS
```

Amino acid sequence defining the 10E8.2.2 derived heavy chain of the 10E8.2.2/iMab antibody—10E8.2.2-HC-Knob (SEQ ID NO:36)

```
EVRLVESGGGLVKPGGSLRLSCSASGFNFDDAWMTWVRQPPGKGLEWVGR

ISGPGEGWSVDYAESVKGRFTISRLNSINFLYLEMNNVRTEDTGYYFCAR

TGKHYDFWSGYPPGEEYFQDWGQGTKVIVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK
```

10E8.2.3/iMab
Amino acid sequence defining the MV1 derived light chain of the 10E8.2/iMab antibody MV1-VLCH1 (SEQ ID NO: 1)

```
DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC
```

Amino acid sequence defining the MV1 derived heavy chain of the 10E8.2/iMab antibody MV1-HC-Hole-Cross (SEQ ID NO: 2)

```
QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK
```

Amino acid sequence defining the 10E8.2 derived light chain of the 10E8.2/iMab antibody—10E8.2-LC (SEQ ID NO: 33)

```
ASELTQDPAVSVALKQTVTITCRGDSLRSHYASWYQKKPGQAPILLFYGK

NNRPSGVPDRFSGSASGNRASLTISGAQAEDDAEYYCSSRDKSGSRLSVF

GGGTKLTVLSQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS
```

Amino acid sequence defining the 10E8.2.3 derived heavy chain of the 10E8.2.3/iMab antibody—10E8.2.3-HC-Knob (SEQ ID NO:37)

```
EVRLVESGGGLVKPGGSLRLSCSASGFNFDDAWMTWVRQPPGKGLEWVGR

ISGPGEGWSVDYAESVKGRFTISRDNTKNTLYLEMNNVRTEDTGYYFCAR

TGKHYDFWSGYPPGEEYFQDWGQGTKVIVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK
```

10E8.2.4/iMab
Amino acid sequence defining the MV1 derived light chain of the 10E8.2.4/iMab antibody MV1-VLCH1-LM52 (SEQ ID NO:38)

```
DIVMTQSPDSLAVSLGERVTMNCKSSQSLLYSTNQKNYLAWYQQKPGQSP

KLLIYWANSTESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC
```

Amino acid sequence defining the MV1 derived heavy chain of the 10E8.2/iMab antibody MV1-HC-Hole-Cross (SEQ ID NO: 2)

QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the 10E8.2 derived light chain of the 10E8.2/iMab antibody—10E8.2-LC (SEQ ID NO: 33)

ASELTQDPAVSVALKQTVTITCRGDSLRSHYASWYQKKPGQAPILLFYGK

NNRPSGVPDRFSGSASGNRASLTISGAQAEDDAEYYCSSRDKSGSRLSVF

GGGTKLTVLSQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS

Amino acid sequence defining the 10E8.2.3 derived heavy chain of the 10E8.2.3/iMab antibody—10E8.2.3-HC-Knob (SEQ ID NO:39)

EVRLVESGGGLVKPGGSLRLSCSASGFNFDDAWMTWVRQPPGKGLEWVGR

ISGPGEGWSVDYAESVKGRFTISRDNTKNTLYLEMNNVRTEDTGYYFCAR

TGKHYDFWSGYPPGEEYFQDWGQGTKVIVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK

10E8.2.5/iMab
Amino acid sequence defining the MV1 derived light chain of the 10E8.2/iMab antibody MV1-VLCH1 (SEQ ID NO: 1)

DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the MV1 derived heavy chain of the 10E8.2/iMab antibody MV1-HC-Hole-Cross (SEQ ID NO: 2)

QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the 10E8.2 derived light chain of the 10E8.2/iMab antibody—10E8.2-LC (SEQ ID NO: 33)

ASELTQDPAVSVALKQTVTITCRGDSLRSHYASWYQKKPGQAPILLFYGK

NNRPSGVPDRFSGSASGNRASLTISGAQAEDDAEYYCSSRDKSGSRLSVF

GGGTKLTVLSQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS

Amino acid sequence defining the 10E8.2.5 derived heavy chain of the 10E8.2.5/iMab antibody—10E8.2.5-HC-Knob (SEQ ID NO:40)

EVRLVESGGGLVKPGGSLRLSCSASGFNFDDAWMTWVRQPPGKGLEWVGR

ISGPGEGWSVDYAESVKGRFTISRKNSINTLYLEMNNVRTEDTGYYFCAR

TGKHYDFWSGYPPGEEYFQDWGQGTKVIVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK

10E8.2.6/iMab
Amino acid sequence defining the MV1 derived light chain of the 10E8.2/iMab antibody MV1-VLCH1 (SEQ ID NO: 1)

DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the MV1 derived heavy chain of the 10E8.2/iMab antibody MV1-HC-Hole-Cross (SEQ ID NO: 2)

QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the 10E8.2 derived light chain of the 10E8.2/iMab antibody—10E8.2-LC (SEQ ID NO: 33)

ASELTQDPAVSVALKQTVTITCRGDSLRSHYASWYQKKPGQAPILLFYGK

NNRPSGVPDRFSGSASGNRASLTISGAQAEDDAEYYCSSRDKSGSRLSVF

GGGTKLTVLSQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS

Amino acid sequence defining the 10E8.2.6 derived heavy chain of the 10E8.2.6/iMab antibody—10E8.2.6-HC-Knob (SEQ ID NO:41)

EVRLVESGGGLVKPGGSLRLSCSASGFNFDDAWMTWVRQPPGKGLEWVGR

ISGPGEGWSVDYAESVKGRFTISRDNSINTLYLEMNNVRTEDTGYYFCAR

TGKHYDFWSGYPPGEEYFQDWGQGTKVIVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK

10E8.2.7/iMab

Amino acid sequence defining the MV1 derived light chain of the 10E8.2/iMab antibody MV1-VLCH1 (SEQ ID NO: 1)

DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the MV1 derived heavy chain of the 10E8.2/iMab antibody MV1-HC-Hole-Cross (SEQ ID NO: 2)

QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK

Amino acid sequence defining the 10E8.2 derived light chain of the 10E8.2/iMab antibody—10E8.2-LC (SEQ ID NO: 33)

ASELTQDPAVSVALKQTVTITCRGDSLRSHYASWYQKKPGQAPILLFYGK

NNRPSGVPDRFSGSASGNRASLTISGAQAEDDAEYYCSSRDKSGSRLSVF

GGGTKLTVLSQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS

Amino acid sequence defining the 10E8.4 derived heavy chain of the 10E8.4/iMab antibody—10E8.4-HC-Knob (SEQ ID NO:42)

EVRLVESGGGLVKPGGSLRLSCSASGFNFDDAWMTWVRQPPGKGLEWVGR

ISGPGEGWSVDYAESVKGRFTISRKNSKNTLYLEMNNVRTEDTGYYFCAR

TGKHYDFWSGYPPGEEYFQDWGQGTKVIVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK

10E8.2.8/iMab

Amino acid sequence defining the MV1 derived light chain of the 10E8.2/iMab antibody MV1-VLCH1 (SEQ ID NO: 1)

DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC

Amino acid sequence defining the MV1 derived heavy chain of the 10E8.2/iMab antibody MV1-HC-Hole-Cross (SEQ ID NO: 2)

```
QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK
```

Amino acid sequence defining the 10E8.2 derived light chain of the 10E8.2/iMab antibody—10E8.2-LC (SEQ ID NO: 33)

```
ASELTQDPAVSVALKQTVTITCRGDSLRSHYASWYQKKPGQAPILLFYGK

NNRPSGVPDRFSGSASGNRASLTISGAQAEDDAEYYCSSRDKSGSRLSVF

GGGTKLTVLSQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS
```

Amino acid sequence defining the 10E8.2.8 derived heavy chain of the 10E8.2.8/iMab antibody—10E8.2.8-HC-Knob (SEQ ID NO:43)

```
EVRLVESGGGLVKPGGSLRLSCSASGFNFDDAWMTWVRQPPGKGLEWVGR

ISGPGEGWSVDYAESVKGRFTISRDNSKNTLYLEMNNVRTEDTGYYFCAR

TGKHYDFWSGYPPGEEYFQDWGQGTKVIVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK
```

10E8.2.10/iMab

Amino acid sequence defining the MV1 derived light chain of the 10E8.2/iMab antibody MV1-VLCH1 (SEQ ID NO: 1)

```
DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC
```

Amino acid sequence defining the MV1 derived heavy chain of the 10E8.2/iMab antibody MV1-HC-Hole-Cross (SEQ ID NO: 2)

```
QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK
```

Amino acid sequence defining the 10E8.4 derived light chain of the 10E8.4/iMab antibody—10E8.4-LC (SEQ ID NO:44)

```
ASELTQDPAVSVALKQTVTITCRGDSLRSHYASWYQKKTGQAPKLLFYGK

NNRPSGVPDRFSGSASGNRASLTISGAQAEDDAEYYCSSRDKSGSRLSVF

GGGTKLTVLSQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS
```

Amino acid sequence defining the 10E8.2.8 derived heavy chain of the 10E8.2.8/iMab antibody—10E8.2.8-HC-Knob (SEQ ID NO:45)

```
EVRLVESGGGLVKPGGSLRLSCSASGFNFDDAWMTWVRQPPGKGLEWVGR

ISGPGEGWSVDYAESVKGRFTISRDNSKNTLYLEMNNVRTEDTGYYFCAR

TGKHYDFWSGYPPGEEYFQDWGQGTKVIVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK
```

10E8.4/iMab

Amino acid sequence defining the MV1 derived light chain of the 10E8.2/iMab antibody MV1-VLCH1 (SEQ ID NO: 1)

```
DIVMTQSPDSLAVSLGERVTMNCKSSQSLLYSTNQKNYLAWYQQKPGQSP

KLLIYWASTRESGVPDRFSGSGSGTDFTLTISSVQAEDVAVYYCQQYYSY

RTFGGGTKLEIKSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSC
```

Amino acid sequence defining the MV1 derived heavy chain of the 10E8.2/iMab antibody MV1-HC-Hole-Cross (SEQ ID NO: 2)

```
QVQLQQSGPEVVKPGASVKMSCKASGYTFTSYVIHWVRQKPGQGLDWIGY

INPYNDGTDYDEKFKGKATLTSDTSTSTAYMELSSLRSEDTAVYYCAREK

DNYATGAWFAYWGQGTLVTVSSASTAAPSVFIFPPSDEQLKSGTASVVCL

LNNFYPREAKVQWKVDNALQSGNSQESVTEQDSKDSTYSLSSTLTLSKAD

YEKHKVYACEVTHQGLSSPVTKSFNRGECDKTHTCPPCPAPEFEGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPASIEKTISKAKG

QPREPQVCTLPPSRDELTKNQVSLSCAVKGFYPSDIAVEWESNGQPENNY

KTTPPVLDSDGSFFLVSKLTVDKSRWQQGNVFSCSVLHEALHSHYTQKSL

SLSPGK
```

Amino acid sequence defining the 10E8.4 derived light chain of the 10E8.4/iMab antibody—10E8.4-LC (SEQ ID NO:46)

```
ASELTQDPAVSVALKQTVTITCRGDSLRSHYASWYQKKTGQAPKLLFYGK

NNRPSGVPDRFSGSASGNRASLTISGAQAEDDAEYYCSSRDKSGSRLSVF

GGGTKLTVLSQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS
```

Amino acid sequence defining the 10E8.4 derived heavy chain of the 10E8.4/iMab antibody—10E8.4-HC-Knob (SEQ ID NO:47)

```
EVRLVESGGGLVKPGGSLRLSCSASGFNFDDAWMTWVRQPPGKGLEWVGR

ISGPGEGWSVDYAESVKGRFTISRKNSKNTLYLEMNNVRTEDTGYYFCAR

TGKHYDFWSGYPPGEEYFQDWGQGTKVIVSSASTKGPSVFPLAPSSKSTS

GGTAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEFEG

GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPASIEKTI

SKAKGQPREPQVYTLPPCRDELTKNQVSLWCLVKGFYPSDIAVEWESNGQ

PENNYKTTPPVLDSDGSFFLYSKLTVDKSRWQQGNVFSCSVLHEALHSHY

TQKSLSLSPGK
```

In various embodiments, at least one of the heavy chain and/or light chain sequences derived from the PGT145, PG9, PGT128, PGT121, 10-1074, 3BNC117, VRC01, PGT151, 4E10, 10E8, P140, iMab (or the MV1 variant), 515H7 antibodies and variants thereof are paired together to form a bispecific antibody (e.g., a HIV CrossMab antibody). In an exemplary embodiment, at least one of the disclosed heavy and light chains selected from SEQ ID NOs: 1-36 are paired together to form a bispecific antibody (e.g., a HIV CrossMab antibody).

In various embodiments, the amino acid sequence of the bispecific antibody (e.g., HIV CrossMab antibody) further includes an amino acid analog, an amino acid derivative, or other non-classical amino acids.

In various embodiments, the bispecific antibody (e.g., HIV CrossMab antibody) comprises a sequence that is at least 60% identical to a wild-type heavy or light chain sequence of the PGT145, PG9, PGT128, PGT121, 10-1074, 3BNC117, VRC01, PGT151, 4E10, or 10E8 antibody. In various embodiments, the bispecific antibody (e.g., HIV CrossMab antibody) comprises a sequence that is at least 60% identical to a wild-type heavy chain or light chain sequence of the P140, iMab (or the MV1 variant), or 515H7 antibody. In exemplary embodiments, the bispecific antibody (e.g., HIV CrossMab antibody) comprises a sequence that is at least 60% identical to any of the sequences disclosed herein.

In various embodiments, the bispecific antibody (e.g., HIV CrossMab antibody) may comprise a sequence that is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to a wild-type heavy chain or light chain sequence of the PGT145, PG9, PGT128, PGT121, 10-1074, 3BNC117, VRC01, PGT151, 4E10, or 10E8 antibody.

In various embodiments, the bispecific antibody (e.g., HIV CrossMab antibody) may comprise a sequence that is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to a wild-type heavy chain or light chain sequence of the P140, iMab (or the MV1 variant), or 515H7 antibody.

In exemplary embodiments, the bispecific antibody (e.g., HIV CrossMab antibody) may comprise a sequence that is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to any of the sequences disclosed herein.

Homology or identity may be determined in various ways that are within the skill in the art, for instance, using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) PROC. NATL. ACAD. SCI. USA 87, 2264-2268; Altschul, (1993) J. MOL. EVOL. 36, 290-300; Altschul et al., (1997) NUCLEIC ACIDS RES. 25, 3389-3402, incorporated by reference) are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases see Altschul et al., (1994) NATURE GENETICS 6, 119-129 which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) PROC. NATL. ACAD. SCI. USA 89, 10915-10919, fully incorporated by reference). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: -G, Cost to open gap [Integer]: default=5 for nucleotides/11 for proteins; -E, Cost to extend gap [Integer]: default=2 for nucleotides/1 for proteins; -q, Penalty for nucleotide mismatch [Integer]: default=−3; -r, reward for nucleotide match [Integer]: default=1; -e, expect value [Real]: default=10; —W, wordsize [Integer]: default=11 for nucleotides/28 for megablast/3 for proteins; -y, Dropoff (X) for blast extensions in bits: default=20 for blastn/7 for others; -X, X dropoff value for gapped alignment (in bits): default=15 for all programs, not applicable to blastn; and -Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In various embodiments, the bispecific antibody (e.g., HIV CrossMab antibody) comprises a sequence that includes at least one amino acid alteration with respect to a wild-type heavy or light chain sequence of the PGT145, PG9, PGT128, PGT121, 10-1074, 3BNC117, VRC01, PGT151, 4E10, or 10E8 antibody. In various embodiments, the bispecific antibody (e.g., HIV CrossMab antibody) comprises a sequence that includes at least one amino acid alteration with respect to a wild-type heavy or light chain sequence of the P140, iMab (or the MV1 variant), 515H7 antibody. In exemplary embodiments, the bispecific antibody (e.g., HIV CrossMab antibody) comprises a sequence that includes at least one amino acid alteration with respect to any of the sequences disclosed herein.

In various embodiments, the bispecific antibody (e.g., HIV CrossMab antibody) comprises a sequence that includes at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 40, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acid alterations with respect to a wild-type heavy or light chain sequence of the PGT145, PG9, PGT128, PGT121, 10-1074, 3BNC117, VRC01, PGT151, 4E10, or 10E8 antibody.

In various embodiments, the bispecific antibody (e.g., HIV CrossMab antibody) comprises a sequence that includes at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 40, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acid alterations with respect to a wild-type heavy or light chain sequence of the P140, iMab (or the MV1 variant), or 515H7 antibody.

In exemplary embodiments, the bispecific antibody (e.g., HIV CrossMab antibody) comprises a sequence that includes at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 40, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acid alterations with respect to any of the sequences disclosed herein.

The amino acid alteration can be an amino acid deletion, insertion, substitution, or modification. In one embodiment, the amino acid alteration is an amino acid deletion. In another embodiment, the amino acid alteration is an amino acid substitution.

In various embodiments, the amino acid alteration may be in the Complementarity Determining Regions (CDRs) of the bispecific antibody (e.g., the CDR1, CDR2 or CDR3 regions). In another embodiment, the amino acid alteration may be in the framework regions (FWs) of the bispecific antibody (e.g., the FW1, FW2, FW3, or FW4 regions). In a further embodiment, the amino acid alteration may be in the joining regions (J regions) of the bispecific antibody (e.g., the J1, J2, J3, J4, J5, J6, or J7 regions).

Also provided herein are chimeric antibody derivatives of the bispecific antibodies, i.e., antibody molecules in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. For example, the bispecific antibody may include a heavy and/or light chain in which one or more CDRs or FWs derived from an antibody selected from a PGT145, PG9, PGT128, PGT121, 10-1074, 3BNC117, VRC01, PGT151, 4E10, 10E8, P140, iMab (or the MV1 variant), or 515H7 antibody are replaced with one or more CDRs or FWs derived from a different antibody selected from a PGT145, PG9, PGT128, PGT121, 10-1074, 3BNC117, VRC01, PGT151, 4E10, 10E8, P140, iMab (or the MV1 variant), or 515H7 antibody.

In various embodiments, the present invention provides improved bispecific antibodies that demonstrate advantageous properties related to solubility, stability, and therapeutic activity. It is contemplated that such antibodies may be particularly suited for large-scale commercial production. For example, such antibodies may exhibit increased solubility, reduced aggregation, reduced precipitation, and/or enhanced stability or resistance to degradation during manufacturing.

In an exemplary embodiment, the improved bispecific antibody is a variant of the 10E8V2.0/iMab antibody (also referred to as 10E8.2/iMab antibody). In such embodiments, the variant may exhibit enhanced solubility, stability, and/or therapeutic activity (e.g., antiviral activity) compared to the parent 10E8V2.0/iMab antibody.

In some embodiments, the bispecific antibody (e.g., HIV CrossMab antibody) may comprise a sequence that is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to the heavy chain or light chain sequences of the 10E8V2.0/iMab antibody (i.e., SEQ ID NO:1, SEQ ID NO:2, SEQ ID NO: 33, or SEQ ID NO:34).

In various embodiments, the bispecific antibody (e.g., HIV CrossMab antibody) may comprise a sequence that includes at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 40, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acid alterations with respect to the heavy chain or light chain sequences of the 10E8V2.0/iMab antibody (i.e., SEQ ID NO:1, SEQ ID NO:2, SEQ ID NO: 33, or SEQ ID NO:34).

In various embodiments, the bispecific antibody may comprise one or more amino acid alterations in the Complementarity Determining Regions (CDRs) of the 10E8V2.0/iMab antibody (e.g., the CDR1, CDR2 or CDR3 regions). In another embodiment, the bispecific antibody may comprise one or more amino acid alterations in the framework regions (FWs) of the bispecific antibody (e.g., the FW1, FW2, FW3, or FW4 regions). In a further embodiment, the amino acid alterations may be in the joining regions (J regions) of the 10E8V2.0/iMab antibody (e.g., the J1, J2, J3, J4, J5, J6, or J7 regions).

In some embodiments, the bispecific antibody comprises a variant heavy chain derived from 10E8V2.0 (i.e., SEQ ID NO:34). In such embodiments, the bispecific antibody may include one or more mutations at positions selected from L72, I75, F77, L89, Y98, F100a, W100b, Y100e, P100f, P100g, L108, and/or L170 of the heavy chain (the mutation positions on SEQ ID NO: 34 are determined by the Kabat numbering system). In some embodiments, the bispecific antibody may include one or more mutations at positions selected from L72, I75, F77, and/or L108. In some embodiment, the bispecific antibody may include the one or more mutations selected from L72K, I75K, F77T, and L108K. In an embodiment, the bispecific antibody comprises a heavy chain comprising the amino acid sequence of SEQ ID NO: 47.

In some embodiments, the bispecific antibody comprises a variant light chain derived from 10E8V2.0 (i.e., SEQ ID NO:33). In such embodiments, the bispecific antibody may include one or more mutations at positions selected from L15, P40, I45, and P112 of the light chain (the mutation positions on SEQ ID NO: 33 are determined by the Kabat numbering system). In some embodiments, the bispecific antibody may include one or more mutations at positions selected from P40 and I45. In some embodiments, the bispecific antibody may include one or more mutations selected from P40T and I45K. In an embodiment, the bispecific antibody comprises a light chain comprising the amino acid sequence of SEQ ID NO: 46.

In some embodiments, the bispecific antibody comprises a variant light chain derived from MV1 (i.e., SEQ ID NO: 1). In such embodiments, the bispecific antibody may include mutations at positions 52-54 (the mutation position on SEQ ID NO: 1 is determined by the Kabat numbering system). In some embodiments, the bispecific antibody may include amino acid mutations at positions 52-54. In some embodiments, the amino acid at position 52 is mutated to Asn (N), the amino acid at position 53 is mutated to Ser (S), and the amino acid at position 54 is mutated to Thr (T). In some embodiments, the Asn mutation at position 52 is N-linked glycosylated. In an embodiment, the bispecific antibody comprises a light chain comprising the amino acid sequence of SEQ ID NO: 38.

In illustrative embodiment, the bispecific antibody comprises a heavy and light chain derived from 10E8 comprising the amino acid sequence of SEQ ID NO: 47 and SEQ ID NO:46, respectively. The bispecific antibody further comprises a heavy and light chain derived from MV1 comprising the amino acid sequence of SEQ ID NO: 1 and SEQ ID NO:2, respectively.

Modification of the amino acid sequence of recombinant binding protein is achieved using any known technique in the art e.g., site-directed mutagenesis or PCR based mutagenesis. Such techniques are described, for example, in Sambrook et al., *Molecular Cloning: A Laboratory Manual*, Cold Spring Harbor Press, Plainview, N.Y., 1989 and Ausubel et al., *Current Protocols in Molecular Biology*, John Wiley & Sons, New York, N.Y., 1989.

Methods for producing antibodies, such as those disclosed herein, are known in the art. For example, DNA molecules encoding light chain variable regions and/or heavy chain variable regions can be chemically synthesized using the sequence information provided herein. Synthetic DNA molecules can be ligated to other appropriate nucleotide sequences, including, e.g., expression control sequences, to produce conventional gene expression constructs encoding the desired antibodies. Production of defined gene constructs is within routine skill in the art. Alternatively, the sequences provided herein can be cloned out of hybridomas by conventional hybridization techniques or polymerase chain reaction (PCR) techniques, using synthetic nucleic acid probes whose sequences are based on sequence information provided herein, or prior art sequence information regarding genes encoding the heavy and light chains.

Nucleic acids encoding desired antibodies can be incorporated (ligated) into expression vectors, which can be introduced into host cells through conventional transfection or transformation techniques. Exemplary host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions. Specific expression and purification conditions will vary depending upon the expression system employed.

In various embodiments, the bispecific antibodies of the present invention (e.g., HIV CrossMab antibodies) are used in therapy. For example, the bispecific antibody (e.g., HIV CrossMab antibody) can be used to neutralize HIV in a mammal (e.g., a human patient). For example, antibodies of the invention can bind to HIV so as to partially or completely inhibit one or more biological activities of the virus. In an embodiment, the bispecific antibody (e.g., HIV CrossMab antibody) neutralizes a R5-tropic HIV. In another embodiment, the bispecific antibody (e.g., HIV CrossMab antibody) neutralizes a X4-tropic HIV. In a further embodiment, the bispecific antibody (e.g., HIV CrossMab antibody) neutralizes a R5X4 dual-tropic HIV. In some embodiments, use of the antibody to neutralize HIV in a mammal comprises administering to the mammal a therapeutically effective amount of the antibody.

Generally, a therapeutically effective amount of active component is in the range of, for example, about 0.1 mg/kg to about 100 mg/kg, e.g., about 1 mg/kg to about 100 mg/kg, e.g., about 1 mg/kg to about 10 mg/kg of the body weight of the patient. In various embodiments, a therapeutically effective amount of active component is in a range of about 0.01 mg/kg to about 30 mg/kg of the body weight of the patient, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg, about 25 mg/kg, about 26 mg/kg, about 27 mg/kg, about 28 mg/kg, about 29 mg/kg, about 30 mg/kg body weight, inclusive of all values and ranges there between.

In some embodiments, the therapeutically effective amount of active component is any value between about 1 to 10 mg/kg, between about 10 to 20 mg/kg, between about 20 to 30 mg/kg, between about 30 to 40 mg/kg, between about 40 to 50 mg/kg, between about 50 to 60 mg/kg, between about 60 to 70 mg/kg, between about 70 to 80 mg/kg, between about 80 to 90 mg/kg, or between about 90 to 100 mg/kg.

In some embodiments, the therapeutically effective amount of active component is about 1 mg/kg, about 2 mg/kg, about 3 mg/kg, about 6 mg/kg, about 10 mg/kg, about 20 mg/kg, about 30 mg/kg, or about 60 mg/kg delivered intravenously (IV).

In some embodiments, the therapeutically effective amount of active component is about 2.5 mg/kg, about 5 mg/kg, about 10 mg/kg, or about 20 mg/kg delivered subcutaneously (s.c.) or intramuscularly (i.m).

The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue level. Alternatively, the initial dosage can be smaller than the optimum, and the dosage may be progressively increased during the course of treatment. Human dosage can be optimized, e.g., in a conventional Phase I dose escalation study designed to run from, for example, 0.5 mg/kg to 20 mg/kg. Dosing frequency can vary, depending on factors such as route of administration, dosage amount and the disease being treated. Exemplary dosing frequencies are more than once daily, about once per day, about twice a day, about three times a day, about four times a day, about five times a day, about every other day, about every third day, about once a week, about once every two weeks, about once every month, about once every two months, about once every three months, about once every six months, or about once every year. Formulation of antibody-based drugs is within ordinary skill in the art.

In various embodiments, the antibodies of the invention may be administered for a prolonged period. For example, the antibodies may be administered for at least about 1 week, at least about 4 weeks, about 8 weeks, or at least about 12 weeks. In some embodiments, the regimen is for at least about 1 month, at least about 6 months, at least about 12 months, at least about 1 year, at least about 2 years, at least about 3 years, at least about 4 years, at least about 5 years, at least about 6 years, at least about 7 years, at least about 8 years, at least about 9 years, at least about 10 years, at least about 15 years, at least about 20 years, at least about 30 years, at least about 40 years, or at least about 50 years.

For therapeutic use, an antibody may be combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing antibodies, such as those disclosed herein, can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, and rectal administration. In an embodiment, the route of administration for antibodies of the invention is IV infusion. Useful formulations can be prepared by methods well known in the pharmaceutical art. For example, see *Remington's Pharmaceutical Sciences*, 18th ed. (Mack Publishing Company, 1990).

In some embodiments, the pharmaceutical compositions are formulated as a composition adapted for oral administration. Compositions for oral delivery can be in the form of tablets, lozenges, aqueous or oily suspensions, granules, powders, sprinkles, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation.

In some embodiments, the pharmaceutical compositions are formulated as a composition adapted for parenteral administration. Dosage forms suitable for parenteral administration (e.g. intravenous, subcutaneous, intramuscular, or intraperitoneal injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents.

In some embodiments, the compositions may additionally include pharmaceutically acceptable excipients or carriers. Exemplary excipients include sodium citrate, dicalcium phosphate, etc., and/or a) fillers or extenders such as starches, lactose, sucrose, glucose, mannitol, silicic acid, microcrystalline cellulose, and Bakers Special Sugar, etc., b) binders such as, for example, carboxymethylcellulose, alginates, gelatin, polyvinylpyrrolidone, sucrose, acacia, polyvinyl alcohol, polyvinylpolypyrrolidone, methylcellulose, hydroxypropyl cellulose (HPC), and hydroxymethyl cellulose etc., c) humectants such as glycerol, etc., d) disintegrating agents such as agar-agar, calcium carbonate, potato or tapioca starch, alginic acid, certain silicates, sodium carbonate, cross-linked polymers such as crospovidone (cross-linked polyvinylpyrrolidone), croscarmellose sodium (cross-linked sodium carboxymethylcellulose), sodium starch glycolate, etc., e) solution retarding agents such as paraffin, etc., f) absorption accelerators such as quaternary ammonium compounds, etc., g) wetting agents such as, for example, cetyl alcohol and glycerol monostearate, etc., h) absorbents such as kaolin and bentonite clay, etc., and i) lubricants such as talc, calcium stearate, magnesium stearate, solid polyethylene glycols, sodium lauryl sulfate, glyceryl behenate, etc., and mixtures of such excipients. One of skill in the art will recognize that particular excipients may have two or more functions.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

EXAMPLES

Example 1. Construction and Characterization of HIV CrossMab Antibodies

FIGS. 13A-E and FIGS. 14A-E demonstrate that some iMab-based CrossMabs have greater potency and breadth than parental Abs. Except otherwise stated, all iMab-based bispecific antibodies were constructed using the MV1 variant. IC80, the antibody concentration that confers 80% neutralization of viral infectivity, is one method to evaluate antibody potency against HIV. The lower the IC80 number (indicated in the y-axis of the graphs in term of antibody concentration (µg/ml)), the more potent the antibody is at neutralizing a particular HIV strain or isolate. IC50, the antibody concentration that confers 50% neutralization of viral infectivity, is another method to evaluate antibody potency against HIV. The lower the IC50 number (indicated in the y-axis of the graphs in term of antibody concentration (µg/ml)), the more potent the antibody is at neutralizing a particular HIV strain or isolate.

Various sets of antibodies were tested against a large panel of HIV-1 pseudoviruses (118 different HIV viral isolates) representative of HIV envelope diversity by geography, clade, tropism, and stage of infection. IC80 and IC50 were used to evaluate the strength of antiviral potency and breadth. FIGS. 13E and 14E clearly demonstrate that, as compared to the parental antibodies iMab and 10E8, the bispecific CrossMab of the two together (10E8/iMab) neutralizes almost all HIV viruses (each virus is indicated as a dot) more potently. The other antibody sets (used to make 145/iMab, 117/iMab, 128/iMab and 151/iMab) sometimes enhance HIV potency compared to their parental components and sometimes do not.

As shown in FIGS. 15A-E, the antibody iMab is also relatively potent in cell-cell neutralizing assays. PGT145, 3BNC117, 10E8, PGT128 and PGT151 are relatively potent at neutralizing cell-free viral infection, but are poor in neutralizing viruses in cell-cell transmission assays. Creating bispecific antibodies including PGT145, 3BNC117, 10E8, PGT128 and PGT151 with iMab makes these chimeric antibodies active at neutralizing viruses in a cell-cell transmission assay. It can be seen that 10E8/iMab is the most potent antibody in these comparative studies. It is also found that 10E8/iMab is most active in preventing cell-cell transmission in vitro.

Figure 3:
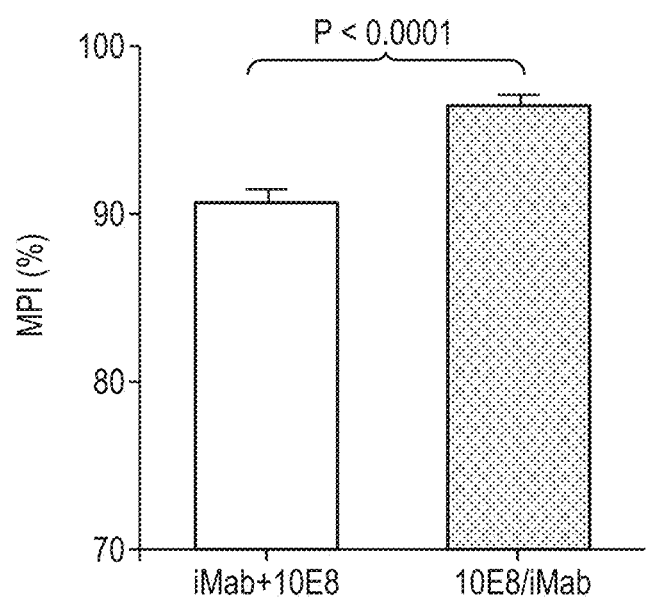
FIG. 3 is a graph comparing the maximum percentage inhibition (MPI) against cell-to-cell HIV transmission using a combination of iMab and 10E8 antibodies with CrossMab bispecific 10E8/iMab antibodies. Except otherwise stated, all iMab-based bispecific antibodies were constructed using the MV1 variant.
Figure 4I:
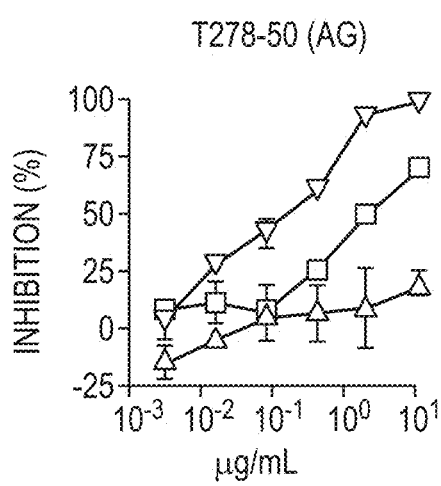
Figure 4J:
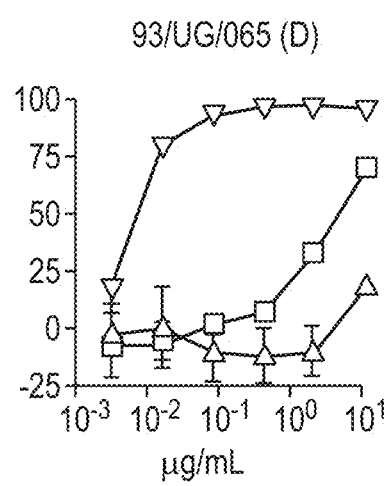
Figure 6A:
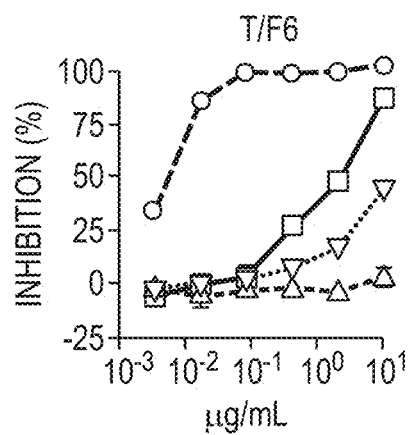
FIGS. 6A-D are a series of graphs comparing the inhibition of various strains of HIV using varying concentrations of 10E8, X19, 10E8/X19 or 10E8/P140 antibodies.
Figure 6B:
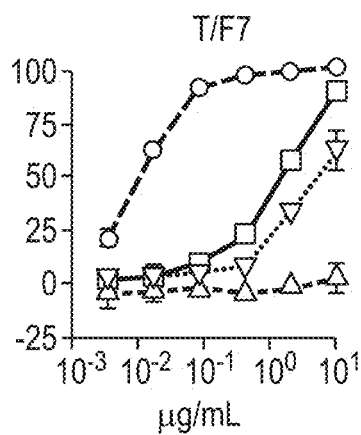
Figure 6C:
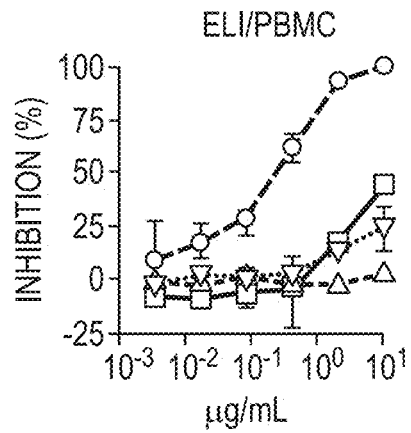
Figure 6D:
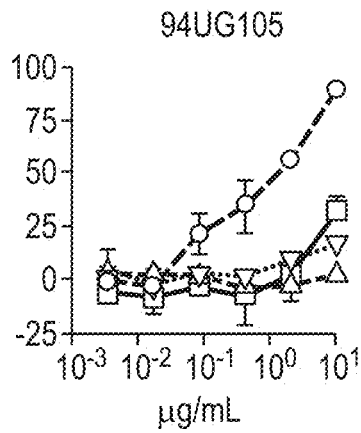
Figure 16:
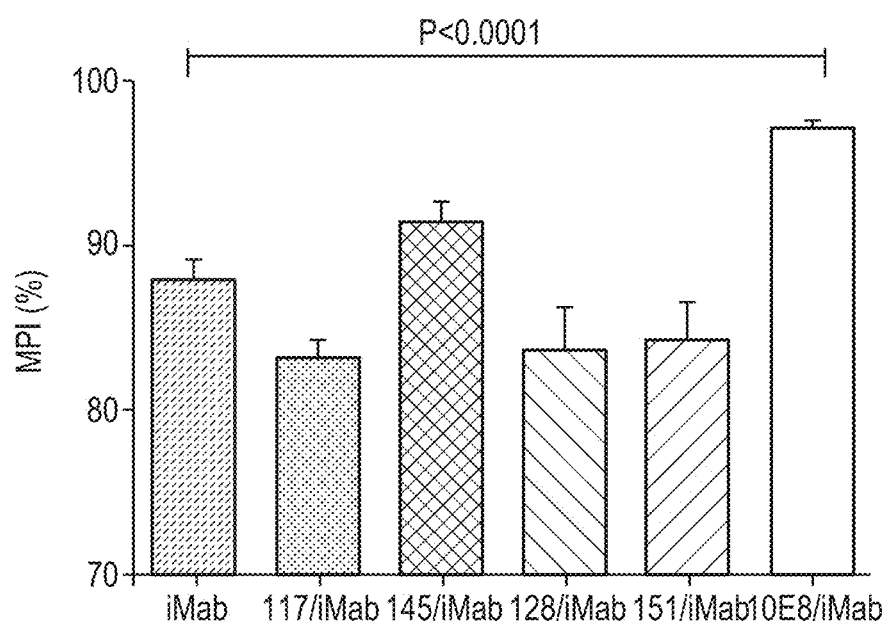
FIG. 16 is a graph displaying the maximum percent inhibition (MPI) of CrossMab bispecific antibodies and parental antibodies against cell-to-cell transmission of HIV.

As illustrated in FIG. 16, the improved potency of 10E8/iMab is statistically significant. FIG. 3 shows that improved potency requires covalent linkage of the antibody, i.e., the CrossMab format (since co-administration of two parental antibodies, iMab and 10E8, provides a lower MPI than the fused and physically linked bispecific 10E8/iMab antibody). FIGS. 10, 11A-E, 12A-E, 13A-E, and 14A-E provide further evidence of the improved potency of iMab-derived CrossMab antibodies over its parental antibodies.

In summary, it is found that, for the iMab-based CrossMabs (fused with PGT145, 3BNC117, PGT151, PGT128 and 10E8), 117/iMab improves breadth but not potency; 145/iMab, 151/iMab and 128/iMab improve breadth and potency; and 10E8/iMab markedly improves breadth and potency. In terms of epitope location/accessibility and potential models of neutralization, 10E8/iMab appears to exhibit pre- and post-attachment neutralization; 145/iMab, 151/iMab and 117/iMab appear to exhibit pre-attachment neutralization; and 117/iMab may show signs of steric restriction and potentially reduced potency for some viruses. 10E8/iMab also exhibits potent activity against HIV cell-to-cell transmission.

As also shown in FIGS. 13A-D and 14A-D, Pro 140-based CrossMab activities are sometimes weaker than their parental antibodies and corresponding iMab-based CrossMabs, as shown by the high concentrations required to reach IC80 and IC50. Anchoring of these four mAbs to the host cell receptor CCR5 via another host cell receptor-binding antibody called Pro 140 does not improve the antiviral potency or breadth (as measured by IC80 against a large panel of HIV isolates) compared to their respective parental antibodies. These panels indicate that Pro140-based CrossMabs for these four antibodies are weaker than their corresponding iMab-based CrossMabs (IC50 and IC80 comparisons of Pro140-based vs. iMab-based CrossMabs).

As shown in FIGS. 13E and 14E, 10E8/P140, a fifth Pro 140-based CrossMab, is more potent than its parental antibodies and 10E8/iMab CrossMab. These panels illustrate a comparison of the potency (IC80 or IC50) of parental mAb Pro140 (right-most column of data points in FIGS. 13E and 14E), bispecific CrossMab 10E8/P140 (second from right column of data points in FIGS. 13E and 14E), and parental mAb 10E8 (center column of data points in FIGS. 13E and 14E) against a large panel of HIV isolates. These panels also illustrate a comparison of the potency (IC80 or IC50) of parental mAb iMab (left-most column of data points in FIGS. 13E and 14E), bispecific CrossMab 10E8/iMab (second from left column of data points in FIGS. 13E and 14E), and parental mAb 10E8 (center column of data points in FIGS. 13E and 14E) against a large panel of HIV isolates. The second from left and second from right columns of data points in FIGS. 13E and 14E illustrate a comparison of the potency (IC80 or IC50) of the bispecific CrossMabs 10E8/iMab and 10E8/P140 against a large panel of HIV isolates.

Pro 140 is known to not have activity against X4 HIV viruses, as X4 viruses use CXCR4 as a co-receptor for HIV-1 entry, and Pro 140 binds to CCR5. 10E8 alone has very weak activity against X4 viruses. However, the bispecific CrossMab 10E8/Pro 140 can neutralize all X4 viruses tested to date better than either of the parent antibodies. FIGS. 4A-J illustrate the effectiveness of 10E8, Pro 140, and 10E8/P140 bispecific CrossMab antibody in inhibition of various strains of HIV.

As shown in FIGS. 5A-G, 10E8/Pro140 CrossMab is a more potent inhibitor of various strains of HIV than the co-administration of the two parental antibodies, demonstrating a synergistic, not merely additive, enhancement of potency with this particular bispecific antibody.

As shown in FIGS. 6A-D, a CrossMab of 10E8 fused to a non-membrane bound antibody (X19) does not provide enhanced potency, as can be seen when compared to membrane bound 10E8/P140. Thus, the potency of the 10E8/P140 CrossMab appears to require anchoring of 10E8 to the cell membrane. However, membrane binding alone does not afford the enhanced potency of these CrossMabs. FIGS. 7A-H show that anchoring 10E8 on HER2 does not provide substantial potency enhancement as compared to anchoring 10E8 on CCR5. Anchoring of 10E8 to a viral receptor specifically (in this case CCR5 via Pro 140 or CD4 via iMab) provides enhanced antiviral activity.

Δ10E8 is a mutant version of the 10E8 mAb that has a one amino acid deletion in the light chain FR3. Compared to 10E8, Δ10E8 has a much weaker epitope binding activity, as illustrated in FIGS. 8A-C. However, once the Δ10E8 was anchored on a cell receptor (by combining Δ10E8 and iMab in a CrossMab antibody—iMab specifically binds cell receptor CD4), FIGS. 8D-E, show that its inhibition activity is improved. These data suggest the contribution of specific cell receptor anchoring, i.e., anchoring on a viral receptor or a viral co-receptor, in enhancing the activity of this HIV antibody. Still, while Δ10E8/P140 CrossMab has improved antiviral activity over Δ10E8, it is still not as potent as 10E8/P140 CrossMab. Δ10E8/P140 CrossMab is comparatively more effective in neutralizing R5 viruses than it is in neutralizing X4 viruses.

Figure 20:
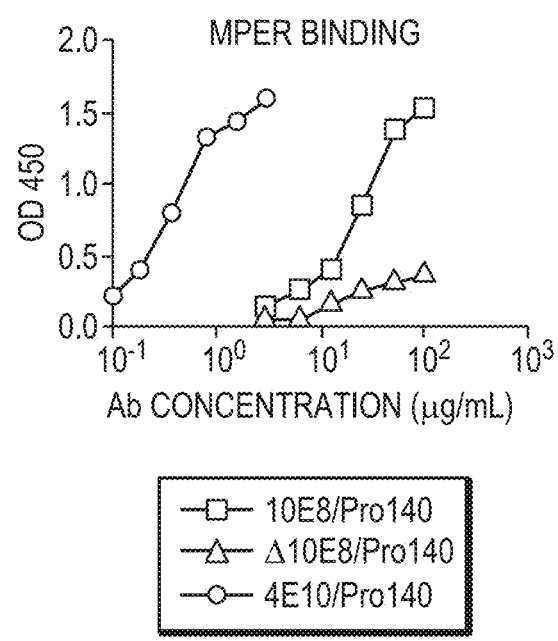
FIG. 20 compares the binding of CrossMab bispecific antibodies 10E8/Pro140, Δ10E8/Pro140 and 4E10/Pro140 to the HIV-1 glycoprotein MPER.

4E10 is an anti-gp41 MPER mAb known to be less potent than the anti-gp41 MPER mAb 10E8. Similar to the results for Δ10E8, FIGS. 20 and 21A-G show that anchoring 4E10 on co-receptor CCR5 (via Pro 140 in a CrossMab antibody) enhanced antiviral activity of 4E10 significantly. Taken together, this suggests that the anchoring of a number of anti-gp41 MPER Abs to either CCR5 or CD4 (via combining the MPER Abs with P140 or iMab in a CrossMab antibody bispecific) can greatly improve the potency and breadth of the respective anti-gp41 MPER Ab. Multiple parameters contribute to enhanced activity of certain bispecific CrossMabs against HIV, including parental Ab potency, affinity, and pre- and post-attachment neutralization abilities. In particular, the 10E8/Pro140 CrossMab represents an effective combination in terms of overcoming energetic, spatial and temporal constraints, targeting sequential/inter-dependent steps in the entry process, epitope location/accessibility, binding affinity, pre- and post-attachment neutralization, and binding geometry. As shown in FIG. 20, 4E10/Pro140 has a greater binding affinity for MPER than Δ10E8/Pro140 and 10E8/Pro140. FIGS. 9A-G show the inhibition potency of 10E8/Pro140, Δ10E8/Pro140 and 4E10/Pro140, and their parental antibodies 10E8, Δ10E8 and 4E10 against various strains of HIV. FIGS. 10, 13A-E, 14A-E, 15A-E, 16, and 17A-B provide additional evidence of the greater potency of CrossMab antibodies as compared to their parental antibodies individually and the parental antibodies in combination.

The enhanced antiviral coverage of 10E8/iMab and 10E8/Pro140 CrossMabs is illustrated in FIG. 10, which depict the potency and breadth of several antibodies against HIV. The x-axis indicates the concentration of a particular antibody, the y-axis indicates the percent of a large panel of HIV viral isolates neutralized by a particular antibody at a specific concentration, and each line indicates a different antibody evaluated. The left-most lines along the x-axis and those that can closely approach or reach 100% on the y-axis indicate a highly potent and broad antibody against HIV. 10E8/P140 CrossMab and 10E8/iMab CrossMab are among the most effective antibodies with respect to both viral coverage and potency, and are significantly more effective than their parental antibodies.

FIGS. 18A-H and 19A-C show the potency of the CrossMab 10E8/515H7 antibody as compared to its parental antibodies and previously discussed antibodies. The potency of a CrossMab antibody does not appear to correlate directly with the density of cell membrane protein targets, as the density of CCR5 (the target of Pro140) is less than that of CD4 (the target of ibalizumab), yet the potency of 10E8/Pro140-derived CrossMab antibody is greater than that of 10E8/iMab-derived CrossMab antibody.

Figure 22A:
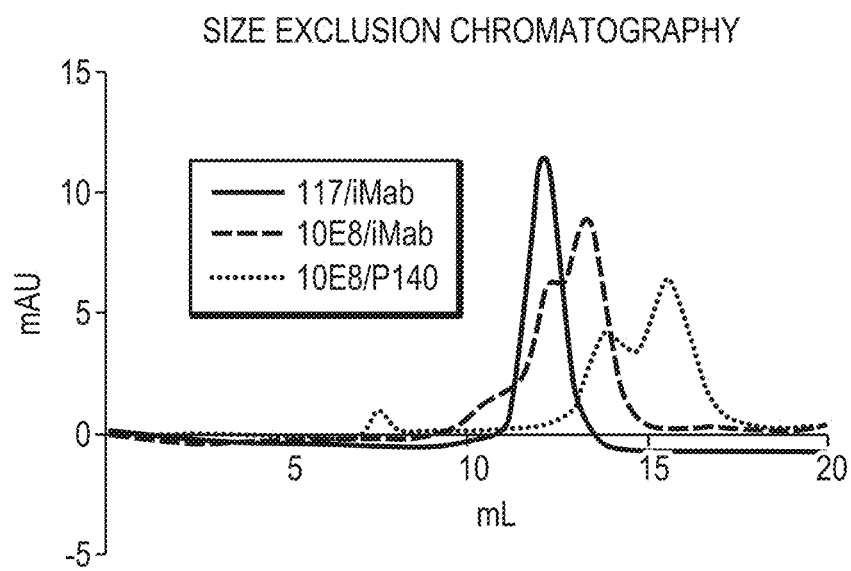
FIG. 22A is size exclusion chromatography analysis of the CrossMab antibodies 10E8/iMab, 10E8/P140 and 3BNC117/iMab.
Figure 22B:
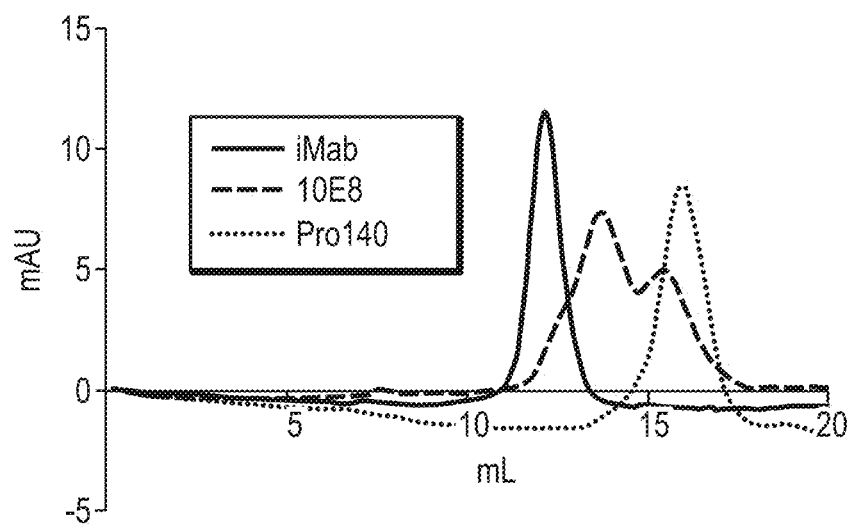
FIG. 22B is size exclusion chromatography analysis of the monoclonal antibodies iMab, 10E8 and Pro140.

As shown in FIGS. 22A-B, the lack of single, sharp peaks in size exclusion chromatography indicates a type of instability indicative of multiple molecular species for 10E8 and 10E8-derived CrossMab antibodies. Table 1 recites various process and formulation modifications used to resolve the 10E8 instability. However, as indicated by the "X" in the SEC or Size Exclusion Chromatography column, the modifications were unsuccessful in providing a single, sharp peak.

TABLE 1

Process and formulation screen to resolve 10E8 instability

| Conditions | SEC | Purpose |
| --- | --- | --- |
| EDTA* | X | sequester metal ions, ↓ enzymatic activity |
| Acetic Acid* | X | ↓pH, stabilize protonated form of free thiols, ↓reduction activity |
| L Lysine* | X | competitive inhibitor against reduction components |
| CuSO4* | X | maintain reducing components in oxidized form, enzyme inhibitor |
| 3-day harvesting | X | decreased cell death, ↓ enzymatic activity |
| SEC running buffer condition | X | modification of analytical conditions |

TABLE 1-continued

Process and formulation screen to resolve 10E8 instability

| Conditions | SEC | Purpose |
|---|---|---|
| His formulation buffer | X | modification of analytical conditions |

Figure 23:
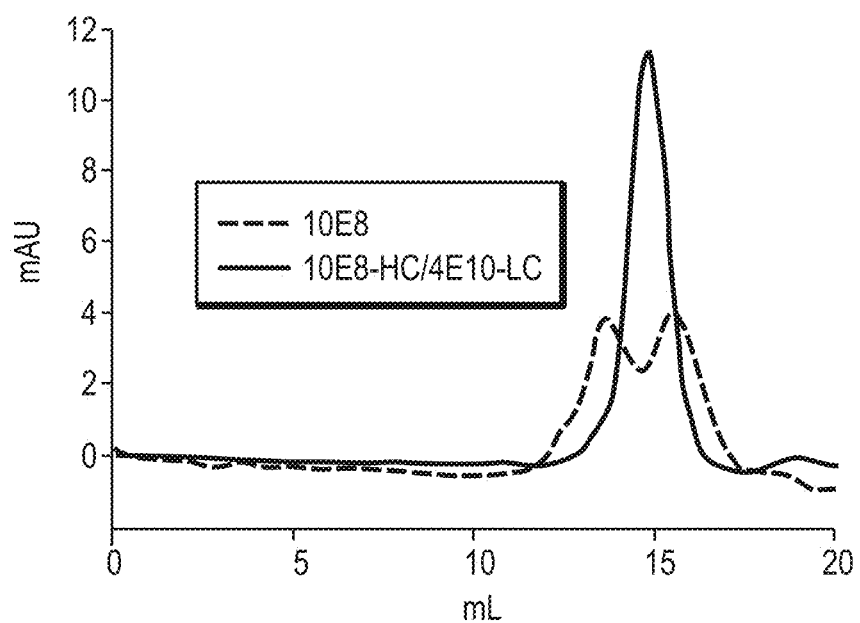
FIG. 23 is size exclusion chromatography analysis of monoclonal antibody 10E8 and a chimeric antibody comprised of the 10E8 heavy chain paired with the 4E10 light chain.
Figure 24A:
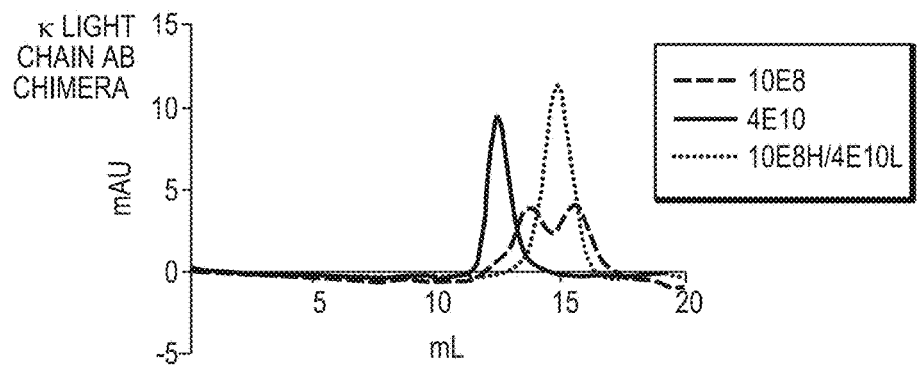
FIGS. 24A-C are a series of size exclusion chromatography graphs of: the monoclonal antibodies 10E8 and 4E10 and a chimeric antibody comprised of the 10E8 heavy chain paired with the 4E10 light chain (FIG. 24A), the monoclonal antibody 10E8 and 10E8 mutants with potentially stabilizing mutations genetically engineered in the 10E8 light chain (FIG. 24B), and the monoclonal antibody 10E8 and 10E8 mutants genetically grafted with the kappa light chain of non-10E8 antibodies (FIG. 24C).
Figure 24B:
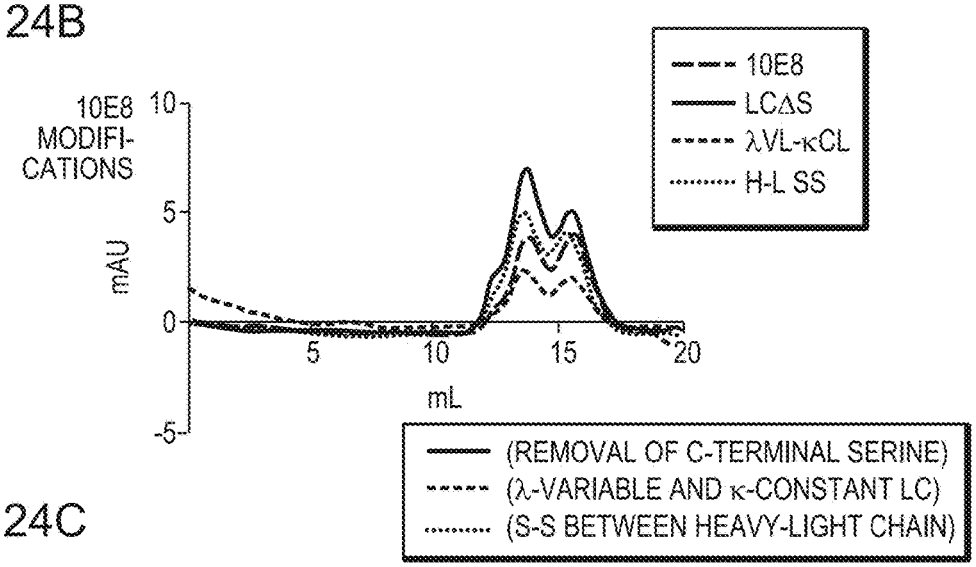
Figure 24C:
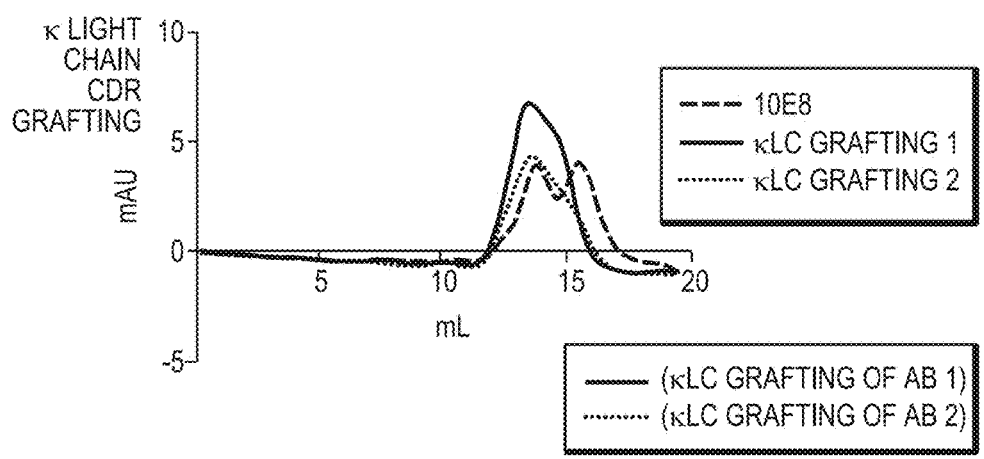
Figure 26A:
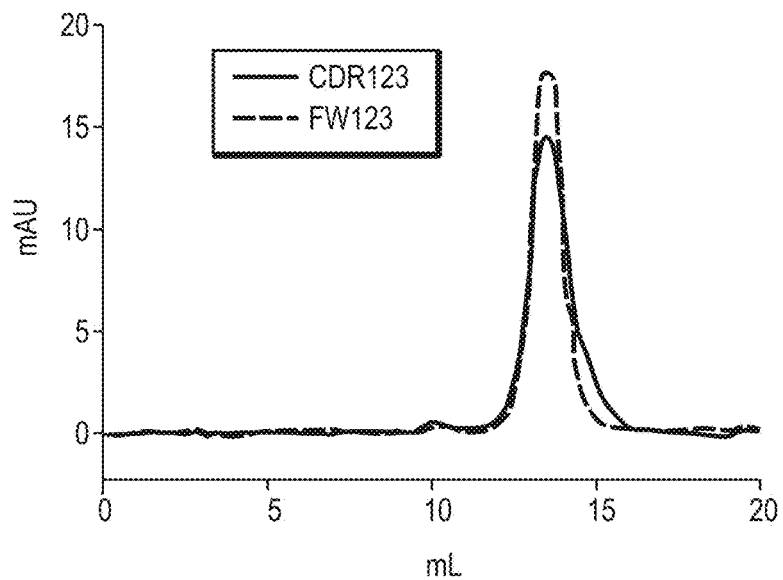
FIG. 26A is a size exclusion chromatography graph of 10E8 chimeric antibodies. CDR123 is a chimeric antibody of the 10E8 heavy chain paired with a 10E8 light chain genetically grafted with the 10E8 antibody germline CDR region sequences. FW123 is a chimeric antibody of the 10E8 heavy chain paired with a 10E8 light chain genetically grafted with the 10E8 antibody germline framework region sequences.
Figure 26B:
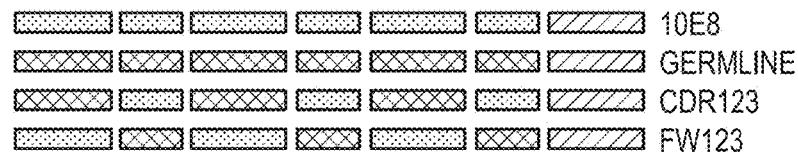
FIG. 26B is a table indicating the expression, HIV MPER binding ability, size exclusion chromatography profile, and HIV neutralization profile of the CDR123 and FW123 antibodies.

Pairing the 10E8 heavy chain with the light chain of 4E10 resolves the instability issue, as shown in FIG. 23, producing a functional, though less potent, antibody. This result indicates that the instability of 10E8 is due to the light chain. Various modifications of the 10E8 light chain, shown in FIGS. 24B-C, such as removal of a C-terminal serine, engineering a lambda-variable region and kappa-constant region chimera, engineering an additional disulfide bond between the 10E8 heavy and light chains, or genetically grafting kappa light chain regions of non-10E8 antibodies onto the 10E8 light chain do not fully resolve 10E8 instability. As shown in FIGS. 25 and 26A-B, the instability is likely due to a combination of the Complementarity Determining Regions ("CDRs") and the framework regions ("FWs") of 10E8. Using 10E8-HC/4E10-LC, each 10E8 light chain CDR was grafted into 4E10LC individually or in concert, as shown in FIG. 25. Addition of 10E8 LC CDR2 and CDR3 are well tolerated, but addition of 10E8 LC CDR1 disrupts the single peak. When all 10E8 CDRs are grafted onto 4E10, the peak is broad. Grafting 10E8 CDRs or frameworks onto its germline light chain λ results in a single peak, as shown in FIG. 26A, but effectiveness in MPER binding and HIV neutralization is decreased. Table 2 summarizes the 10E8 light chain variants tested and the efficacy thereof.

TABLE 2

Generated 10E8 LC variants

| Modifications | Expression | MPER binding | SEC | Neutralization |
|---|---|---|---|---|
| λLC' → ΔS | ✓ | ✓ | X | ✓ |
| λLC' → κLC | ✓ | ✓ | X | ✓ |
| LC CDR grafting (κLC Ab1) | ✓ | ↓ | ? | |
| LC CDR grafting (κLC Ab2) | ✓ | ↓ | ? | |
| H-L S-S bond | X | | X | |
| 10E8-H/4E10-L | ✓ | ↓ | ✓ | ↓ |
| 10E8-H/4E 10-L CDR1 (10E8) | X | | X | |
| 10E8-H/4E 10-L CDR2 (10E8) | ✓ | ↓ | ✓ | ↓ |
| 10E8-H/4E 10-L CDR3 (10E8) | ✓ | ↓ | ✓ | ↓ |
| 10E8-H/4E 10-L CDR123 (10E8) | ✓ | ↓ | ? | ↓ |

Figure 27:
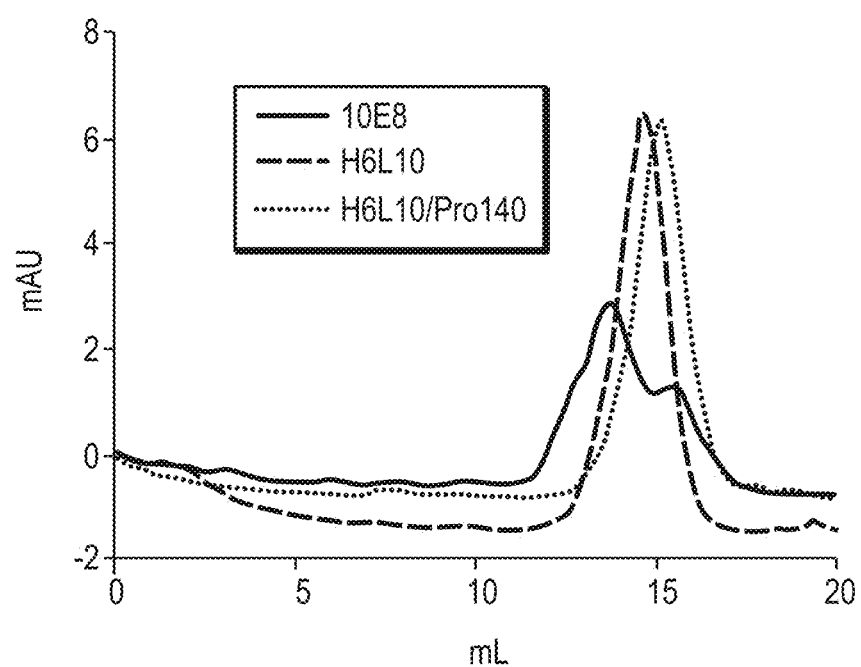
FIG. 27 is a size exclusion chromatography graph of monoclonal antibody 10E8, its somatic variant H6L10, and a CrossMab bispecific antibody consisting of H6L10 paired with Pro140.
Figure 28:
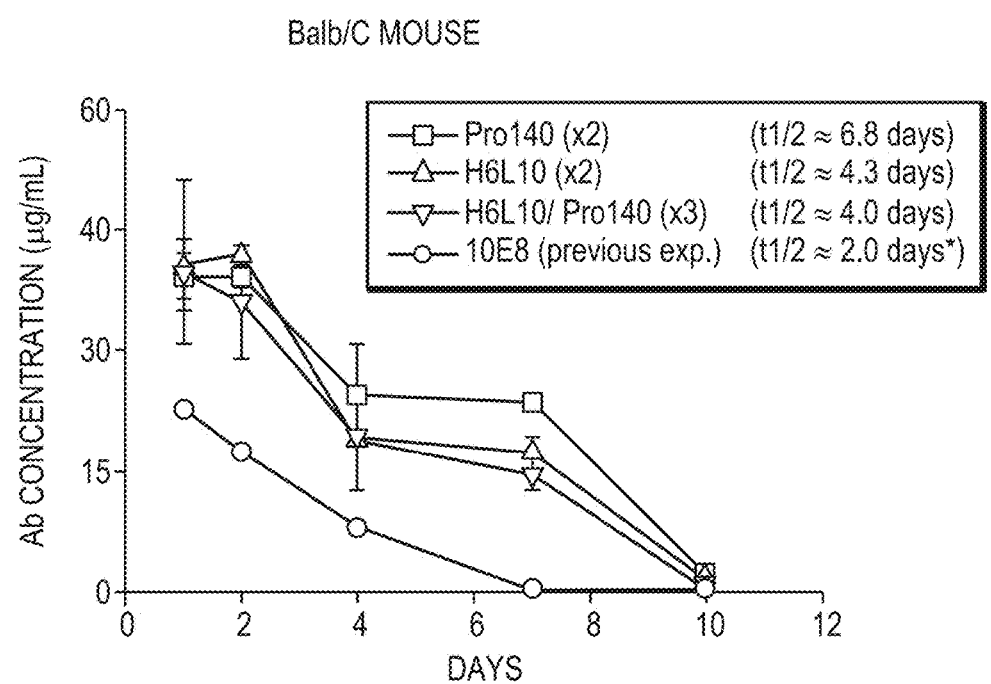
FIG. 28 is a graph depicting the pharmacokinetics profiles of 10E8, H6L10/Pro 140 and its parental antibodies in a mouse model.
Figure 29:
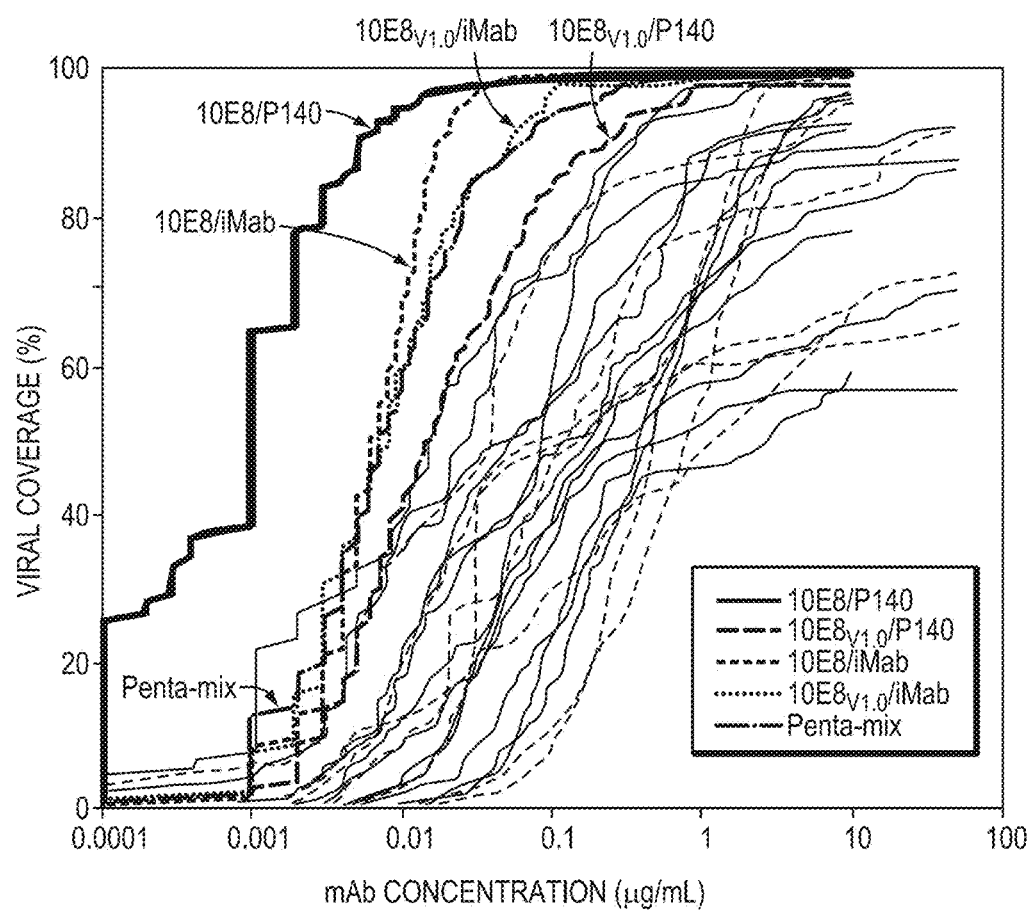
FIG. 29 is a graph comparing the potency of $10E8_{v1.0}$/iMab or P140 CrossMab antibodies with 10E8/iMab or P140 antibodies.

Variant H6L10 of 10E8 antibody was found to be active, non-autoreactive, and stable by size exclusion chromatography, as shown in FIG. 27. H6L10/Pro 140 and its parental antibodies were found to have comparable pharmacokinetics profiles in mice, as shown in FIG. 28. However, as shown in FIG. 29, the H6L10 variant of 10E8 (referred to as $10E8_{v1.0}$) combined with P140 in a bispecific antibody is substantially less potent than 10E8/P140 when tested against a large panel of HIV strains. The H6L10 variant of 10E8 (referred to as $10E8_{v1.0}$) combined with iMab in a bispecific antibody retains the same relative amount of potency as compared to 10E8/iMab when tested against a large panel of HIV strains, but $10E8_{v1.0}$/iMab possesses the same instability as 10E8/iMab as determined by size exclusion chromatography and indicated by an X in Table 3. In an embodiment, the H6L10 variant may further include a S74W mutation.

Table 3 below lists exemplary variants, their activities, size exclusion chromatography results, and pharmacokinetics ("PK") results (see also FIG. 46).

TABLE 3

Exemplary variants that are stable while retaining anti-HIV activity

| Construct | Activity | SEC | PK |
|---|---|---|---|
| 10E8/P140 | +++++ | X | X |
| $10E8_{v1.0}$/P140 | ++ | ✓ | ✓ |
| $10E8_{v1.1}$/P140 | ++++ | ✓ | ✓ |
| $10E8_{v2.0}$/P140 | +++ | X | ND |
| $10E8_{v3.0}$/P140 | +++++ | ✓ | X |
| 10E8/iMab | +++ | X | X |
| $10E8_{v1.0}$/iMab | +++ | X | X |
| $10E8_{v1.1}$/iMab | +++ | X | X |
| $10E8_{v2.0}$/iMab | ++++ | ✓ | ✓ |
| $10E8_{v3.0}$/iMab | ++++ | ✓ | X |

As indicated above, $10E8_{v1.0}$ is a somatic variant of 10E8 known as H6L10. As a mAb, H6L10 has a single peak by SEC but reduced activity compared to 10E8. H6L10/Pro140 CrossMab has single SEC peak and good mouse PK, but reduced anti-HIV activity. H6L10/iMab CrossMab has double SEC peaks and poor mouse PK, but its activity against HIV is roughly the same as 10E8/iMab. $10E8_{v1.1}$ includes a single point mutation in H6L10. When paired with Pro140 in a CrossMab bispecific, this construct has single SEC peak and good mouse PK. Its activity against HIV is improved as compared to 10E8V1.0/Pro140, but still slightly less than that of 10E8/Pro140. When paired with iMab in a CrossMab bispecific, this construct has double SEC peaks and poor mouse PK, and its activity against HIV is still roughly the same as 10E8/iMab and 10E8V1.0/iMab. $10E8_{v2.0}$ is a chimeric antibody variant of 10E8 in which the FW1, CDR1 and part of FW2 are from $10E8_{v1.0}$ and in which the remaining part of FW2, CDR2, FW3, CDR3 and FW4 are from 10E8. When paired with Pro140 in a CrossMab bispecific, this construct has double SEC peaks and has reduced activity against HIV as compared to 10E8/Pro140. When paired with iMab in a CrossMab bispecific, this construct has a single SEC peak, good PK, and activity against HIV that is improved over 10E8/iMab. $10E8_{v3.0}$ is a somatic variant of 10E8 known as H11L1. H11L1/Pro140 CrossMab has a single SEC peak and better anti-HIV activity than any other 10E8/Pro140 construct (including the original one identified), but has poor mouse PK due to autoreactivity. H11L1/iMab CrossMab has a single SEC peak and anti-HIV activity that is better than the original 10E8/iMab identified and roughly equivalent activity to that observed for 10E8V2.0/iMab, but has poor mouse PK due to autoreactivity.

The variant of 10E8 that produced a single SEC peak in the context of a particular CrossMab bispecific was different when paired with Pro140 or iMab. It appears that the stability of the 10E8 arm of these CrossMab bispecific antibodies is context dependent and will vary depending of what antibody it is paired with. Thus, one variant ($10E8_{v1.1}$) was identified that was stable by SEC and with good mouse PK and good anti-HIV activity when paired with Pro140. Another variant ($10E8_{v2.0}$) was also identified that was stable by SEC with good mouse PK and with better anti-HIV activity than the originally identified 10E8/iMab.

Table 4 below describes the autoreactivity of tested variants, where "ANA" refers to anti-nuclear activity and "ACA" refers to anti-cardiolipin activity.

TABLE 4

Autoreactivity assessment in vitro

| Antibodies (50 μg/mL) | ANA | ACA | *Hep-2 Staining score |
|---|---|---|---|
| Negative control | − | − | |
| Low positive control | + | + | |
| High positive control | ++++ | ++++ | |
| iMab | − | − | ' |
| Pro140 | − | − | ' |
| 10ES$_{v1.0}$ | − | − | 0 |
| 10e8$_{v1.0}$ | − | − | ' |
| 10E8$_{v2.0}$ | − | − | ' |
| 10E8$_{v3.0}$ | −/+ | +/++ | 0.5 |
| 10E8$_{v2.0}$/P140 | − | − | ' |
| 10E8$_{v2.0}$/iMab | − | − | ' |
| 10E8$_{v1.1}$/P140 | − | − | ' |
| 10E8$_{v3.0}$/iMab | − | − | ' |
| 10E8$_{v3.0}$/P140 | − | −/+ | ' |

Figure 30:
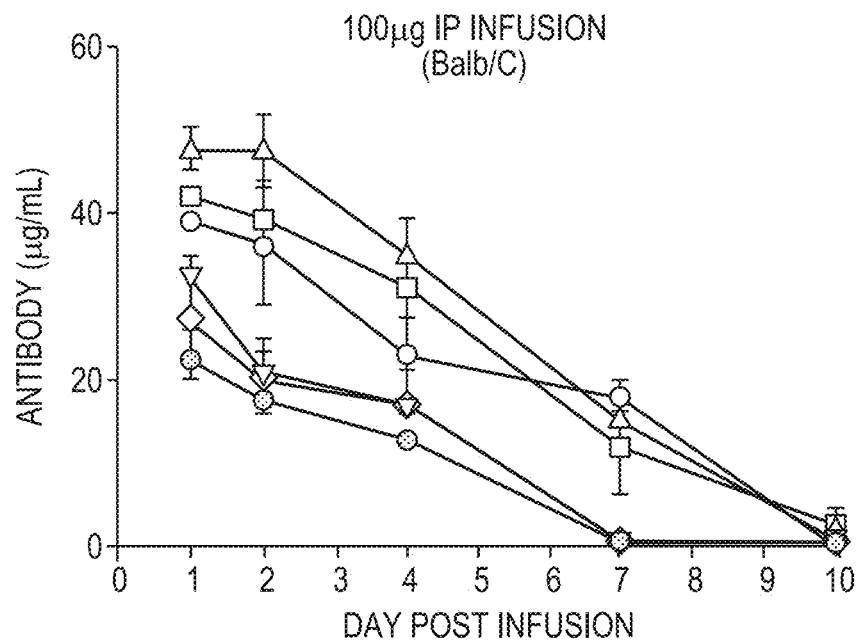
FIG. 30 is a graph depicting the pharmacokinetics of 10E8 and CrossMab antibodies derived from several 10E8 variants and iMab or P140 in a mouse model.
Figure 31A:
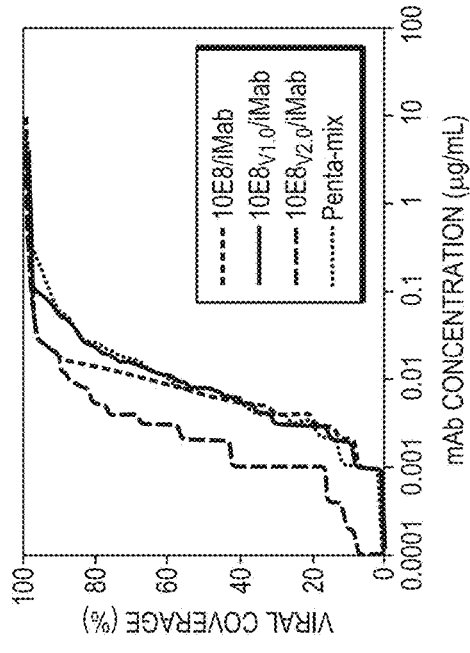
FIGS. 31A-B are a series of graphs depicting the HIV viral coverage of $10E8_{v1.1}$/P140 and $10E8_{v2.0}$/iMab antibodies.
Figure 31B:
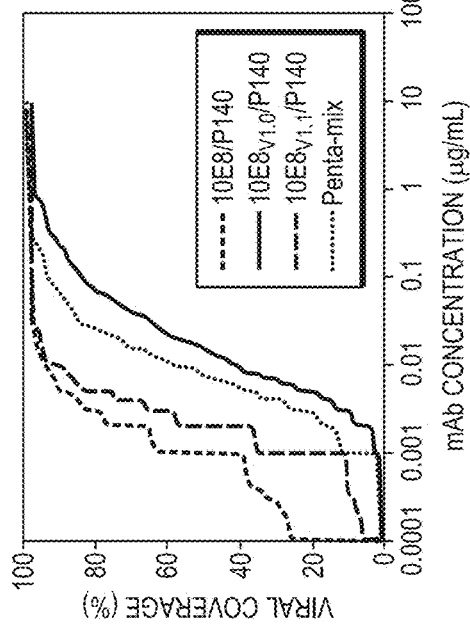
Figure 31C:
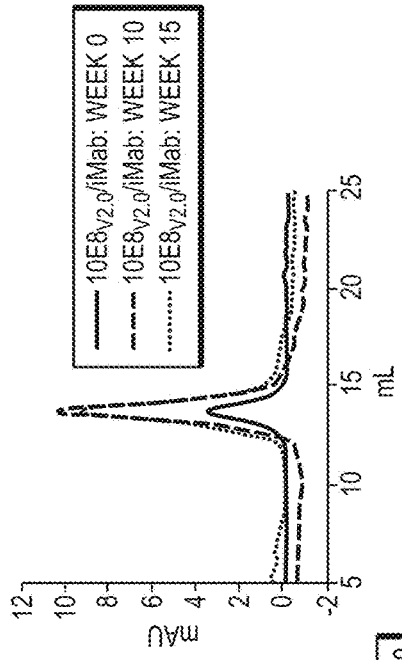
FIGS. 31C-D are a series of graphs depicting size exclusion chromatography stability graphs of $10E8_{v1.1}$/P140 and $10E8_{v2.0}$/iMab antibodies.
Figure 31D:
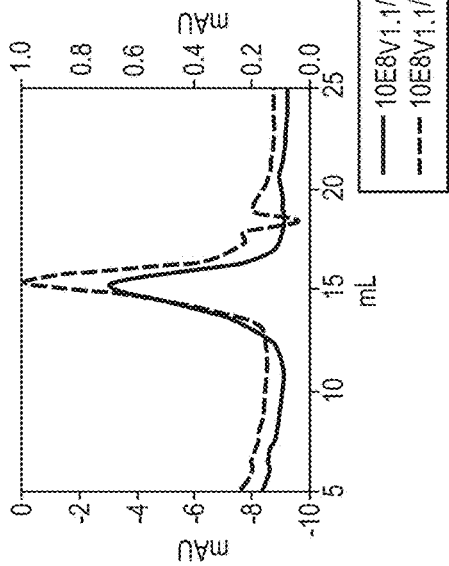
Figure 32A:
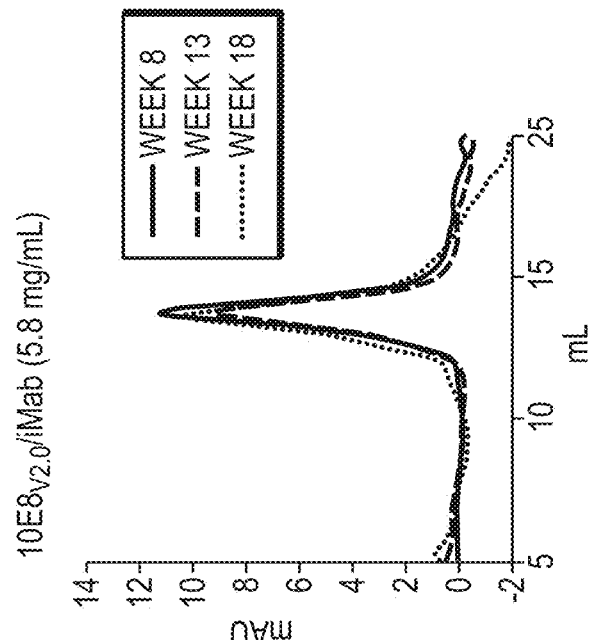
FIGS. 32A-B are a series of graphs depicting the size exclusion stability graphs of $10E8_{v1.1}$/P140 and $10E8_{v2.0}$/iMab antibodies stored in PBS at 4° C.
Figure 32B:
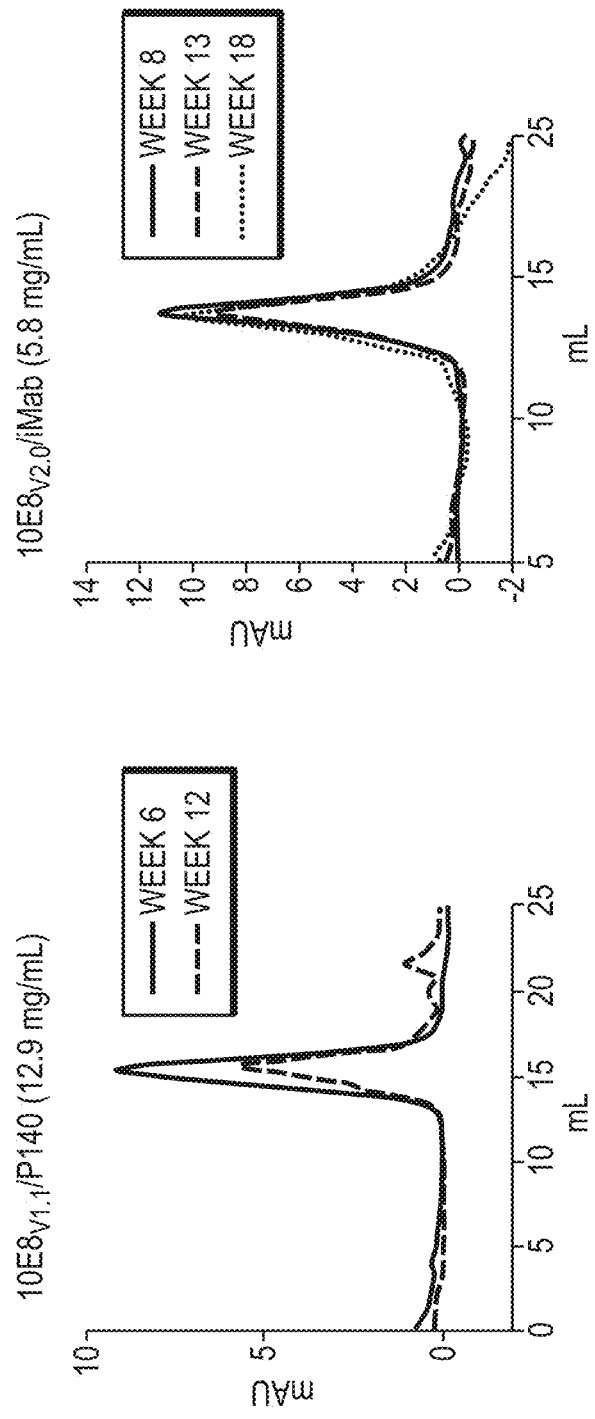
Figure 33:
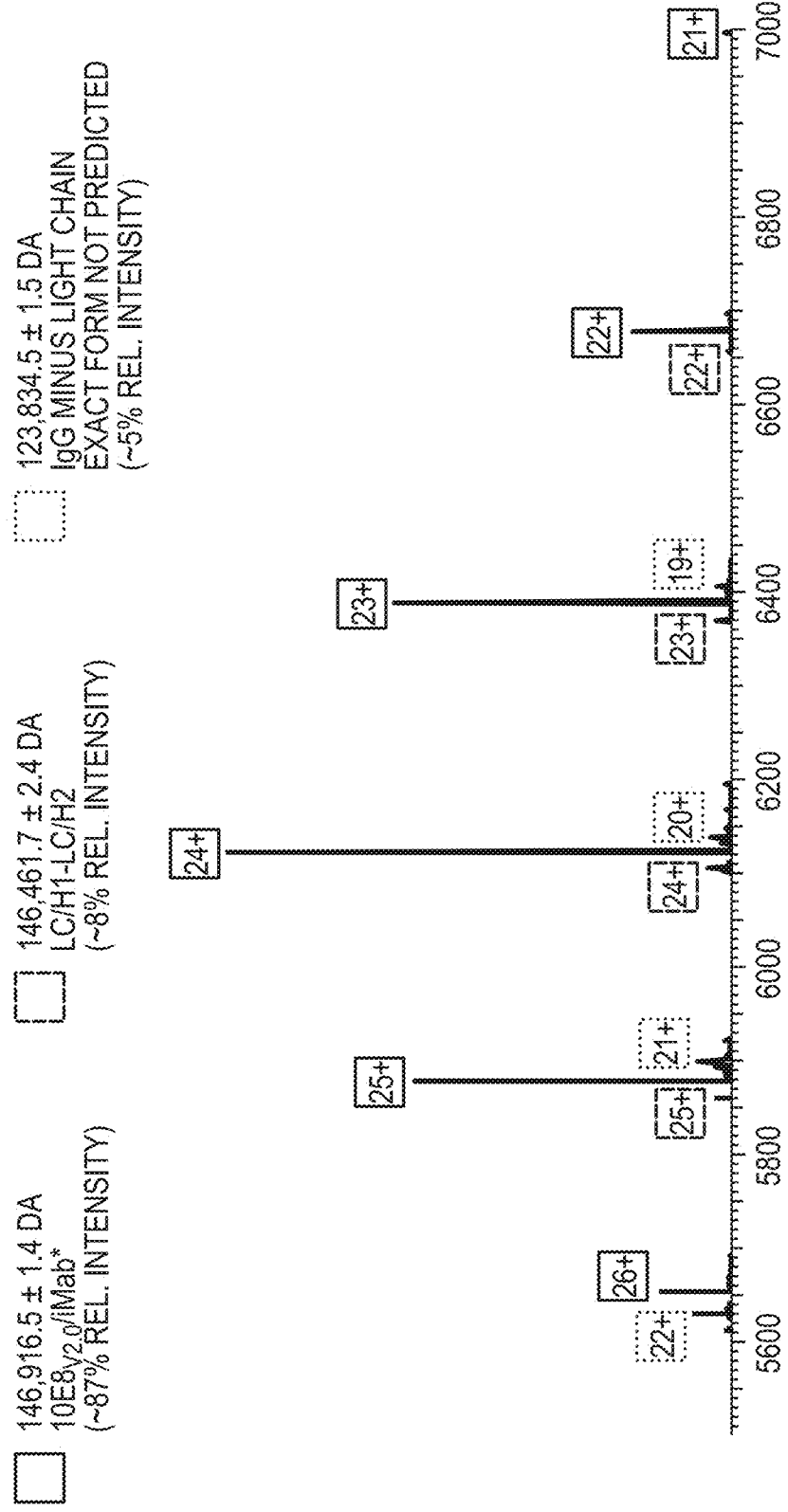
FIG. 33 depicts a native mass spectroscopy analysis of the $10E8_{v2.0}$/iMab (N297A) antibody.
Figure 34B:
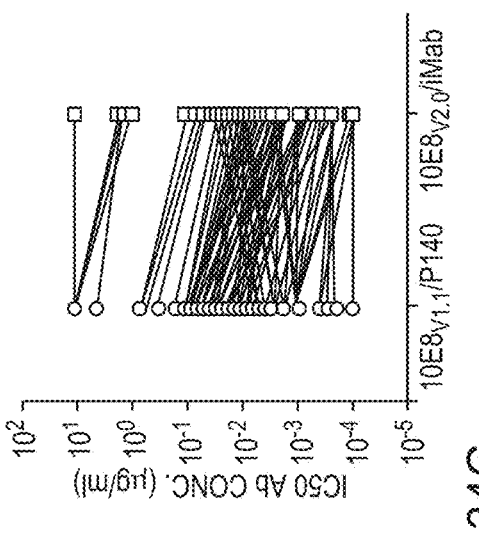
FIGS. 34A-C are a series of graphs comparing the activity of $10E8_{v1.1}$/P140 and $10E8_{v2.0}$/iMab on a HIV Clade C panel, and the IC50 and IC80 activities of the antibodies.
Figure 34C:
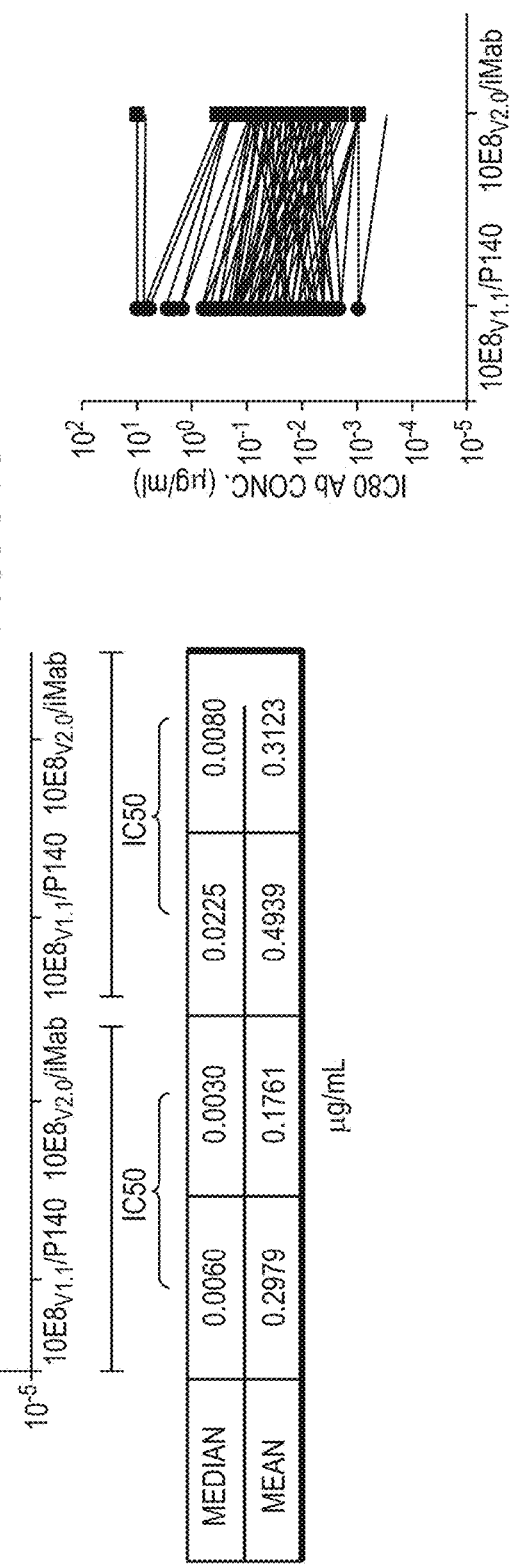
Figure 34A:
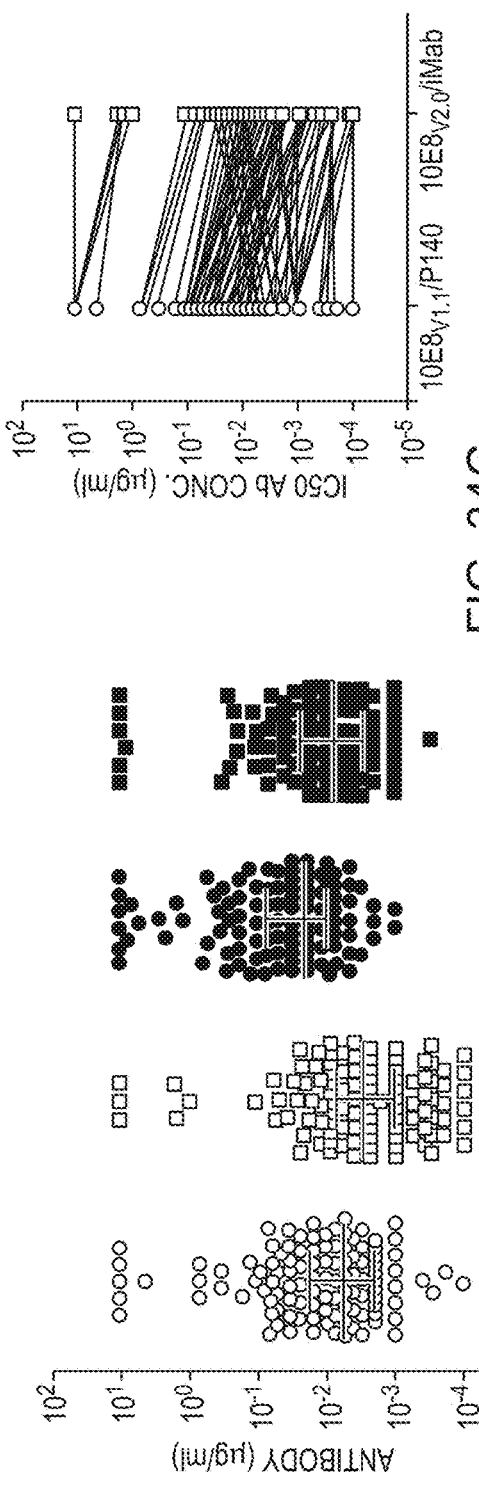
Figure 35:
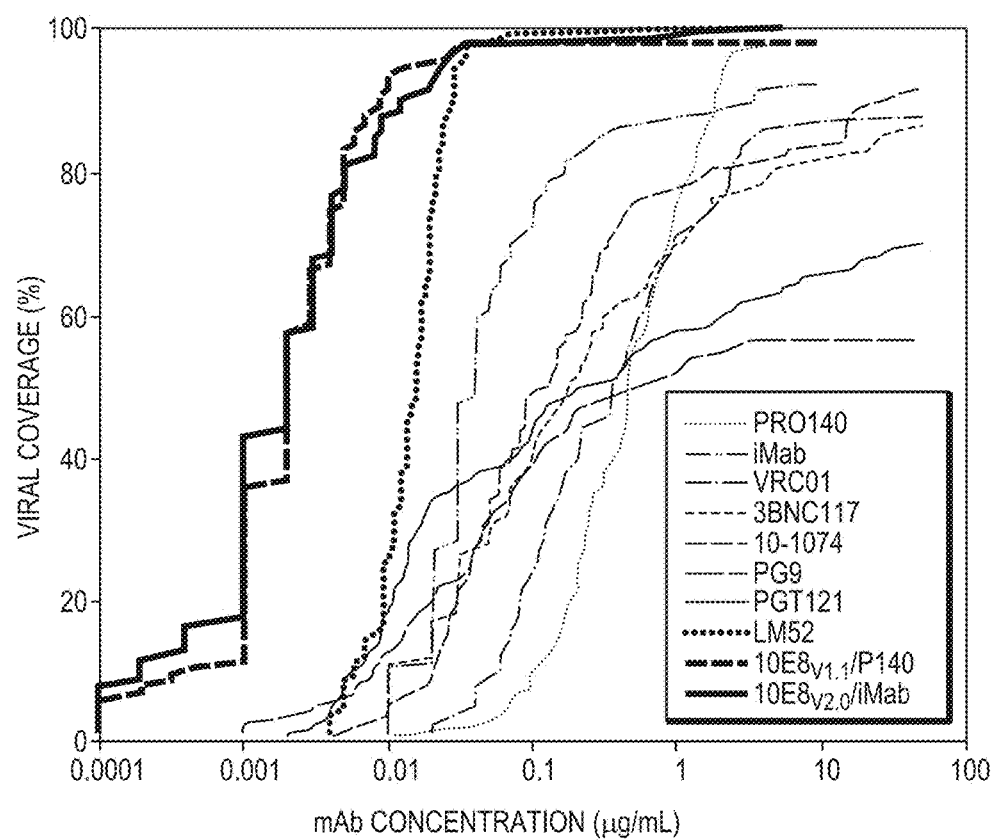
FIGS. 35 and 36 are graphs comparing the potency of $10E8_{v1.1}$/P140, $10E8_{v2.0}$/iMab, and various monoclonal antibodies against HIV.
Figure 36:
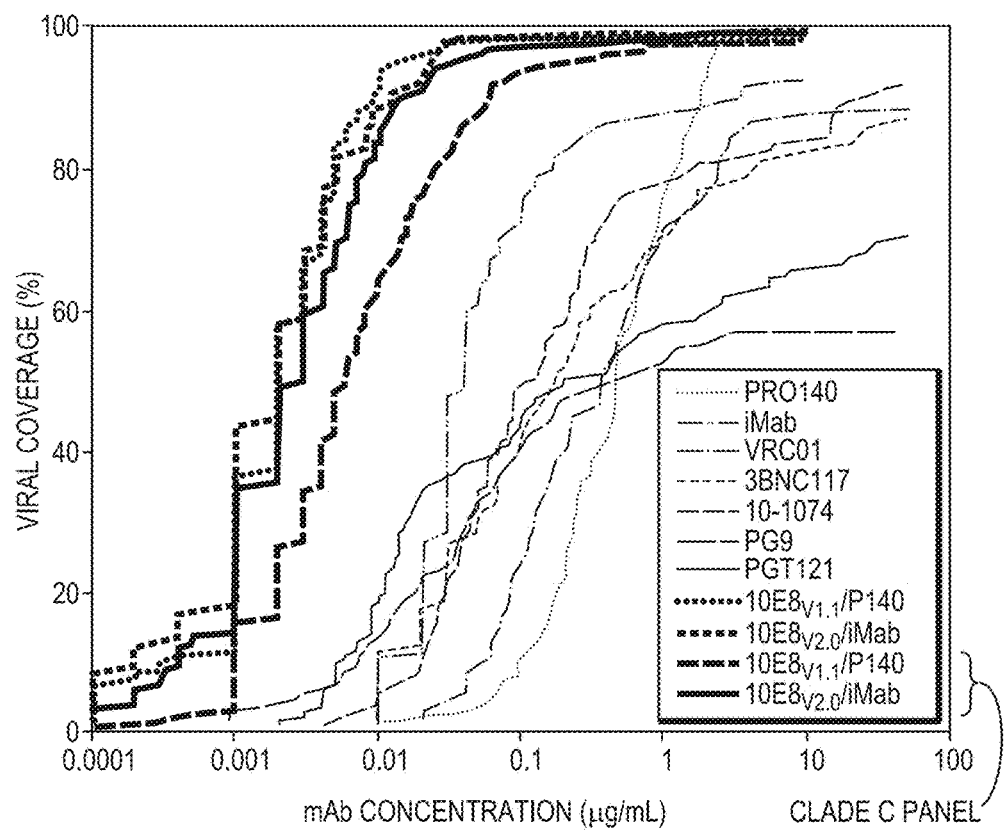

FIG. 30 depicts the pharmacokinetics of 10E8 and CrossMab antibodies derived from several 10E8 variants and iMab or P140 in a mouse model. As shown in FIGS. 31A-D and 32A-B, 10E8$_{v1.1}$/P140 and 10E8$_{v2.0}$/iMab improve anti-HIV activity and stability, and have good stability when stored in PBS at 4° C. FIG. 33 depicts a native mass spectroscopy analysis of 10E8$_{v2.0}$/iMab (N297A). FIGS. 34A-C compare the activity of 10E8$_{v1.1}$/P140 and 10E8$_{v2.0}$/iMab on a HIV Clade C panel, and compares their IC50 and IC80 efficacy. FIGS. 35 and 36 compare the potency of 10E8$_{v1.1}$/P140, 10E8$_{v2.0}$/iMab, and various monoclonal antibodies against HIV.

Example 2. Development of HIV CrossMab Antibodies with Improved Solubility, Stability, and/or Potency Experiments were conducted to develop 10E8/iMab CrossMab antibodies with improved solubility, stability, and activity.

Initially, a number of hydrophobic residues were identified on the surface of the 10E8.2/iMab antibody (also referred to as the 10E8$_{v2.0}$/iMab antibody) which may negatively affect solubility and stability of the bispecific antibody. The hydrophobic residues are presented in Table 5 below (with reference to the Kabat numbering system):

TABLE 5

| Location | Residue |
|---|---|
| L15 | Leu |
| L40 | Pro |
| L45 | Ile |
| L112 | Pro |
| H72 | Leu |
| H75 | Ile |
| H77 | Phe |
| H89 | Leu |
| H98 | Tyr |
| H100a | Phe |
| H100b | Trp |
| H100e | Tyr |
| H100f | Pro |
| H100i | Pro |
| H108 | Leu |
| H170 | Leu |

Figure 37B:
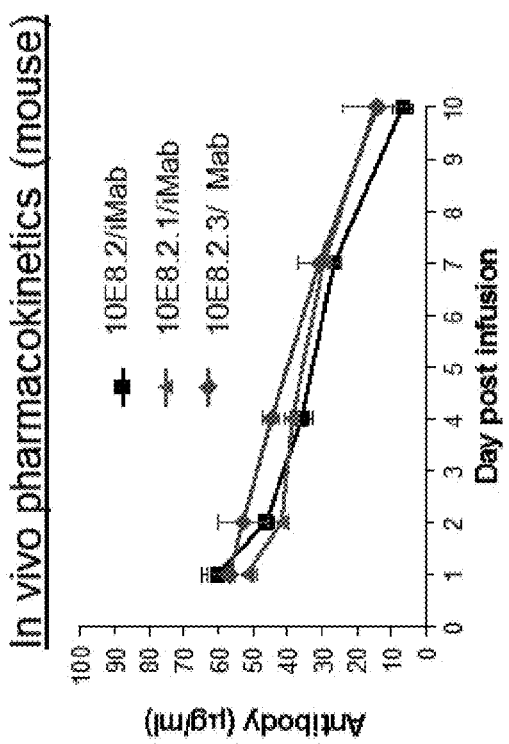
FIGS. 37A-C demonstrate that a select number of 10E8V2.0/iMab (also referred to as 10E8.2/iMab) variants retained functional antiviral activity and increased solubility.
Figure 37A:
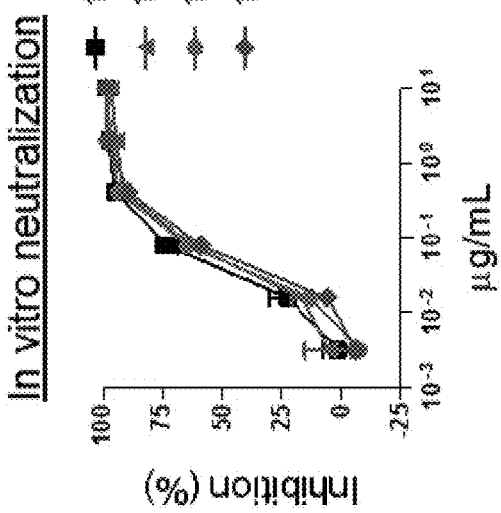

The hydrophobic residues were mutated either alone or in combination to yield 10E8.2/iMab variants that were assessed for their functional activity against HIV and in vivo pharmacokinetic profiles (see FIGS. 37A-B). The amino acid sequences of the various 10E8.2/iMab variants are provided elsewhere herein.

Specifically, in vitro neutralization assays were performed to test the activity of the 10E8.2/iMab variants against HIV. Pseudoviruses were prepared as previously described in Sun et al. 2014. JAIDS. 66, 473-483. Virus neutralization was assessed with a single cycle assay using TZM-bl cells and HIV-1 pseudoviruses as described previously (Seaman et al. 2010. J. Virol. 84, 1439-1452). As shown in FIG. 37A, some of the 10E8.2/iMab variants (e.g., 10E8.2.1/iMab, 10E8.2.2/iMab, and 10E8.2.3/iMab antibodies) retained functional activity in the in vitro HIV-1 neutralization assay as compared to the parental 10E8.2/iMab antibody.

For in vivo pharmacokinetics analysis, BALB/c mice were divided into groups of three, and mice in each group were administered intraperitoneally with 100 μg of the indicated antibody. Blood was drawn from all animals at Days 1, 2, 4, 7 and 10 post antibody administration, and serum was isolated and analyzed for levels of antibody in individual mice. CoStar 96-Well EIA/RIA plates were coated with 100 ng per well of goat anti-human IgG Fc-γ fragment overnight at 4° C. Plates were washed three times with PBS+Tween and blocked with PBS containing 5% milk and 0.5% BSA for 2 hours at room temperature. Mouse serum from the treated animals, and purified antibody in PBS for the standard curves, were added to the wells in 1:2 serial dilutions in PBS containing 2% milk and 0.2% BSA and incubated for 2 hours. After washing, peroxidase-conjugated goat anti-human IgG was incubated for 1 hour at room temperature. Samples were detected by TMB Liquid Substrate System and spectrophotometric readings were performed at 450 nm. As shown in FIG. 37B, some of the 10E8.2/iMab variants (e.g., 10E8.2.1/iMab, 10E8.2.2/iMab, and 10E8.2.3/iMab antibodies) exhibited similar pharmacokinetic profiles as the parental 10E8.2/iMab antibody.

Figure 37C:
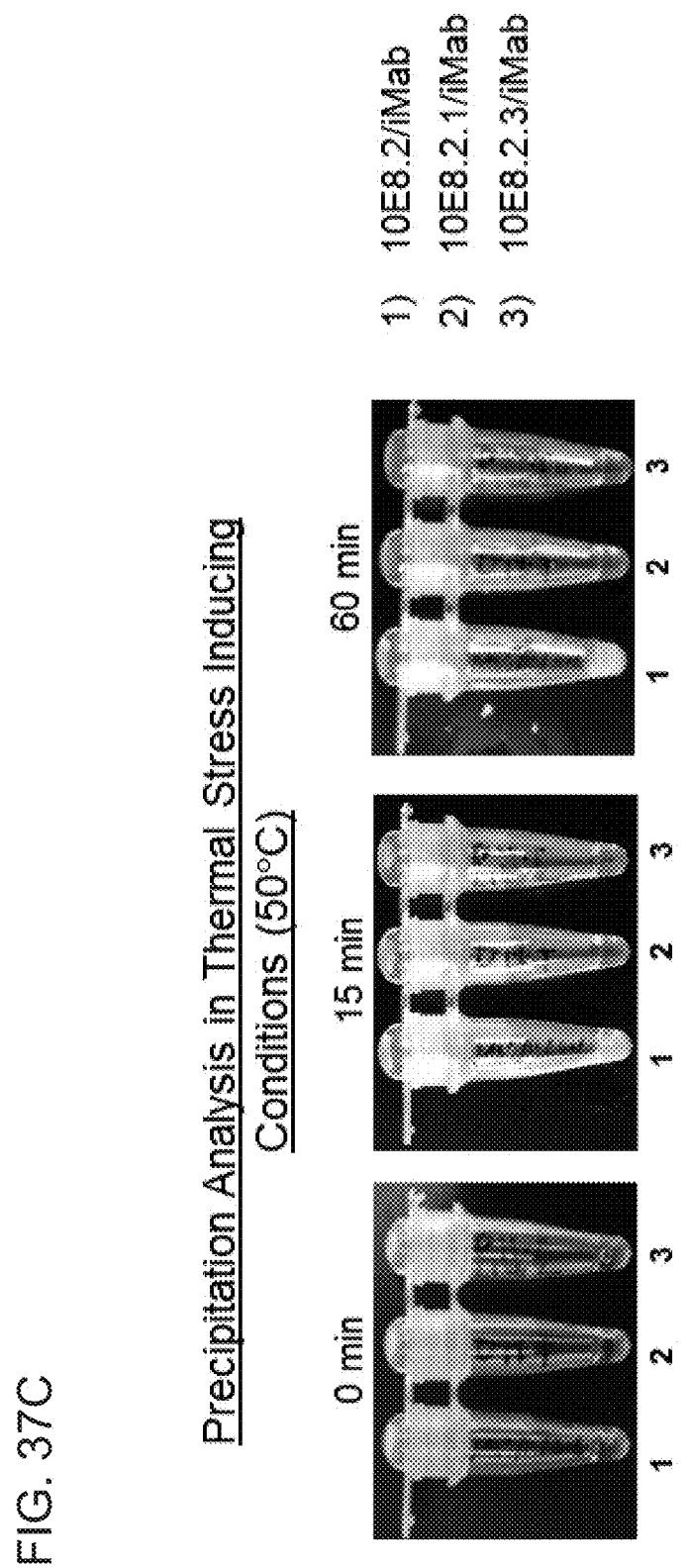

Additionally, the precipitation profiles of the variants were evaluated under thermal stress-inducing conditions. Specifically, 10E8.2/iMab variants were expressed in 293 cells, purified using a Protein A column, exchanged into a solution of PBS (pH 7.4), and concentrated to >30 mg/mL using a membrane with a nominal molecular weight limit of 50 kDa. Samples were then incubated at 50° C. and assessed visually for precipitation at the indicated time points. Results from the thermal stress analysis are shown in FIG. 37C. These results indicate that the 10E8.2.3/iMab variant retained the best combination of favorable antiviral activity by in vitro neutralization, favorable in vivo pharmacokinetics, and increased solubility (decreased precipitation) under thermal stress inducing conditions.

Figure 38B:
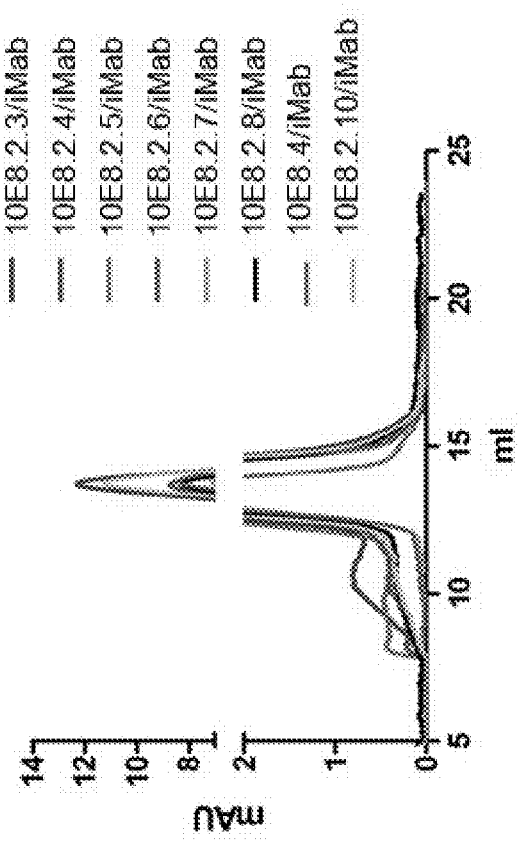
FIGS. 38A-B show the results of size exclusion chromatography, which was used to identify 10E8.2/iMab variants with the least aggregation after thermal stress-inducing conditions.
Figure 38A:
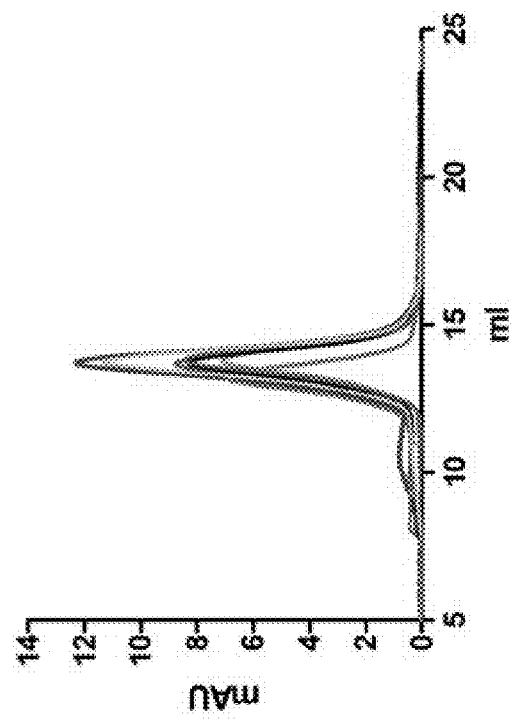

Based on the favorable properties of 10E8.2.3/iMab in the precipitation assay, additional hydrophilic variants and combinations were created off of this bispecific antibody backbone variant. Each of these new variants was evaluated for its aggregation potential by size exclusion chromatography (SEC) after incubation in thermal stress-inducing conditions (see FIGS. 38A-B). In particular, SEC was used to assess the physicochemical homogeneity of the bispecific antibody variants and to resolve monomers from non-monomeric species. Results indicated that the variants 10E8.4/iMab and 10E8.2.10/iMab exhibited the least aggregation, as indicated by a decreased peak size between 7 mL and 11 mL in FIG. 38B. The 10E8.4/iMab variant was advanced into additional solubility and stability studies. This variant comprises a combination of 6 hydrophobic to hydrophilic residue mutations as compared to the parental 10E8.2/iMab antibody.

Figure 45A:
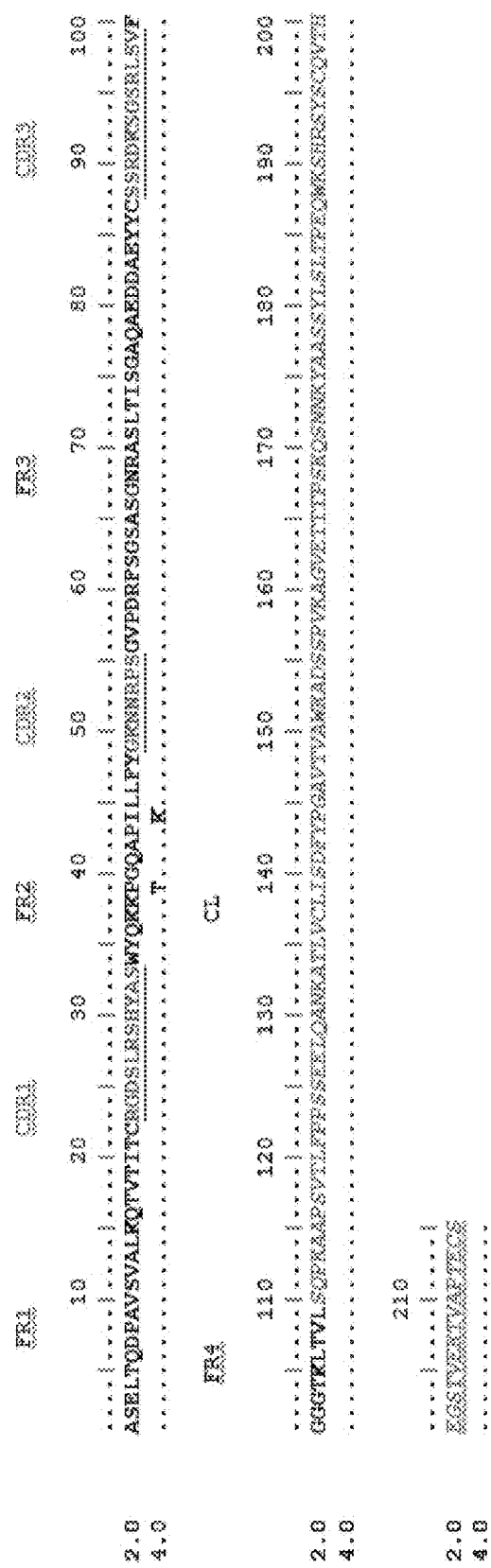
FIG. 45A, shows a sequence alignment of the light chains of 10E8.2/iMab (SEQ ID NO:33) and the 10E8.4/iMab variant (SEQ ID NO:44).
Figure 45B:
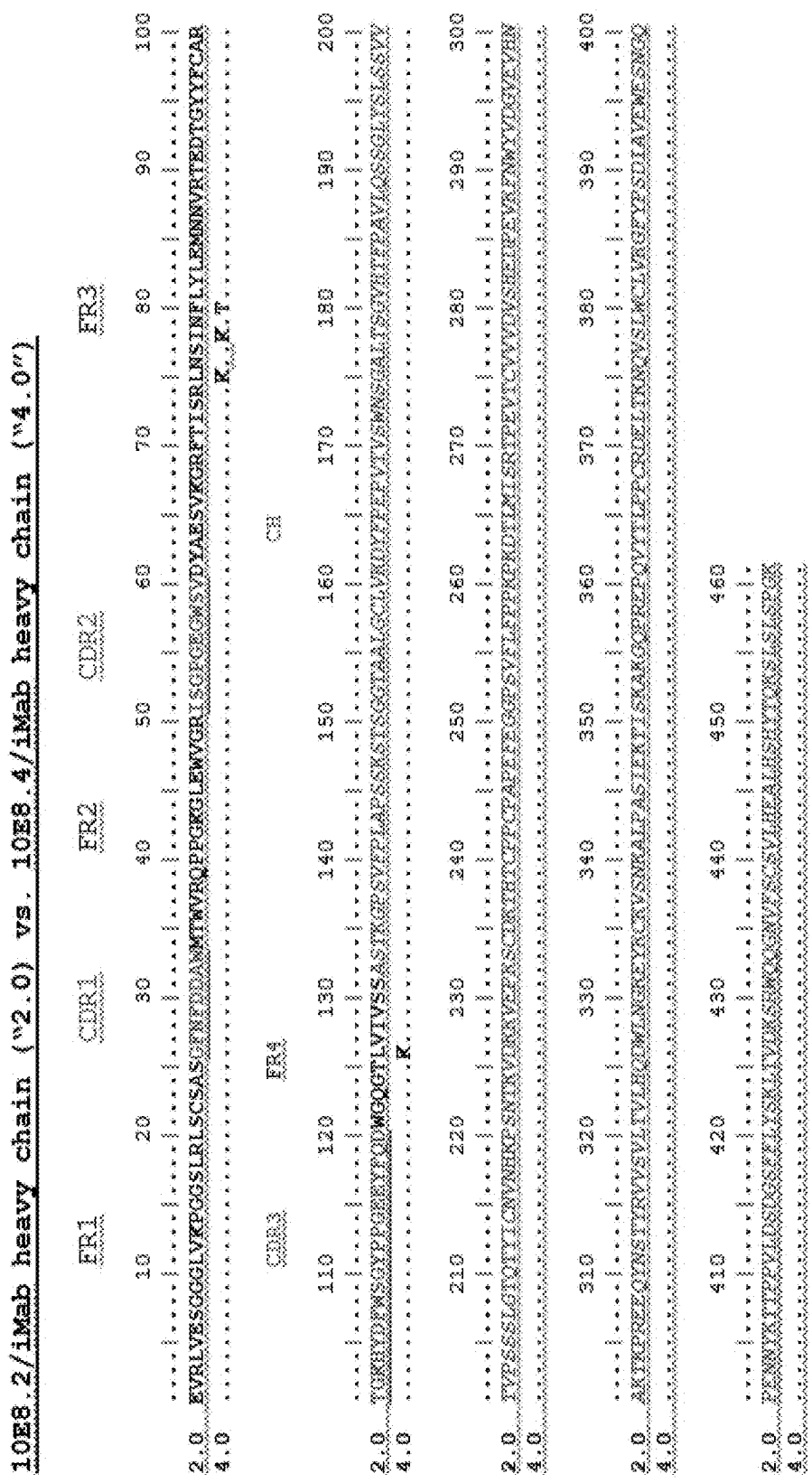
FIG. 45B shows a sequence alignment of the heavy chains of 10E8.2/iMab (SEQ ID NO:34) and the 10E8.4/iMab variant (SEQ ID NO:42). Underlined sequences denote CDR1, CDR2, and CDR3. Italicized sequences denote constant light chain or constant heavy chain sequences.

FIGS. 45A-B provide a sequence alignment of the parental 10E8.2/iMab antibody and the 10E8.4/iMab variant.

Based on the favorable functional and pharmacokinetic characteristics and the reduction in precipitation and aggregation characteristics of the 10E8.4/iMab antibody, additional studies were performed to evaluate the solubility, turbidity, thermostability and forced degradation characteristics of the 10E8.4/iMab antibody in comparison to the 10E8.2/iMab antibody.

Figure 39A:
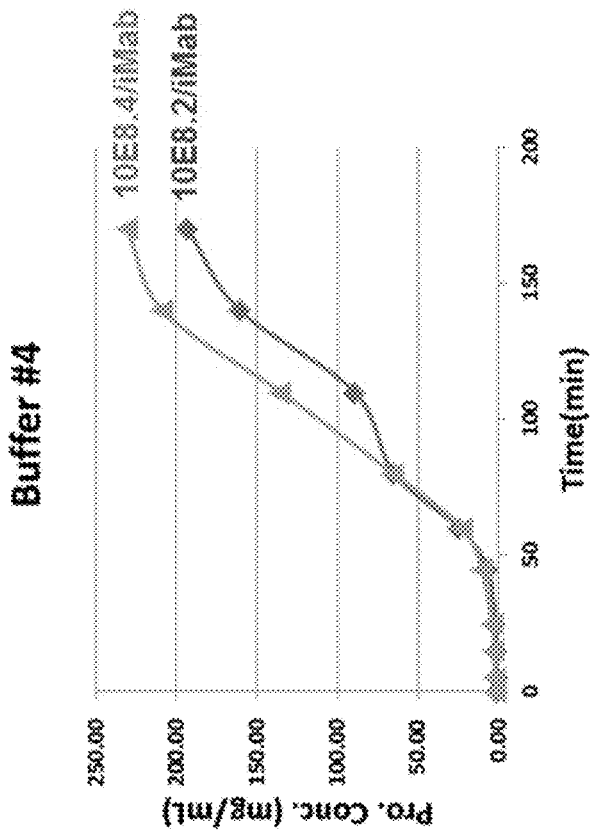
FIGS. 39A-B illustrate the solubility of 10E8.2/iMab and the 10E8.4/iMab variant at 4° C. after ultracentrifugation.
Figure 39B:
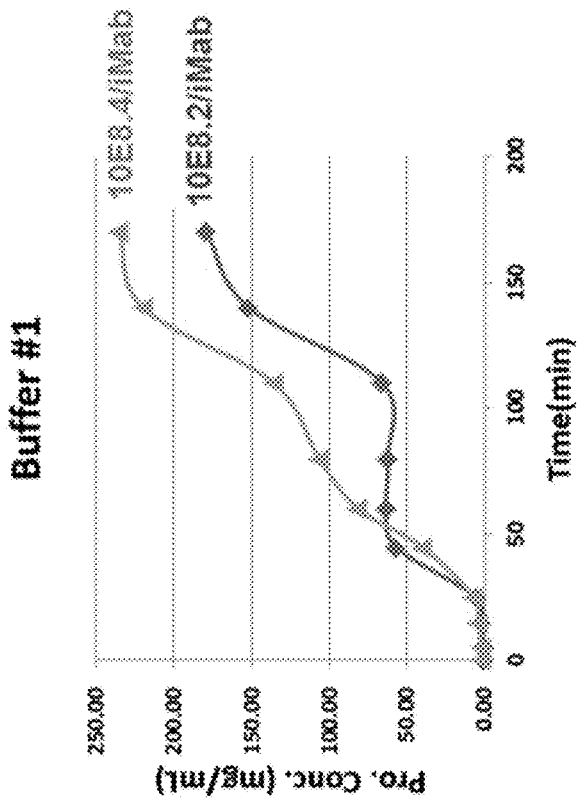

For example, the solubility of the 10E8.4/iMab antibody at 4° C. was determined. In one set of experiments, the 10E8.2/iMab and 10E8.4/iMab antibodies were each buffer exchanged into target buffers and were concentrated via ultracentrifugation at 3000-5000 g, 4° C. Protein concentrations at different time points were determined by absorbance at 280 nm using a NanoDrop 2000 spectrophotometer. All measurements were repeated twice with 2.5 μL sample each time and an average was taken, and then protein concentration was plotted versus time. The maximum protein concentration achieved was determined as the solubility of the protein. As shown in FIGS. 39A-B, at concentrations above 50 mg/mL, the 10E8.4/iMab antibody showed consistently higher protein concentrations and solubility as compared to the 10E8.2/iMab antibody in buffers 1 (acetate buffer, pH 4.5) and 2 (histidine buffer, pH 5.5).

Figure 40:
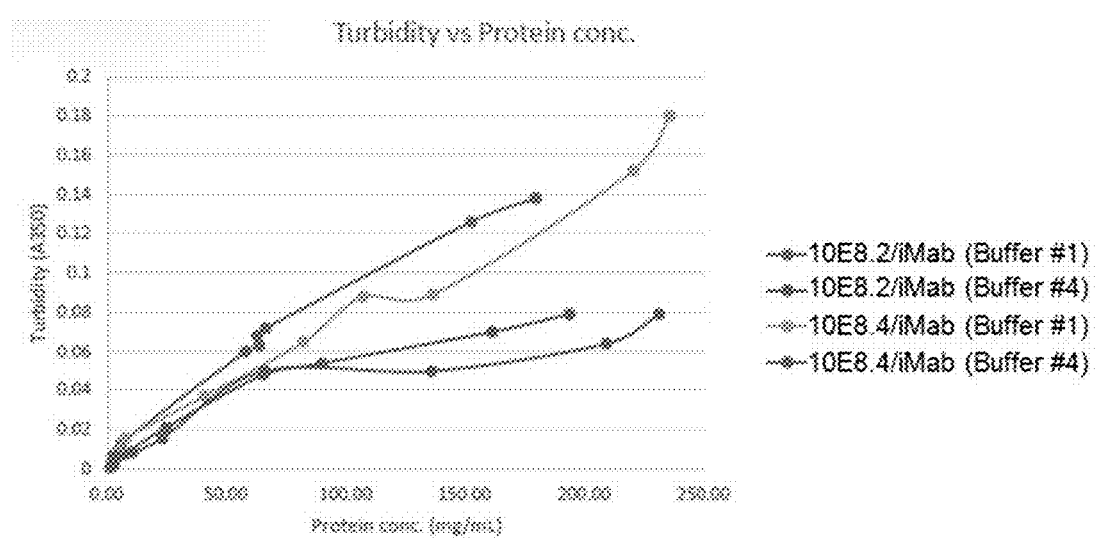
FIG. 40 demonstrates the turbidity of 10E8.2/iMab and the 10E8.4/iMab variant at different concentrations over time.

The turbidity characteristics of the 10E8.4/iMab antibody were also analyzed. In the analysis, the 10E8.2/iMab and 10E8.4/iMab antibodies were each buffer exchanged into target buffers and were concentrated via ultracentrifugation at 3000-5000 g, 4° C. Absorbance at 280 nm and 350 nm were measured over time using a NanoDrop 2000 spectrophotometer. All measurements were repeated twice with 2.5 μL sample each time and an average was taken, and protein concentration (A280) was plotted versus turbidity (A350) for similar timepoints during the ultracentrifugation process. As shown in FIG. 40, the turbidity of both 10E8.2/iMab and 10E8.4/iMab antibodies increased with protein concentration over time. In particular, the 10E8.2/iMab antibody showed higher turbidity than 10E8.4/iMab at the same protein concentrations over 100 mg/mL in both buffer conditions tested.

Figure 41:
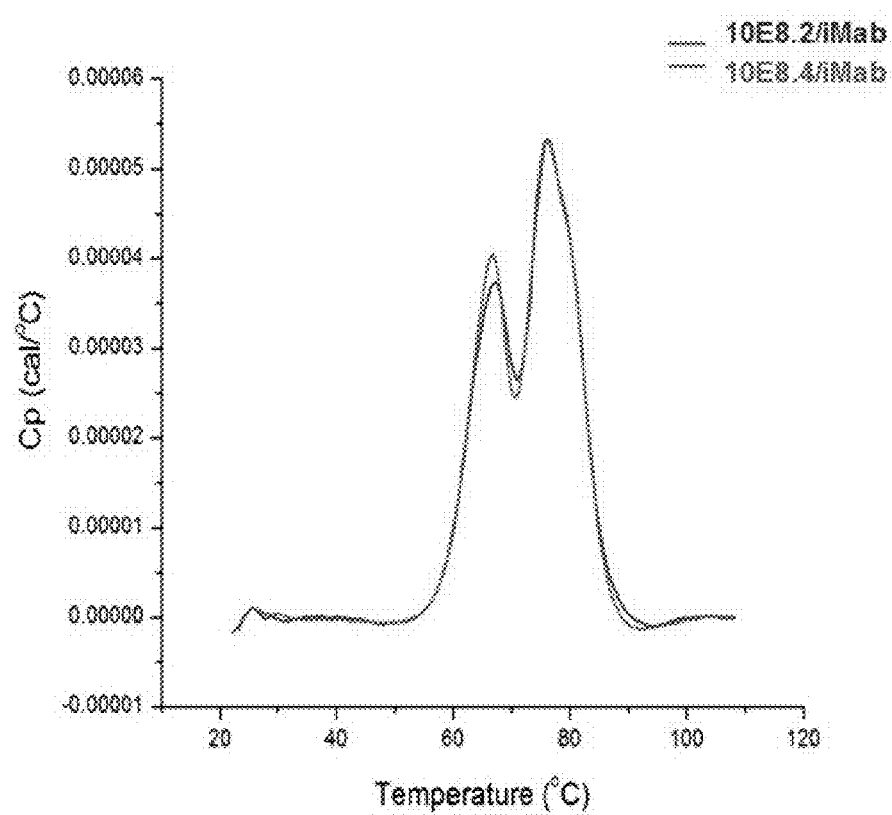
FIG. 41 shows the thermostability of 10E8.2/iMab and the 10E8.4/iMab variant as assessed by differential scanning calorimetry.

Additionally, the thermostability profile of the 10E8.4/iMab antibody was compared against the parental 10E8.2/iMab antibody using differential scanning calorimetry (DSC). DSC is a thermoanalytical technique in which the difference in the amount of heat required to increase the temperature of a sample and reference is measured as a function of temperature. Each peak in the thermogram corresponds to a heat effect associated with a specific process, such as crystallization or melting, and is an indication of the stability of a molecule as temperature is increased. To determine the thermostability of the 10E8.2/iMab and 10E8.4/iMab antibodies, each bispecific antibody was buffer exchanged into identical buffer compositions using ultra-filtration centrifugal devices under the condition of 4° C. and 3000-5000 g. The protein concentrations were then adjusted to ~10 mg/mL and aseptically filtered with 0.22-μm filter. Samples were then diluted to 1 mg/mL with reference buffers. Reference buffers (400 μL) were added into the odd-numbered wells of a 96-well plate and 400 μL of samples were added into the even-numbered wells of the same plate. The plates were scanned from 20° C. to 90° C. with a rate of 200° C./hr. Analysis of thermograms was performed with MicroCal VP-Capillary DSC Automated data analysis software. As shown in FIG. 41, both 10E8.2/iMab and 10E8.4/iMab antibodies exhibited similar thermostability when evaluated by DSC.

Figure 42:
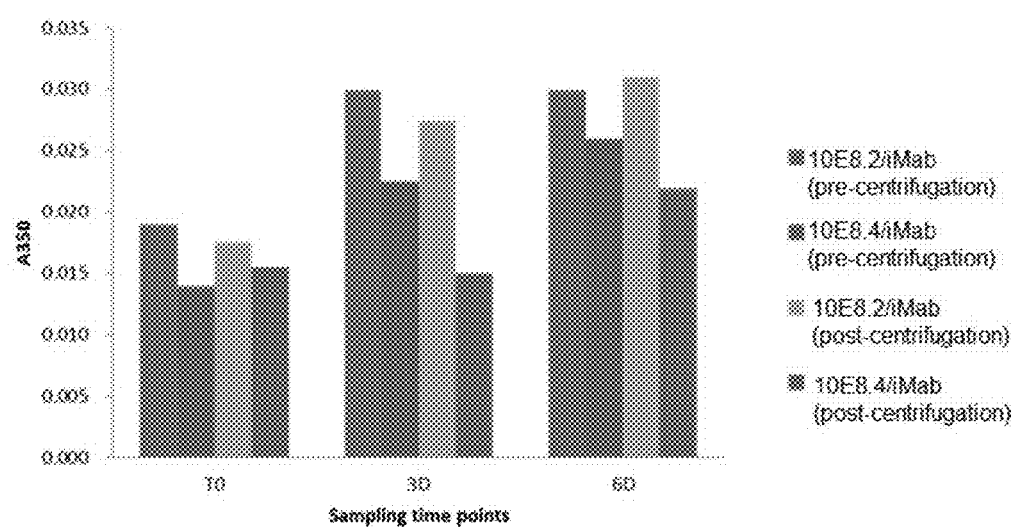
FIG. 42 demonstrates the turbidity of 10E8.2/iMab and the 10E8.4/iMab variant after forced degradation at 50° C. for six days. For each set of histograms, the bars from left to right represent 10E8.2/iMab (pre-centrifugation), 10E8.4/iMab (pre-centrifugation), 10E8.2/iMab (post-centrifugation), and 10E8.4/iMab (post-centrifugation).

FIG. 42 shows the results from a turbidity analysis after forced degradation of the 10E8.2/iMab and 10E8.4/iMab antibodies. The 10E8.2/iMab and 10E8.4/iMab antibodies were each buffer exchanged into identical buffer compositions using ultra-filtration centrifugal devices under the condition of 4° C. and 3000-5000 g. The protein concentrations were then adjusted to ~10 mg/mL and aseptically filtered with 0.22-μm filter. Samples were then incubated at 50° C. to induce forced degradation, and both pre-centrifugation and post-centrifugation samples of 10E8.2/iMab and 10E8.4/iMab were measured for development of turbidity by absorbance at 350 nm at 0 days, 3 days and 6 days after incubation began. Results indicate that the 10E8.2/iMab antibody exhibited overall higher turbidity than 10E8.4/iMab at all time points studied.

Molecule purity after forced degradation of the 10E8.2/iMab and 10E8.4/iMab antibodies was also assessed. The 10E8.2/iMab and 10E8.4/iMab antibodies were each buffer exchanged into two buffer compositions using ultra-filtration centrifugal devices under the condition of 4° C. and 3000-5000 g. The protein concentrations were then adjusted to ~10 mg/mL and aseptically filtered with 0.22-μm filter. Samples were then incubated at 50° C. to induce forced degradation, and the percentage of molecule purity by SDS-Gel Capillary Electrophoresis in non-reducing conditions was determined at 0 days, 3 days and 6 days after incubation began. To conduct SDS-Gel Capillary Electrophoresis, a denaturing solution was prepared by mixing sample buffer, 10% SDS and 100 mM N-Ethylmaleimide at 20:1:0.7 volume ratio. Two microliters of samples and 74, denaturing solution were mixed well, incubated at 70° C. for 10 mins and spun down. 35 μL $H_2O$ was added to the sample, then 42 μL of the mixture was transferred into 96-well plate and centrifuged at 4000 rpm for 20 mins to remove air bubbles. After the plate was loaded, samples were sipped, stained, separated and detected in the Microchip which was filled with destaining-gel, fluorescent dye and marker. The data was then analysed with LabChip GX Reviewer to determine the percentage of intact bispecific antibody molecule versus smaller antibody fragments in each sample. As indicated in Table 6 below, the 10E8.4/iMab antibody showed better intact molecule purity than the 10E8.2/iMab antibody in both buffers at all timepoints studied:

TABLE 6

| Formulation | Timepoint | Purity (%) 10E8.2/iMab | 10E8.4/iMab |
| --- | --- | --- | --- |
| Buffer #1 | T0 | 71.6 | 87.6 |
| Buffer #1 | 3 D | 77.3 | 87.2 |
| Buffer #1 | 6 D | 76.2 | 87.0 |
| Buffer #4 | T0 | 74.9 | 89.2 |
| Buffer #4 | 3 D | 81.9 | 92.6 |
| Buffer #4 | 6 D | 89.4 | 94.6 |

An aggregation analysis was also performed. Specifically, the 10E8.2/iMab and 10E8.4/iMab antibodies were each buffer exchanged into two buffer compositions using ultra-filtration centrifugal devices under the condition of 4° C. and 3000-5000 g. The protein concentrations were then adjusted to ~10 mg/mL and aseptically filtered with 0.22-μm filter. Samples were then incubated at 50° C. to induce forced degradation, and the high molecular weight (HMW) fraction in each protein sample was determined by SE-HPLC (size exclusion chromatography) as a measurement of aggregation. Size exclusion chromatography was performed using an Agilent 1260 Infinity system and a TSKGel G3000SWXL column (300×7.8 mm, 5 μm). The mobile phase was 50 mM PB, 300 mM NaCl, pH 7.0±0.2 and the flow rate was set as 1.0 mL/min. Samples were centrifuged (~10000 rpm for 2 min at 4° C.), injected and detected at 280 nm to determine the percentage of HMW in the samples. As shown in Table 7 below, although the 10E8.4/iMab antibody had a larger HMW population at T0, it showed a less rapid change in HMW percentage over time during incubation at the forced degradation-inducing conditions as compared to 10E8.2/iMab.

TABLE 7

| Formulation | Timepoint | HMW peak (%) | |
|---|---|---|---|
| | | 10E8.2/iMab | 10E8.4/iMab |
| Buffer #1 | T0 | 7.7 | 13.8 |
| Buffer #1 | 3 D | 39.2 | 27.2 |
| Buffer #1 | 6 D | 49.7 | 35.8 |
| Buffer #4 | T0 | 5.9 | 11.0 |
| Buffer #4 | 3 D | 37.1 | 25.0 |
| Buffer #4 | 6 D | 44.9 | 31.3 |

Figure 43:
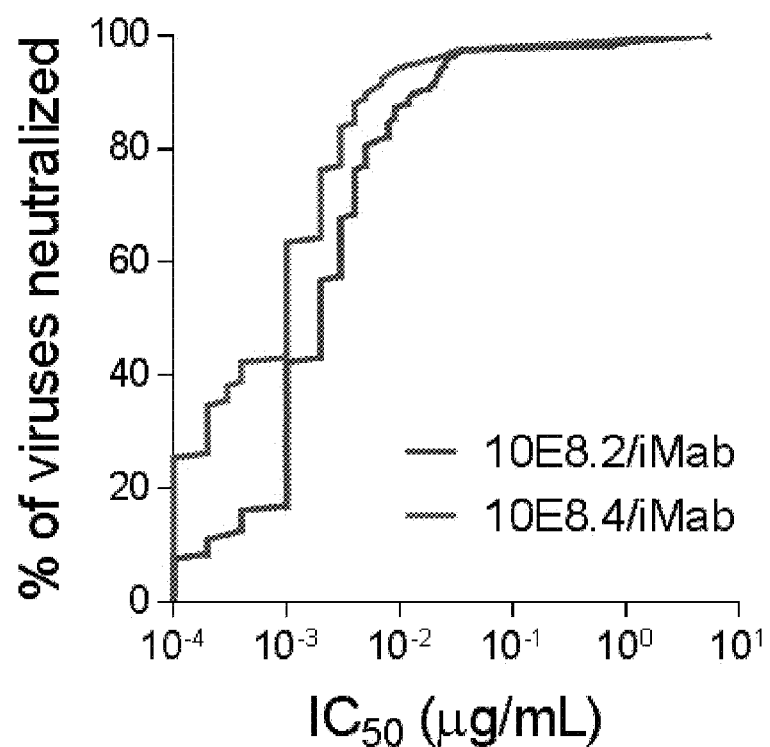
FIG. 43 shows the anti-HIV coverage of 10E8.2/iMab and the 10E8.4/iMab variant.

Additionally, as shown in FIG. 43, the functional activities of the 10E8.2/iMab and 10E8.4/iMab antibodies were compared in vitro. In particular, virus neutralization was assessed with a single cycle assay using TZM-bl cells and 118 HIV-1 tier-2 HIV-1 Env pseudoviruses representing diverse clades and origins as described previously (Seaman et al. 2010. J. Virol. 84, 1439-1452). Results indicate that, in addition to its improvement in solubility, decrease in turbidity and improvement in biophysical properties under thermal stress inducing conditions, the 10E8.4/iMab antibody also exhibited an approximately 2.5-fold enhancement in neutralization activity against a large panel of HIV-1 Env pseudotyped viruses as compared to 10E8.2/iMab.

Figure 44:
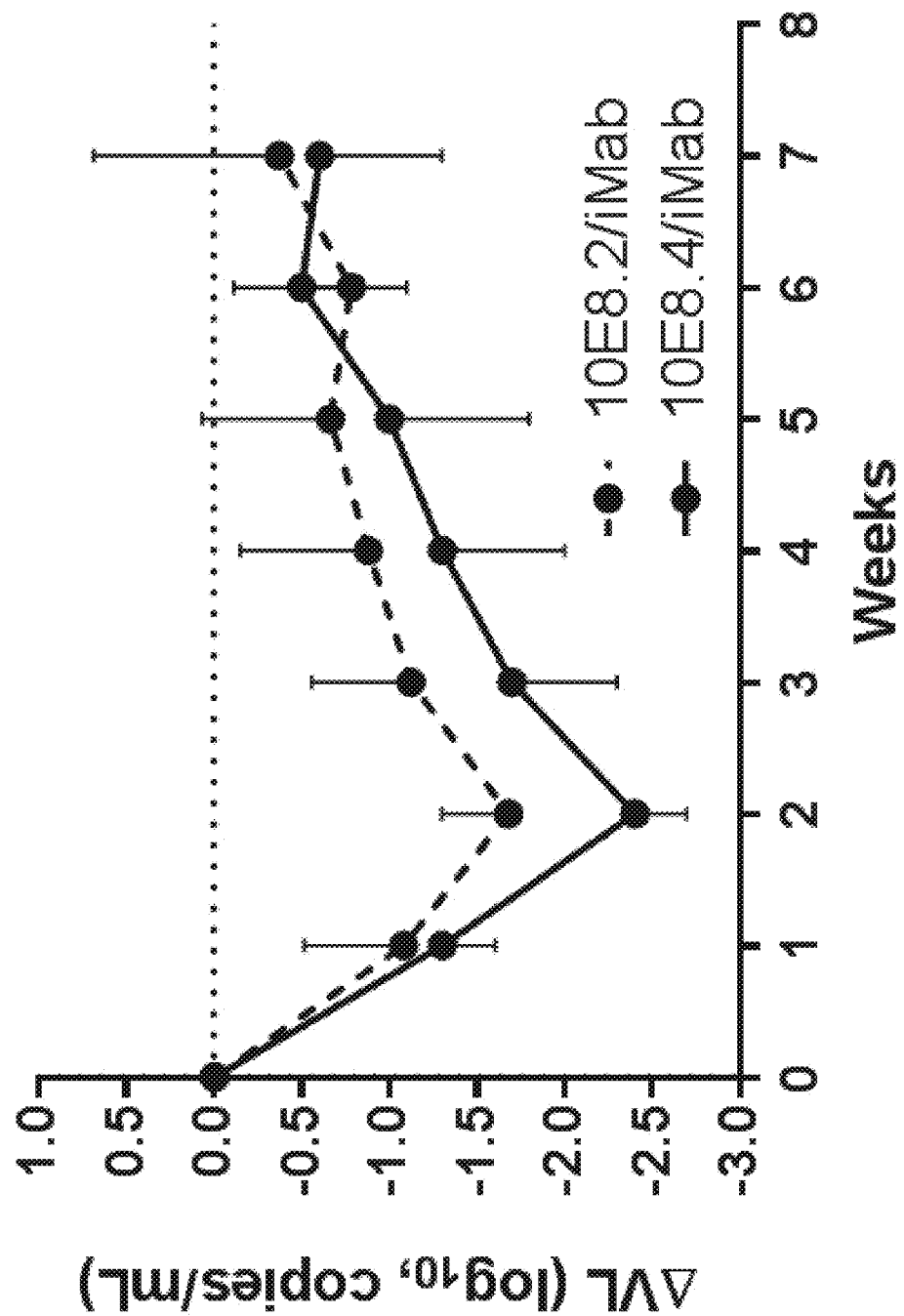
FIG. 44 is a graph showing the in vivo antiviral activity of 10E8.2/iMab and the 10E8.4/iMab variant in a humanized mouse model of HIV-1 infection.

The functional activities of the 10E8.2/iMab and 10E8.4/iMab antibodies were also compared in vivo. Immunodeficient NSG mice (NOD. Cg-Prkdc$^{scid}$ Il2rg$^{tm1wjl}$/SzJ) were reconstituted with human hematopoietic stem cells and infected with Tier-2 clade B HIV-1$_{JR-CSF}$ four weeks prior to the initiation of antibody treatment. Mice were then treated weekly with modified variants of 10E8.2/iMab or 10E8.4/iMab that allowed for their evaluation in humanized mice. As shown in FIG. 44, a maximum mean viral load reduction of ~1.7 log was observed in mice treated with 10E8.2/iMab, and a maximum mean viral load reduction of ~2.4 log was observed in mice treated with 10E8.4/iMab."

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

The invention claimed is:

1. A bispecific antibody in a CrossMab format capable of neutralizing HIV, wherein the antibody comprises a light chain and heavy chain portion of a first antibody 10E8, or a variant thereof, that binds to a HIV envelope protein, and a light chain and heavy chain portion of a second antibody ibalizumab, or a variant thereof, that binds to a cell membrane receptor protein or a cell membrane co-receptor protein, wherein
the light chain portion of the first antibody 10E8 comprises an amino acid sequence having at least 97% identity with SEQ ID NO: 46 and the heavy chain portion of the first antibody 10E8 comprises an amino acid sequence having at least 97% identity with SEQ ID NO: 47; and
the light chain portion of the second antibody ibalizumab comprises an amino acid sequence having at least 97% identity with SEQ ID NO: 1, and the heavy chain portion of the second antibody ibalizumab comprises an amino acid sequence having at least 97% with SEQ ID NO: 2; and wherein any variations relative to SEQ ID NOs:1, 2, 46 and 47 are outside the variable regions.

2. The bispecific antibody of claim 1, wherein the antibody comprises a light chain portion of an ibalizumab antibody comprising the amino acid sequence of SEQ ID NO: 1 and a heavy chain portion of an ibalizumab antibody comprising the amino acid sequence of SEQ ID NO: 2.

3. The bispecific antibody of claim 1, wherein the antibody comprises a light chain portion of a 10E8 antibody comprising the amino acid sequence of SEQ ID NO: 46 and a heavy chain portion of a 10E8 antibody comprising the amino acid sequence of SEQ ID NO: 47.

4. A pharmaceutical composition comprising the bispecific antibody of claim 1, and a pharmaceutically acceptable carrier.

5. The pharmaceutical composition of claim 4, wherein the composition is formulated for oral, intranasal, pulmonary, intradermal, transdermal, subcutaneous, intramuscular, intraperitoneal, or intravenous delivery.

* * * * *

SEQUENCE LISTING

```
<160> NUMBER OF SEQ ID NOS: 47

<210> SEQ ID NO 1
<211> LENGTH: 217
<212> TYPE: PRT
<213> ORGANISM: Artificial Sequence
<220> FEATURE:
<223> OTHER INFORMATION: Synthetic Peptide

<400> SEQUENCE: 1

Asp Ile Val Met Thr Gln Ser Pro Asp Ser Leu Ala Val Ser Leu Gly
 1               5                  10                  15

Glu Arg Val Thr Met Asn Cys Lys Ser Ser Gln Ser Leu Leu Tyr Ser
            20                  25                  30

Thr Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
```

```
                145                 150                 155                 160
            Thr Ser Gly Val His Thr Phe Pro Ala Val Leu Gln Ser Ser Gly Leu
                            165                 170                 175

Tyr Ser Leu Ser Ser Val Val Thr Val Pro Ser Ser Ser Leu Gly Thr
                            180                 185                 190

Gln Thr Tyr Ile Cys Asn Val Asn His Lys Pro Ser Asn Thr Lys Val
                            195                 200                 205

Asp Lys Lys Val Glu Pro Lys Ser Cys
                            210                 215

<210> SEQ ID NO 2
<211> LENGTH: 456
<212> TYPE: PRT
<213> ORGANISM: Artificial Sequence
<220> FEATURE:
<223> OTHER INFORMATION: Synthetic Peptide

<400> SEQUENCE: 2

Gln Val Gln Leu Gln Gln Ser Gly Pro Glu Val Val Lys Pro Gly Ala
1               5                   10                  15

Ser Val Lys Met Ser Cys Lys Ala Ser Gly Tyr Thr Phe Thr Ser Tyr
                20                  25                  30

Val Ile His Trp Val Arg Gln Lys Pro Gly Gln Gly Leu Asp Trp Ile
            35                  40                  45

Gly Tyr Ile Asn Pro Tyr Asn Asp Gly Thr Asp Tyr Asp Glu Lys Phe
        50                  55                  60

Lys Gly Lys Ala Thr Leu Thr Ser Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Lys Asp Asn Tyr Ala Thr Gly Ala Trp Phe Ala Tyr Trp
            100                 105                 110

Gly Gln Gly Thr Leu Val Thr Val Ser Ser Ala Ser Thr Ala Ala Pro
        115                 120                 125

Ser Val Phe Ile Phe Pro Pro Ser Asp Glu Gln Leu Lys Ser Gly Thr
130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
210                 215                 220

Asn Arg Gly Glu Cys Asp Lys Thr His Thr Cys Pro Pro Cys Pro Ala
225                 230                 235                 240

Pro Glu Phe Glu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
```

```
                    290                 295                 300
Tyr Asn Ser Thr Tyr Arg Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Ser Ile Glu Lys Thr Ile Ser Lys Ala Lys Gly Gln Pro
                340                 345                 350

Arg Glu Pro Gln Val Cys Thr Leu Pro Pro Ser Arg Asp Glu Leu Thr
            355                 360                 365

Lys Asn Gln Val Ser Leu Ser Cys Ala Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
                420                 425                 430

Ser Cys Ser Val Leu His Glu Ala Leu His Ser His Tyr Thr Gln Lys
            435                 440                 445

Ser Leu Ser Leu Ser Pro Gly Lys
        450                 455

<210> SEQ ID NO 3
<211> LENGTH: 219
<212> TYPE: PRT
<213> ORGANISM: Artificial Sequence
<220> FEATURE:
<223> OTHER INFORMATION: Synthetic Peptide

<400> SEQUENCE: 3

Glu Val Val Ile Thr Gln Ser Pro Leu Phe Leu Pro Val Thr Pro Gly
1               5                   10                  15

Glu Ala Ala Ser Leu Ser Cys Lys Cys Ser His Ser Leu Gln His Ser
                20                  25                  30

Thr Gly Ala Asn Tyr Leu Ala Trp Tyr Leu Gln Arg Pro Gly Gln Thr
            35                  40                  45

Pro Arg Leu Leu Ile His Leu Ala Thr His Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ser Asp Asp Val Gly Thr Tyr Tyr Cys Met Gln Gly
                85                  90                  95

Leu His Ser Pro Trp Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
```

```
            195                 200                 205
Pro Val Thr Lys Ser Phe Asn Arg Gly Glu Cys
    210                 215

<210> SEQ ID NO 4
<211> LENGTH: 470
<212> TYPE: PRT
<213> ORGANISM: Artificial Sequence
<220> FEATURE:
<223> OTHER INFORMATION: Synthetic Peptide

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Asn Ser Phe Ser Asn His
            20                  25                  30

Asp Val His Trp Val Arg Gln Ala Thr Gly Gln Gly Leu Glu Trp Met
        35                  40                  45

Gly Trp Met Ser His Glu Gly Asp Lys Thr Gly Leu Ala Gln Lys Phe
    50                  55                  60

Gln Gly Arg Val Thr Ile Thr Arg Asp Ser Gly Ala Ser Thr Val Tyr
65                  70                  75                  80

Met Glu Leu Arg Gly Leu Thr Ala Asp Thr Ala Ile Tyr Tyr Cys
                85                  90                  95

Leu Thr Gly Ser Lys His Arg Leu Arg Asp Tyr Phe Leu Tyr Asn Glu
            100                 105                 110

Tyr Gly Pro Asn Tyr Glu Glu Trp Gly Asp Tyr Leu Ala Thr Leu Asp
        115                 120                 125

Val Trp Gly His Gly Thr Ala Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Phe Glu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
```

```
            340                 345                 350
Ala Ser Ile Glu Lys Thr Ile Ser Lys Ala Lys Gly Gln Pro Arg Glu
        355                 360                 365

Pro Gln Val Tyr Thr Leu Pro Pro Cys Arg Asp Glu Leu Thr Lys Asn
    370                 375                 380

Gln Val Ser Leu Trp Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Leu His Glu Ala Leu His Ser His Tyr Thr Gln Lys Ser Leu
    450                 455                 460

Ser Leu Ser Pro Gly Lys
465                 470

<210> SEQ ID NO 5
<211> LENGTH: 210
<212> TYPE: PRT
<213> ORGANISM: Artificial Sequence
<220> FEATURE:
<223> OTHER INFORMATION: Synthetic Peptide

<400> SEQUENCE: 5

Asp Ile Gln Met Thr Gln Ser Pro Ser Ser Leu Ser Ala Ser Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45

Lys Leu Glu Arg Gly Val Pro Ser Arg Phe Ser Gly Arg Arg Trp Gly
 50                 55                  60

Gln Glu Tyr Asn Leu Thr Ile Asn Asn Leu Gln Pro Glu Asp Ile Ala
65                  70                  75                  80

Thr Tyr Phe Cys Gln Val Tyr Glu Phe Val Val Phe Gly Gln Gly Thr
                85                  90                  95

Lys Val Gln Val Asp Ile Lys Arg Thr Val Ala Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys Val Gln Trp
130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys
    210
```

<210> SEQ ID NO 6
<211> LENGTH: 453
<212> TYPE: PRT
<213> ORGANISM: Artificial Sequence
<220> FEATURE:
<223> OTHER INFORMATION: Synthetic Peptide

<400> SEQUENCE: 6

```
Gln Val Gln Leu Leu Gln Ser Gly Ala Ala Val Thr Lys Pro Gly Ala
1               5                   10                  15

Ser Val Arg Val Ser Cys Glu Ala Ser Gly Tyr Asn Ile Arg Asp Tyr
                20                  25                  30

Phe Ile His Trp Trp Arg Gln Ala Pro Gly Gln Gly Leu Gln Trp Val
            35                  40                  45

Gly Trp Ile Asn Pro Lys Thr Gly Gln Pro Asn Asn Pro Arg Gln Phe
50                  55                  60

Gln Gly Arg Val Ser Leu Thr Arg His Ala Ser Trp Asp Phe Asp Thr
65                  70                  75                  80

Phe Ser Phe Tyr Met Asp Leu Lys Ala Leu Arg Ser Asp Asp Thr Ala
                85                  90                  95

Val Tyr Phe Cys Ala Arg Gln Arg Ser Asp Tyr Trp Asp Phe Asp Val
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Phe
225                 230                 235                 240

Glu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
            355                 360                 365

Val Ser Leu Trp Cys Leu Val Lys Gly Phe Tyr Pro Ser Asp Ile Ala
```

```
                    370                 375                 380
Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Leu His Glu Ala Leu His Ser His Tyr Thr Gln Lys Ser Leu Ser
                435                 440                 445

Leu Ser Pro Gly Lys
            450

<210> SEQ ID NO 7
<211> LENGTH: 211
<212> TYPE: PRT
<213> ORGANISM: Artificial Sequence
<220> FEATURE:
<223> OTHER INFORMATION: Synthetic Peptide

<400> SEQUENCE: 7

Gln Ser Ala Leu Thr Gln Pro Pro Ser Ala Ser Gly Ser Pro Gly Gln
1               5                   10                  15

Ser Ile Thr Ile Ser Cys Thr Gly Thr Ser Asn Asn Phe Val Ser Trp
            20                  25                  30

Tyr Gln Gln His Ala Gly Lys Ala Pro Lys Leu Val Ile Tyr Asp Val
        35                  40                  45

Asn Lys Arg Pro Ser Gly Val Pro Asp Arg Phe Ser Gly Ser Lys Ser
50                  55                  60

Gly Asn Thr Ala Ser Leu Thr Val Ser Gly Leu Gln Thr Asp Asp Glu
65                  70                  75                  80

Ala Val Tyr Tyr Cys Gly Ser Leu Val Gly Asn Trp Asp Val Ile Phe
                85                  90                  95

Gly Gly Gly Thr Lys Leu Thr Val Leu Gly Gln Pro Lys Ala Ala Pro
            100                 105                 110

Ser Val Thr Leu Phe Pro Pro Ser Ser Glu Glu Leu Gln Ala Asn Lys
        115                 120                 125

Ala Thr Leu Val Cys Leu Ile Ser Asp Phe Tyr Pro Gly Ala Val Thr
    130                 135                 140

Val Ala Trp Lys Ala Asp Ser Ser Pro Val Lys Ala Gly Val Glu Thr
145                 150                 155                 160

Thr Thr Pro Ser Lys Gln Ser Asn Asn Lys Tyr Ala Ala Ser Ser Tyr
                165                 170                 175

Leu Ser Leu Thr Pro Glu Gln Trp Lys Ser His Arg Ser Tyr Ser Cys
            180                 185                 190

Gln Val Thr His Glu Gly Ser Thr Val Glu Lys Thr Val Ala Pro Thr
        195                 200                 205

Glu Cys Ser
    210

<210> SEQ ID NO 8
<211> LENGTH: 465
<212> TYPE: PRT
<213> ORGANISM: Artificial Sequence
<220> FEATURE:
<223> OTHER INFORMATION: Synthetic Peptide

<400> SEQUENCE: 8
```

Gln Pro Gln Leu Gln Glu Ser Gly Pro Thr Leu Val Glu Ala Ser Glu
1               5                   10                  15

Thr Leu Ser Leu Thr Cys Ala Val Ser Gly Asp Ser Thr Ala Ala Cys
            20                  25                  30

Asn Ser Phe Trp Gly Trp Val Arg Gln Pro Pro Gly Lys Gly Leu Glu
            35                  40                  45

Trp Val Gly Ser Leu Ser His Cys Ala Ser Tyr Trp Asn Arg Gly Trp
    50                  55                  60

Thr Tyr His Asn Pro Ser Leu Lys Ser Arg Leu Thr Leu Ala Leu Asp
65                  70                  75                  80

Thr Pro Lys Asn Leu Val Phe Leu Lys Leu Asn Ser Val Thr Ala Ala
            85                  90                  95

Asp Thr Ala Thr Tyr Tyr Cys Ala Arg Phe Gly Gly Glu Val Leu Arg
            100                 105                 110

Tyr Thr Asp Trp Pro Lys Pro Ala Trp Val Asp Leu Trp Gly Arg Gly
            115                 120                 125

Thr Leu Val Thr Val Ser Ser Ala Ser Thr Lys Gly Pro Ser Val Phe
130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
            165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
            195                 200                 205

Ser Ser Leu Gly Thr Gln Thr Tyr Ile Cys Asn Val Asn His Lys Pro
            210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Phe Glu Gly Gly Pro
            245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
            275                 280                 285

Pro Glu Val Lys Phe Asn Trp Tyr Val Asp Gly Val Glu Val His Asn
            290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
            325                 330                 335

Tyr Lys Cys Lys Val Ser Asn Lys Ala Leu Pro Ala Ser Ile Glu Lys
            340                 345                 350

Thr Ile Ser Lys Ala Lys Gly Gln Pro Arg Glu Pro Gln Val Tyr Thr
            355                 360                 365

Leu Pro Pro Cys Arg Asp Glu Leu Thr Lys Asn Gln Val Ser Leu Trp
            370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Lys Leu Thr Val Asp Lys

```
                420           425           430
Ser Arg Trp Gln Gln Gly Asn Val Phe Ser Cys Ser Val Leu His Glu
        435                 440                 445
Ala Leu His Ser His Tyr Thr Gln Lys Ser Leu Ser Leu Ser Pro Gly
    450                 455                 460
Lys
465

<210> SEQ ID NO 9
<211> LENGTH: 214
<212> TYPE: PRT
<213> ORGANISM: Artificial Sequence
<220> FEATURE:
<223> OTHER INFORMATION: Synthetic Peptide

<400> SEQUENCE: 9

Tyr Glu Leu Thr Gln Glu Thr Gly Val Ser Val Ala Leu Gly Arg Thr
1               5                  10                  15
Val Thr Ile Thr Cys Arg Gly Asp Ser Leu Arg Ser His Tyr Ala Ser
            20                  25                  30
Trp Tyr Gln Lys Lys Pro Gly Gln Ala Pro Ile Leu Leu Phe Tyr Gly
        35                  40                  45
Lys Asn Asn Arg Pro Ser Gly Val Pro Asp Arg Phe Ser Gly Ser Ala
    50                  55                  60
Ser Gly Asn Arg Ala Ser Leu Thr Ile Ser Gly Ala Gln Ala Glu Asp
65                  70                  75                  80
Asp Ala Glu Tyr Tyr Cys Ser Ser Arg Asp Lys Ser Gly Ser Arg Leu
                85                  90                  95
Ser Val Phe Gly Gly Gly Thr Lys Leu Thr Val Leu Ser Gln Pro Lys
            100                 105                 110
Ala Ala Pro Ser Val Thr Leu Phe Pro Pro Ser Ser Glu Glu Leu Gln
        115                 120                 125
Ala Asn Lys Ala Thr Leu Val Cys Leu Ile Ser Asp Phe Tyr Pro Gly
    130                 135                 140
Ala Val Thr Val Ala Trp Lys Ala Asp Ser Ser Pro Val Lys Ala Gly
145                 150                 155                 160
Val Glu Thr Thr Thr Pro Ser Lys Gln Ser Asn Asn Lys Tyr Ala Ala
                165                 170                 175
Ser Ser Tyr Leu Ser Leu Thr Pro Glu Gln Trp Lys Ser His Arg Ser
            180                 185                 190
Tyr Ser Cys Gln Val Thr His Glu Gly Ser Thr Val Glu Lys Thr Val
        195                 200                 205
Ala Pro Thr Glu Cys Ser
    210

<210> SEQ ID NO 10
<211> LENGTH: 461
<212> TYPE: PRT
<213> ORGANISM: Artificial Sequence
<220> FEATURE:
<223> OTHER INFORMATION: Synthetic Peptide

<400> SEQUENCE: 10

Glu Val Gln Leu Val Glu Ser Gly Gly Gly Leu Val Lys Pro Gly Gly
1               5                  10                  15
Ser Leu Arg Leu Ser Cys Ser Ala Ser Gly Phe Asp Phe Asp Asn Ala
            20                  25                  30
```

Trp Met Thr Trp Val Arg Gln Pro Gly Lys Gly Leu Glu Trp Val
         35                  40                  45

Gly Arg Ile Thr Gly Pro Gly Glu Gly Trp Ser Val Asp Tyr Ala Ala
 50                  55                  60

Pro Val Glu Gly Arg Phe Thr Ile Ser Arg Leu Asn Ser Ile Asn Phe
 65                  70                  75                  80

Leu Tyr Leu Glu Met Asn Asn Leu Arg Met Glu Asp Ser Gly Leu Tyr
                 85                  90                  95

Phe Cys Ala Arg Thr Gly Lys Tyr Tyr Asp Phe Trp Ser Gly Tyr Pro
                100                 105                 110

Pro Gly Glu Glu Tyr Phe Gln Asp Trp Gly Arg Gly Thr Leu Val Thr
                115                 120                 125

Val Ser Ser Ala Ser Thr Lys Gly Pro Ser Val Phe Pro Leu Ala Pro
130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
                180                 185                 190

Leu Tyr Ser Leu Ser Ser Val Val Thr Val Pro Ser Ser Ser Leu Gly
                195                 200                 205

Thr Gln Thr Tyr Ile Cys Asn Val Asn His Lys Pro Ser Asn Thr Lys
                210                 215                 220

Val Asp Lys Lys Val Glu Pro Lys Ser Cys Asp Lys Thr His Thr Cys
225                 230                 235                 240

Pro Pro Cys Pro Ala Pro Glu Phe Glu Gly Gly Pro Ser Val Phe Leu
                245                 250                 255

Phe Pro Pro Lys Pro Lys Asp Thr Leu Met Ile Ser Arg Thr Pro Glu
                260                 265                 270

Val Thr Cys Val Val Val Asp Val Ser His Glu Asp Pro Glu Val Lys
                275                 280                 285

Phe Asn Trp Tyr Val Asp Gly Val Glu Val His Asn Ala Lys Thr Lys
                290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Ser Ile Glu Lys Thr Ile Ser Lys
                340                 345                 350

Ala Lys Gly Gln Pro Arg Glu Pro Gln Val Tyr Thr Leu Pro Pro Cys
                355                 360                 365

Arg Asp Glu Leu Thr Lys Asn Gln Val Ser Leu Trp Cys Leu Val Lys
                370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
                420                 425                 430

Gln Gly Asn Val Phe Ser Cys Ser Val Leu His Glu Ala Leu His Ser
                435                 440                 445

His Tyr Thr Gln Lys Ser Leu Ser Leu Ser Pro Gly Lys

<210> SEQ ID NO 11
<211> LENGTH: 217
<212> TYPE: PRT
<213> ORGANISM: Artificial Sequence
<220> FEATURE:
<223> OTHER INFORMATION: Synthetic Peptide

<400> SEQUENCE: 11

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Arg Leu Leu Ser Ser
            20                  25                  30

Tyr Gly His Thr Tyr Leu His Trp Tyr Leu Gln Lys Pro Gly Gln Ser
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Leu Thr Phe Gly Gln Gly Thr Lys Val Glu Ile Lys
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys
    210                 215
```

<210> SEQ ID NO 12
<211> LENGTH: 456
<212> TYPE: PRT
<213> ORGANISM: Artificial Sequence
<220> FEATURE:
<223> OTHER INFORMATION: Synthetic Peptide

<400> SEQUENCE: 12

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Ser Asn Tyr
            20                  25                  30

Trp Ile Gly Trp Val Arg Gln Ala Pro Gly Lys Gly Leu Glu Trp Ile
        35                  40                  45

Gly Asp Ile Tyr Pro Gly Gly Asn Tyr Ile Arg Asn Asn Glu Lys Phe
    50                  55                  60

Lys Asp Lys Thr Thr Leu Ser Ala Asp Thr Ser Lys Asn Thr Ala Tyr
65                  70                  75                  80
```

```
Leu Gln Met Asn Ser Leu Lys Thr Glu Asp Thr Ala Val Tyr Tyr Cys
                 85                  90                  95

Gly Ser Ser Phe Gly Ser Asn Tyr Val Phe Ala Trp Phe Thr Tyr Trp
            100                 105                 110

Gly Gln Gly Thr Leu Val Thr Val Ser Ser Ala Ser Thr Ala Ala Pro
        115                 120                 125

Ser Val Phe Ile Phe Pro Pro Ser Asp Glu Gln Leu Lys Ser Gly Thr
130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
210                 215                 220

Asn Arg Gly Glu Cys Asp Lys Thr His Thr Cys Pro Pro Cys Pro Ala
225                 230                 235                 240

Pro Glu Phe Glu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Ser Ile Glu Lys Thr Ile Ser Lys Ala Lys Gly Gln Pro
            340                 345                 350

Arg Glu Pro Gln Val Cys Thr Leu Pro Pro Ser Arg Asp Glu Leu Thr
        355                 360                 365

Lys Asn Gln Val Ser Leu Ser Cys Ala Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Leu His Glu Ala Leu His Ser His Tyr Thr Gln Lys
        435                 440                 445

Ser Leu Ser Leu Ser Pro Gly Lys
    450                 455

<210> SEQ ID NO 13
<211> LENGTH: 212
<212> TYPE: PRT
<213> ORGANISM: Artificial Sequence
<220> FEATURE:
<223> OTHER INFORMATION: Synthetic Peptide
```

<400> SEQUENCE: 13

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
    50                  55                  60

Asn Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Gly Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys
    210

<210> SEQ ID NO 14
<211> LENGTH: 454
<212> TYPE: PRT
<213> ORGANISM: Artificial Sequence
<220> FEATURE:
<223> OTHER INFORMATION: Synthetic Peptide

<400> SEQUENCE: 14

Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Ala Ser Val Thr Val Ser Ser Ala Ser Thr Ala Ala Pro Ser Val
        115                 120                 125

```
Phe Ile Phe Pro Pro Ser Asp Glu Gln Leu Lys Ser Gly Thr Ala Ser
            130                 135                 140
Val Val Cys Leu Leu Asn Asn Phe Tyr Pro Arg Glu Ala Lys Val Gln
145                 150                 155                 160
Trp Lys Val Asp Asn Ala Leu Gln Ser Gly Asn Ser Gln Glu Ser Val
                165                 170                 175
Thr Glu Gln Asp Ser Lys Asp Ser Thr Tyr Ser Leu Ser Ser Thr Leu
            180                 185                 190
Thr Leu Ser Lys Ala Asp Tyr Glu Lys His Lys Val Tyr Ala Cys Glu
        195                 200                 205
Val Thr His Gln Gly Leu Ser Ser Pro Val Thr Lys Ser Phe Asn Arg
210                 215                 220
Gly Glu Cys Asp Lys Thr His Thr Cys Pro Pro Cys Pro Ala Pro Glu
225                 230                 235                 240
Phe Glu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Ser Ile Glu Lys Thr Ile Ser Lys Ala Lys Gly Gln Pro Arg Glu
            340                 345                 350
Pro Gln Val Cys Thr Leu Pro Pro Ser Arg Asp Glu Leu Thr Lys Asn
        355                 360                 365
Gln Val Ser Leu Ser Cys Ala Val Lys Gly Phe Tyr Pro Ser Asp Ile
370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Val Ser Lys
                405                 410                 415
Leu Thr Val Asp Lys Ser Arg Trp Gln Gln Gly Asn Val Phe Ser Cys
            420                 425                 430
Ser Val Leu His Glu Ala Leu His Ser His Tyr Thr Gln Lys Ser Leu
        435                 440                 445
Ser Leu Ser Pro Gly Lys
    450

<210> SEQ ID NO 15
<211> LENGTH: 214
<212> TYPE: PRT
<213> ORGANISM: Artificial Sequence
<220> FEATURE:
<223> OTHER INFORMATION: Synthetic Peptide

<400> SEQUENCE: 15

Ser Glu Leu Thr Gln Glu Thr Gly Val Ser Val Ala Leu Gly Arg Thr
1               5                   10                  15
Val Thr Ile Thr Cys Arg Gly Asp Ser Leu Arg Ser His Tyr Ala Ser
                20                  25                  30
```

```
Trp Tyr Gln Lys Lys Pro Gly Gln Ala Pro Ile Leu Leu Phe Tyr Gly
            35                  40                  45

Lys Asn Asn Arg Pro Ser Gly Ile His Asp Arg Phe Ser Gly Ser Ala
 50                  55                  60

Ser Gly Asn Arg Ala Ser Leu Thr Ile Ser Gly Ala Gln Ala Glu Asp
 65                  70                  75                  80

Asp Ala Glu Tyr Tyr Cys Ser Ser Arg Asp Lys Ser Gly Ser Arg Leu
                 85                  90                  95

Ser Val Phe Gly Gly Gly Thr Lys Leu Thr Val Leu Ser Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
            210

<210> SEQ ID NO 16
<211> LENGTH: 461
<212> TYPE: PRT
<213> ORGANISM: Artificial Sequence
<220> FEATURE:
<223> OTHER INFORMATION: Synthetic Peptide

<400> SEQUENCE: 16

Glu Val Gln Leu Val Glu Ser Gly Gly Asp Leu Val Lys Pro Gly Gly
1               5                   10                  15

Ser Leu Arg Leu Ser Cys Ser Ala Ser Gly Phe Ser Phe Lys Asn Thr
            20                  25                  30

Trp Met Thr Trp Val Arg Gln Ala Pro Gly Lys Gly Leu Glu Trp Val
            35                  40                  45

Gly Arg Ile Thr Gly Pro Gly Glu Gly Trp Thr Ser Asp Tyr Ala Ala
 50                  55                  60

Thr Val Gln Gly Arg Phe Thr Ile Ser Arg Asn Asn Met Ile Asp Met
65                   70                  75                  80

Leu Tyr Leu Glu Met Asn Arg Leu Arg Thr Asp Thr Gly Leu Tyr
                 85                  90                  95

Tyr Cys Val His Thr Glu Lys Tyr Tyr Asn Phe Trp Gly Gly Tyr Pro
            100                 105                 110

Pro Gly Glu Glu Tyr Phe Gln His Trp Gly Arg Gly Thr Leu Val Ile
            115                 120                 125

Val Ser Ser Ala Ser Thr Lys Gly Pro Ser Val Phe Pro Leu Ala Pro
130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175
```

-continued

Leu Thr Ser Gly Val His Thr Phe Pro Ala Val Leu Gln Ser Ser Gly
                180                 185                 190

Leu Tyr Ser Leu Ser Ser Val Val Thr Val Pro Ser Ser Ser Leu Gly
            195                 200                 205

Thr Gln Thr Tyr Ile Cys Asn Val Asn His Lys Pro Ser Asn Thr Lys
        210                 215                 220

Val Asp Lys Lys Val Glu Pro Lys Ser Cys Asp Lys Thr His Thr Cys
225                 230                 235                 240

Pro Pro Cys Pro Ala Pro Glu Phe Glu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Ser Ile Glu Lys Thr Ile Ser Lys
            340                 345                 350

Ala Lys Gly Gln Pro Arg Glu Pro Gln Val Tyr Thr Leu Pro Pro Cys
        355                 360                 365

Arg Asp Glu Leu Thr Lys Asn Gln Val Ser Leu Trp Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Leu His Glu Ala Leu His Ser
        435                 440                 445

His Tyr Thr Gln Lys Ser Leu Ser Leu Ser Pro Gly Lys
    450                 455                 460

<210> SEQ ID NO 17
<211> LENGTH: 215
<212> TYPE: PRT
<213> ORGANISM: Artificial Sequence
<220> FEATURE:
<223> OTHER INFORMATION: Synthetic Peptide

<400> SEQUENCE: 17

Glu Ile Val Leu Thr Gln Ser Pro Gly Thr Gln Ser Leu Ser Pro Gly
1               5                   10                  15

Glu Arg Ala Thr Leu Ser Cys Arg Ala Ser Gln Ser Val Gly Asn Asn
            20                  25                  30

Lys Leu Ala Trp Tyr Gln Gln Arg Pro Gly Gln Ala Pro Arg Leu Leu
        35                  40                  45

Ile Tyr Gly Ala Ser Ser Arg Pro Ser Gly Val Ala Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Gln Ser Leu
                85                  90                  95

Ser Thr Phe Gly Gln Gly Thr Lys Val Glu Val Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 18
<211> LENGTH: 457
<212> TYPE: PRT
<213> ORGANISM: Artificial Sequence
<220> FEATURE:
<223> OTHER INFORMATION: Synthetic Peptide

<400> SEQUENCE: 18

Gln Val Gln Leu Val Gln Ser Gly Ala Glu Val Lys Arg Pro Gly Ser
1               5                   10                  15

Ser Val Thr Val Ser Cys Lys Ala Ser Gly Gly Ser Phe Ser Thr Tyr
                20                  25                  30

Ala Leu Ser Trp Val Arg Gln Ala Pro Gly Arg Gly Leu Glu Trp Met
            35                  40                  45

Gly Gly Val Ile Pro Leu Leu Thr Ile Thr Asn Tyr Ala Pro Arg Phe
    50                  55                  60

Gln Gly Arg Ile Thr Ile Thr Ala Asp Arg Ser Thr Ser Thr Ala Tyr
65                  70                  75                  80

Leu Glu Leu Asn Ser Leu Arg Pro Glu Asp Thr Ala Val Tyr Tyr Cys
                85                  90                  95

Ala Arg Glu Gly Thr Thr Gly Ala Gly Trp Leu Gly Lys Pro Ile Gly
            100                 105                 110

Ala Phe Ala His Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

```
Val Glu Pro Lys Ser Cys Asp Lys Thr His Thr Cys Pro Pro Cys Pro
225                 230                 235                 240

Ala Pro Glu Phe Glu Gly Gly Pro Ser Val Phe Leu Phe Pro Pro Lys
            245                 250                 255

Pro Lys Asp Thr Leu Met Ile Ser Arg Thr Pro Glu Val Thr Cys Val
        260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
        290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Ser Ile Glu Lys Thr Ile Ser Lys Ala Lys Gly Gln
        340                 345                 350

Pro Arg Glu Pro Gln Val Tyr Thr Leu Pro Pro Cys Arg Asp Glu Leu
            355                 360                 365

Thr Lys Asn Gln Val Ser Leu Trp Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
        420                 425                 430

Phe Ser Cys Ser Val Leu His Glu Ala Leu His Ser His Tyr Thr Gln
            435                 440                 445

Lys Ser Leu Ser Leu Ser Pro Gly Lys
450                 455

<210> SEQ ID NO 19
<211> LENGTH: 212
<212> TYPE: PRT
<213> ORGANISM: Artificial Sequence
<220> FEATURE:
<223> OTHER INFORMATION: Synthetic Peptide

<400> SEQUENCE: 19

Glu Ile Val Leu Thr Gln Ser Pro Ala Thr Leu Ser Val Ser Pro Gly
1               5                   10                  15

Arg Arg Ala Thr Leu Ser Cys Arg Ala Ser Gln Ser Val Asn Thr Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln His Tyr Gly Ser Ser Pro Leu
                85                  90                  95

Thr Phe Gly Gly Gly Thr Lys Leu Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125
```

```
Gly Gly Thr Ala Ala Leu Gly Cys Leu Val Lys Asp Tyr Phe Pro Glu
            130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Leu Gly Thr Gln Thr Tyr Ile Cys
            180                 185                 190

Asn Val Asn His Lys Pro Ser Asn Thr Lys Val Asp Lys Lys Val Glu
                195                 200                 205

Pro Lys Ser Cys
        210

<210> SEQ ID NO 20
<211> LENGTH: 455
<212> TYPE: PRT
<213> ORGANISM: Artificial Sequence
<220> FEATURE:
<223> OTHER INFORMATION: Synthetic Peptide

<400> SEQUENCE: 20

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Pro Met His Trp Val Arg Gln Ala Pro Gly Lys Gly Leu Glu Trp Met
            35                  40                  45

Thr Val Ile Ser Ser Asp Gly Arg Asn Lys Tyr Tyr Pro Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Gly Gly Tyr His Asp Phe Trp Ser Gly Pro Asp Tyr Trp Gly
            100                 105                 110

Gln Gly Thr Leu Val Thr Val Ser Ser Ala Ser Thr Ala Ala Pro Ser
        115                 120                 125

Val Phe Ile Phe Pro Pro Ser Asp Glu Gln Leu Lys Ser Gly Thr Ala
    130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
            180                 185                 190

Leu Thr Leu Ser Lys Ala Asp Tyr Glu Lys His Lys Val Tyr Ala Cys
        195                 200                 205

Glu Val Thr His Gln Gly Leu Ser Ser Pro Val Thr Lys Ser Phe Asn
    210                 215                 220

Arg Gly Glu Cys Asp Lys Thr His Thr Cys Pro Pro Cys Pro Ala Pro
225                 230                 235                 240

Glu Phe Glu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270
```

```
Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Ser Ile Glu Lys Thr Ile Ser Lys Ala Lys Gly Gln Pro Arg
            340                 345                 350

Glu Pro Gln Val Cys Thr Leu Pro Pro Ser Arg Asp Glu Leu Thr Lys
        355                 360                 365

Asn Gln Val Ser Leu Ser Cys Ala Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Val Ser
                405                 410                 415

Lys Leu Thr Val Asp Lys Ser Arg Trp Gln Gln Gly Asn Val Phe Ser
            420                 425                 430

Cys Ser Val Leu His Glu Ala Leu His Ser His Tyr Thr Gln Lys Ser
        435                 440                 445

Leu Ser Leu Ser Pro Gly Lys
    450                 455

<210> SEQ ID NO 21
<211> LENGTH: 213
<212> TYPE: PRT
<213> ORGANISM: Artificial Sequence
<220> FEATURE:
<223> OTHER INFORMATION: Synthetic Peptide

<400> SEQUENCE: 21

Tyr Glu Leu Thr Gln Glu Thr Gly Val Ser Val Ala Leu Gly Arg Thr
1               5                   10                  15

Val Thr Ile Thr Cys Arg Gly Asp Ser Leu Arg Ser His Tyr Ala Ser
            20                  25                  30

Trp Tyr Gln Lys Lys Pro Gly Gln Ala Pro Ile Leu Leu Phe Tyr Gly
        35                  40                  45

Lys Asn Asn Arg Pro Ser Gly Val Pro Asp Arg Phe Ser Gly Ala Ser
    50                  55                  60

Gly Asn Arg Ala Ser Leu Thr Ile Ser Gly Ala Gln Ala Glu Asp Asp
65                  70                  75                  80

Ala Glu Tyr Tyr Cys Ser Ser Arg Asp Lys Ser Gly Ser Arg Leu Ser
                85                  90                  95

Val Phe Gly Gly Gly Thr Lys Leu Thr Val Leu Ser Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175
```

```
Ser Tyr Leu Ser Leu Thr Pro Glu Gln Trp Lys Ser His Arg Ser Tyr
        180                 185                 190

Ser Cys Gln Val Thr His Glu Gly Ser Thr Val Glu Lys Thr Val Ala
        195                 200                 205

Pro Thr Glu Cys Ser
        210

<210> SEQ ID NO 22
<211> LENGTH: 461
<212> TYPE: PRT
<213> ORGANISM: Artificial Sequence
<220> FEATURE:
<223> OTHER INFORMATION: Synthetic Peptide

<400> SEQUENCE: 22

Glu Val Gln Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Leu Asn Ser Ile Asn Phe
65                  70                  75                  80

Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Thr
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Phe Glu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320
```

```
Thr Val Leu His Gln Asp Trp Leu Asn Gly Lys Glu Tyr Lys Cys Lys
                325                 330                 335

Val Ser Asn Lys Ala Leu Pro Ala Ser Ile Glu Lys Thr Ile Ser Lys
            340                 345                 350

Ala Lys Gly Gln Pro Arg Glu Pro Gln Val Tyr Thr Leu Pro Pro Cys
        355                 360                 365

Arg Asp Glu Leu Thr Lys Asn Gln Val Ser Leu Trp Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Leu His Glu Ala Leu His Ser
        435                 440                 445

His Tyr Thr Gln Lys Ser Leu Ser Leu Ser Pro Gly Lys
    450                 455                 460

<210> SEQ ID NO 23
<211> LENGTH: 219
<212> TYPE: PRT
<213> ORGANISM: Artificial Sequence
<220> FEATURE:
<223> OTHER INFORMATION: Synthetic Peptide

<400> SEQUENCE: 23

Asp Ile Val Met Thr Gln Thr Pro Leu Ser Leu Ser Val Thr Pro Gly
1               5                   10                  15

Gln Pro Ala Ser Ile Ser Cys Lys Ser Ser Glu Ser Leu Arg Gln Ser
            20                  25                  30

Asn Gly Lys Thr Ser Leu Tyr Trp Tyr Arg Gln Lys Pro Gly Gln Ser
        35                  40                  45

Pro Gln Leu Leu Val Phe Glu Val Ser Asn Arg Phe Ser Gly Val Ser
    50                  55                  60

Asp Arg Phe Val Gly Ser Gly Ser Gly Thr Asp Phe Thr Leu Arg Ile
65                  70                  75                  80

Ser Arg Val Glu Ala Glu Asp Val Gly Phe Tyr Tyr Cys Met Gln Ser
                85                  90                  95

Lys Asp Phe Pro Leu Thr Phe Gly Gly Gly Thr Lys Val Asp Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 24
<211> LENGTH: 465
<212> TYPE: PRT
<213> ORGANISM: Artificial Sequence
<220> FEATURE:
<223> OTHER INFORMATION: Synthetic Peptide

<400> SEQUENCE: 24

Arg Val Gln Leu Val Glu Ser Gly Gly Gly Val Val Gln Pro Gly Lys
1               5                   10                  15

Ser Val Arg Leu Ser Cys Val Val Ser Asp Phe Pro Phe Ser Lys Tyr
            20                  25                  30

Pro Met Tyr Trp Val Arg Gln Ala Pro Gly Lys Gly Leu Glu Trp Val
        35                  40                  45

Ala Ala Ile Ser Gly Asp Ala Trp His Val Val Tyr Ser Asn Ser Val
    50                  55                  60

Gln Gly Arg Phe Leu Val Ser Arg Asp Asn Val Lys Asn Thr Leu Tyr
65                  70                  75                  80

Leu Glu Met Asn Ser Leu Lys Ile Glu Asp Thr Ala Val Tyr Arg Cys
                85                  90                  95

Ala Arg Met Phe Gln Glu Ser Gly Pro Pro Arg Leu Asp Arg Trp Ser
            100                 105                 110

Gly Arg Asn Tyr Tyr Tyr Ser Gly Met Asp Val Trp Gly Gln Gly
        115                 120                 125

Thr Thr Val Thr Val Ser Ser Ala Ser Thr Lys Gly Pro Ser Val Phe
130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Phe Glu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Ser Ile Glu Lys
            340                 345                 350

Thr Ile Ser Lys Ala Lys Gly Gln Pro Arg Glu Pro Gln Val Tyr Thr
        355                 360                 365
```

```
Leu Pro Pro Cys Arg Asp Glu Leu Thr Lys Asn Gln Val Ser Leu Trp
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
                420                 425                 430

Ser Arg Trp Gln Gln Gly Asn Val Phe Ser Cys Ser Val Leu His Glu
                435                 440                 445

Ala Leu His Ser His Tyr Thr Gln Lys Ser Leu Ser Leu Ser Pro Gly
    450                 455                 460

Lys
465

<210> SEQ ID NO 25
<211> LENGTH: 215
<212> TYPE: PRT
<213> ORGANISM: Artificial Sequence
<220> FEATURE:
<223> OTHER INFORMATION: Synthetic Peptide

<400> SEQUENCE: 25

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Phe Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Ala Arg Asp Ser Gly Val
        50                  55                  60

Pro Ala Arg Phe Thr Gly Ser Gly Ser Glu Thr Tyr Phe Thr Leu Thr
65                  70                  75                  80

Ile Ser Arg Val Gln Ala Glu Asp Leu Ala Val Tyr Tyr Cys Met Gln
                85                  90                  95

Ser Phe Asn Leu Arg Thr Phe Gly Gly Gly Thr Lys Leu Glu Ile Lys
                100                 105                 110

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
                180                 185                 190

Tyr Ile Cys Asn Val Asn His Lys Pro Ser Asn Thr Lys Val Asp Lys
            195                 200                 205

Lys Val Glu Pro Lys Ser Cys
    210                 215

<210> SEQ ID NO 26
<211> LENGTH: 454
<212> TYPE: PRT
<213> ORGANISM: Artificial Sequence
<220> FEATURE:
```

<223> OTHER INFORMATION: Synthetic Peptide

<400> SEQUENCE: 26

Glu Val Asn Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Asn
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Asp Tyr Ser Ala
    50                  55                  60

Ser Val Arg Gly Arg Phe Thr Ile Ser Arg Asp Asn Ser Gln Ser Ile
65                  70                  75                  80

Leu Tyr Leu Gln Met Asn Ala Leu Arg Ala Glu Asp Ser Ala Thr Tyr
                85                  90                  95

Tyr Cys Ala Arg Asp Val Gly Ser Asn Tyr Phe Asp Tyr Trp Gly Gln
            100                 105                 110

Gly Thr Thr Leu Thr Val Ser Ser Ala Ser Thr Ala Ala Pro Ser Val
            115                 120                 125

Phe Ile Phe Pro Pro Ser Asp Glu Gln Leu Lys Ser Gly Thr Ala Ser
130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
210                 215                 220

Gly Glu Cys Asp Lys Thr His Thr Cys Pro Pro Cys Pro Ala Pro Glu
225                 230                 235                 240

Phe Glu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Ser Ile Glu Lys Thr Ile Ser Lys Ala Lys Gly Gln Pro Arg Glu
            340                 345                 350

Pro Gln Val Cys Thr Leu Pro Pro Ser Arg Asp Glu Leu Thr Lys Asn
        355                 360                 365

Gln Val Ser Leu Ser Cys Ala Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

```
Thr Pro Pro Val Leu Asp Ser Asp Gly Ser Phe Phe Leu Val Ser Lys
                405                 410                 415

Leu Thr Val Asp Lys Ser Arg Trp Gln Gln Gly Asn Val Phe Ser Cys
            420                 425                 430

Ser Val Leu His Glu Ala Leu His Ser His Tyr Thr Gln Lys Ser Leu
        435                 440                 445

Ser Leu Ser Pro Gly Lys
        450
```

<210> SEQ ID NO 27
<211> LENGTH: 214
<212> TYPE: PRT
<213> ORGANISM: Artificial Sequence
<220> FEATURE:
<223> OTHER INFORMATION: Synthetic Peptide

<400> SEQUENCE: 27

```
Ser Glu Leu Thr Gln Asp Pro Ala Val Ser Val Ala Leu Gly Gln Thr
1               5                   10                  15

Val Arg Ile Thr Cys Arg Gly Asp Ser Leu Arg Ser His Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Ser Ser Arg Asp Lys Ser Gly Ser Arg Leu
                85                  90                  95

Ser Val Phe Gly Gly Gly Thr Lys Leu Thr Val Leu Ser Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 28
<211> LENGTH: 214
<212> TYPE: PRT
<213> ORGANISM: Artificial Sequence
<220> FEATURE:
<223> OTHER INFORMATION: Synthetic Peptide

<400> SEQUENCE: 28

```
Tyr Glu Leu Thr Gln Glu Thr Gly Val Ser Val Ala Leu Gly Arg Thr
1               5                   10                  15

Val Thr Ile Thr Cys Gln Gly Asp Ser Leu Arg Ser Tyr Tyr Ala Ser
            20                  25                  30
```

```
Trp Tyr Gln Lys Lys Pro Gly Gln Ala Pro Ile Leu Leu Phe Tyr Gly
            35                  40                  45

Lys Asn Asn Arg Pro Ser Gly Val Pro Asp Arg Phe Ser Gly Ser Ala
 50                  55                  60

Ser Gly Asn Arg Ala Ser Leu Thr Ile Ser Gly Ala Gln Ala Glu Asp
 65                  70                  75                  80

Asp Ala Glu Tyr Tyr Cys Asn Ser Arg Asp Ser Ser Gly Asn His Leu
                 85                  90                  95

Val Val Phe Gly Gly Gly Thr Lys Leu Thr Val Leu Ser Gln Pro Lys
                100                 105                 110

Ala Ala Pro Ser Val Thr Leu Phe Pro Pro Ser Ser Glu Glu Leu Gln
                115                 120                 125

Ala Asn Lys Ala Thr Leu Val Cys Leu Ile Ser Asp Phe Tyr Pro Gly
                130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
                180                 185                 190

Tyr Ser Cys Gln Val Thr His Glu Gly Ser Thr Val Glu Lys Thr Val
                195                 200                 205

Ala Pro Thr Glu Cys Ser
                210

<210> SEQ ID NO 29
<211> LENGTH: 215
<212> TYPE: PRT
<213> ORGANISM: Artificial Sequence
<220> FEATURE:
<223> OTHER INFORMATION: Synthetic Peptide

<400> SEQUENCE: 29

Ala Ser Glu Leu Thr Gln Asp Pro Ala Val Ser Val Ala Leu Lys Gln
 1               5                  10                  15

Thr Val Thr Ile Thr Cys Arg Gly Asp Ser Leu Arg Ser His Tyr Val
                 20                  25                  30

Ser Trp Tyr Gln Lys Lys Pro Gly Gln Ala Pro Val Leu Val Phe Tyr
            35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Ala Gly Ala Gln Ala Glu
 65                  70                  75                  80

Asp Asp Ala Asp Tyr Tyr Cys Ser Ser Arg Asp Lys Ser Gly Ser Arg
                 85                  90                  95

Leu Ser Val Phe Gly Gly Gly Thr Lys Leu Thr Val Leu Ser Gln Pro
                100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
                130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175
```

```
Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 30
<211> LENGTH: 461
<212> TYPE: PRT
<213> ORGANISM: Artificial Sequence
<220> FEATURE:
<223> OTHER INFORMATION: Synthetic Peptide

<400> SEQUENCE: 30

Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asn Phe Asp Asp Ala
            20                  25                  30

Trp Met Thr Trp Val Arg Gln Pro Pro Gly Lys Gly Leu Glu Trp Val
        35                  40                  45

Gly Arg Ile Ser Gly Pro Gly Glu Gly Trp Ser Val Asp Tyr Ala Glu
    50                  55                  60

Ser Val Lys Gly Arg Phe Thr Ile Ser Arg Leu Asn Ser Ile Asn Phe
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys His Tyr Asp Phe Trp Ser Gly Tyr Pro
            100                 105                 110

Pro Gly Glu Glu Tyr Phe Gln Asp Trp Gly Gln Gly Thr Leu Val Ile
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Phe Glu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320
```

```
Thr Val Leu His Gln Asp Trp Leu Asn Gly Lys Glu Tyr Lys Cys Lys
            325                 330                 335

Val Ser Asn Lys Ala Leu Pro Ala Ser Ile Glu Lys Thr Ile Ser Lys
        340                 345                 350

Ala Lys Gly Gln Pro Arg Glu Pro Gln Val Tyr Thr Leu Pro Pro Cys
    355                 360                 365

Arg Asp Glu Leu Thr Lys Asn Gln Val Ser Leu Trp Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
            405                 410                 415

Ser Phe Phe Leu Tyr Ser Lys Leu Thr Val Asp Lys Ser Arg Trp Gln
        420                 425                 430

Gln Gly Asn Val Phe Ser Cys Ser Val Leu His Glu Ala Leu His Ser
    435                 440                 445

His Tyr Thr Gln Lys Ser Leu Ser Leu Ser Pro Gly Lys
450                 455                 460

<210> SEQ ID NO 31
<211> LENGTH: 215
<212> TYPE: PRT
<213> ORGANISM: Artificial Sequence
<220> FEATURE:
<223> OTHER INFORMATION: Synthetic Peptide

<400> SEQUENCE: 31

Ala Ser Glu Leu Thr Gln Asp Pro Ala Val Ser Val Ala Leu Lys Gln
1               5                   10                  15

Thr Val Thr Ile Thr Cys Arg Gly Asp Ser Leu Arg Ser His Tyr Val
            20                  25                  30

Ser Trp Tyr Gln Lys Lys Pro Gly Gln Ala Pro Val Leu Val Phe Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Ala Gly Ala Gln Ala Glu
65                  70                  75                  80

Asp Asp Ala Asp Tyr Tyr Cys Ser Ser Arg Asp Lys Ser Gly Ser Arg
                85                  90                  95

Leu Ser Val Phe Gly Gly Gly Thr Lys Leu Thr Val Leu Ser Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

```
<210> SEQ ID NO 32
<211> LENGTH: 461
<212> TYPE: PRT
<213> ORGANISM: Artificial Sequence
<220> FEATURE:
<223> OTHER INFORMATION: Synthetic Peptide

<400> SEQUENCE: 32

Glu Val Arg Leu Val Glu Ser Gly Gly Leu Val Lys Pro Gly Gly
1               5                  10                  15

Ser Leu Arg Leu Ser Cys Ser Ala Ser Gly Phe Asn Phe Asp Asp Ala
            20                  25                  30

Trp Met Thr Trp Val Arg Gln Pro Pro Gly Lys Gly Leu Glu Trp Val
        35                  40                  45

Gly Arg Ile Ser Gly Pro Gly Glu Gly Trp Ser Val Asp Tyr Ala Glu
    50                  55                  60

Ser Val Lys Gly Arg Phe Thr Ile Ser Arg Leu Asn Ser Ile Asn Phe
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Gln Gly Thr Leu Val Ile
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Phe Glu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Ser Ile Glu Lys Thr Ile Ser Lys
            340                 345                 350

Ala Lys Gly Gln Pro Arg Glu Pro Gln Val Tyr Thr Leu Pro Pro Cys
        355                 360                 365
```

```
Arg Asp Glu Leu Thr Lys Asn Gln Val Ser Leu Trp Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
                420                 425                 430

Gln Gly Asn Val Phe Ser Cys Ser Val Leu His Glu Ala Leu His Ser
                435                 440                 445

His Tyr Thr Gln Lys Ser Leu Ser Leu Ser Pro Gly Lys
                450                 455                 460

<210> SEQ ID NO 33
<211> LENGTH: 215
<212> TYPE: PRT
<213> ORGANISM: Artificial Sequence
<220> FEATURE:
<223> OTHER INFORMATION: Synthetic Peptide

<400> SEQUENCE: 33

Ala Ser Glu Leu Thr Gln Asp Pro Ala Val Ser Val Ala Leu Lys Gln
1               5                   10                  15

Thr Val Thr Ile Thr Cys Arg Gly Asp Ser Leu Arg Ser His Tyr Ala
                20                  25                  30

Ser Trp Tyr Gln Lys Lys Pro Gly Gln Ala Pro Ile Leu Leu Phe Tyr
            35                  40                  45

Gly Lys Asn Asn Arg Pro Ser Gly Val Pro Asp Arg Phe Ser Gly Ser
50                  55                  60

Ala Ser Gly Asn Arg Ala Ser Leu Thr Ile Ser Gly Ala Gln Ala Glu
65                  70                  75                  80

Asp Asp Ala Glu Tyr Tyr Cys Ser Ser Arg Asp Lys Ser Gly Ser Arg
                85                  90                  95

Leu Ser Val Phe Gly Gly Gly Thr Lys Leu Thr Val Leu Ser Gln Pro
                100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
                180                 185                 190

Ser Tyr Ser Cys Gln Val Thr His Glu Gly Ser Thr Val Glu Lys Thr
            195                 200                 205

Val Ala Pro Thr Glu Cys Ser
210                 215

<210> SEQ ID NO 34
<211> LENGTH: 461
<212> TYPE: PRT
<213> ORGANISM: Artificial Sequence
<220> FEATURE:
<223> OTHER INFORMATION: Synthetic Peptide
```

<400> SEQUENCE: 34

```
Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asn Phe Asp Asp Ala
            20                  25                  30

Trp Met Thr Trp Val Arg Gln Pro Gly Lys Gly Leu Glu Trp Val
        35                  40                  45

Gly Arg Ile Ser Pro Gly Glu Gly Trp Ser Val Asp Tyr Ala Glu
    50                  55                  60

Ser Val Lys Gly Arg Phe Thr Ile Ser Arg Leu Asn Ser Ile Asn Phe
65              70                  75                  80

Leu Tyr Leu Glu Met Asn Asn Val Arg Thr Glu Asp Thr Gly Tyr Tyr
                85                  90                  95

Phe Cys Ala Arg Thr Gly Lys His Tyr Asp Phe Trp Ser Gly Tyr Pro
            100                 105                 110

Pro Gly Glu Glu Tyr Phe Gln Asp Trp Gly Gln Gly Thr Leu Val Ile
        115                 120                 125

Val Ser Ser Ala Ser Thr Lys Gly Pro Ser Val Phe Pro Leu Ala Pro
130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
210                 215                 220

Val Asp Lys Lys Val Glu Pro Lys Ser Cys Asp Lys Thr His Thr Cys
225                 230                 235                 240

Pro Pro Cys Pro Ala Pro Glu Phe Glu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Ser Ile Glu Lys Thr Ile Ser Lys
            340                 345                 350

Ala Lys Gly Gln Pro Arg Glu Pro Gln Val Tyr Thr Leu Pro Pro Cys
        355                 360                 365

Arg Asp Glu Leu Thr Lys Asn Gln Val Ser Leu Trp Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415
```

```
Ser Phe Phe Leu Tyr Ser Lys Leu Thr Val Asp Lys Ser Arg Trp Gln
            420                 425                 430

Gln Gly Asn Val Phe Ser Cys Ser Val Leu His Glu Ala Leu His Ser
            435                 440                 445

His Tyr Thr Gln Lys Ser Leu Ser Leu Ser Pro Gly Lys
            450                 455                 460

<210> SEQ ID NO 35
<211> LENGTH: 461
<212> TYPE: PRT
<213> ORGANISM: Artificial Sequence
<220> FEATURE:
<223> OTHER INFORMATION: Synthetic Peptide

<400> SEQUENCE: 35

Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asn Phe Asp Asp Ala
            20                  25                  30

Trp Met Thr Trp Val Arg Gln Pro Pro Gly Lys Gly Leu Glu Trp Val
            35                  40                  45

Gly Arg Ile Ser Gly Pro Gly Glu Gly Trp Ser Val Asp Tyr Ala Glu
    50                  55                  60

Ser Val Lys Gly Arg Phe Thr Ile Ser Arg Asp Asn Thr Lys Asn Thr
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys His Tyr Asp Phe Trp Ser Gly Tyr Pro
            100                 105                 110

Pro Gly Glu Glu Tyr Phe Gln Asp Trp Gly Gln Gly Thr Leu Val Ile
            115                 120                 125

Val Ser Ser Ala Ser Thr Lys Gly Pro Ser Val Phe Pro Leu Ala Pro
        130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Phe Glu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320
```

```
Thr Val Leu His Gln Asp Trp Leu Asn Gly Lys Glu Tyr Lys Cys Lys
                325                 330                 335

Val Ser Asn Lys Ala Leu Pro Ala Ser Ile Glu Lys Thr Ile Ser Lys
            340                 345                 350

Ala Lys Gly Gln Pro Arg Glu Pro Gln Val Tyr Thr Leu Pro Pro Cys
        355                 360                 365

Arg Asp Glu Leu Thr Lys Asn Gln Val Ser Leu Trp Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Leu His Glu Ala Leu His Ser
        435                 440                 445

His Tyr Thr Gln Lys Ser Leu Ser Leu Ser Pro Gly Lys
    450                 455                 460

<210> SEQ ID NO 36
<211> LENGTH: 461
<212> TYPE: PRT
<213> ORGANISM: Artificial Sequence
<220> FEATURE:
<223> OTHER INFORMATION: Synthetic Peptide

<400> SEQUENCE: 36

Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asn Phe Asp Asp Ala
            20                  25                  30

Trp Met Thr Trp Val Arg Gln Pro Pro Gly Lys Gly Leu Glu Trp Val
        35                  40                  45

Gly Arg Ile Ser Gly Pro Gly Glu Gly Trp Ser Val Asp Tyr Ala Glu
    50                  55                  60

Ser Val Lys Gly Arg Phe Thr Ile Ser Arg Leu Asn Ser Ile Asn Phe
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys His Tyr Asp Phe Trp Ser Gly Tyr Pro
            100                 105                 110

Pro Gly Glu Glu Tyr Phe Gln Asp Trp Gly Gln Gly Thr Lys Val Ile
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220
```

```
Val Asp Lys Lys Val Glu Pro Lys Ser Cys Asp Lys Thr His Thr Cys
225                 230                 235                 240

Pro Pro Cys Pro Ala Pro Glu Phe Glu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Ser Ile Glu Lys Thr Ile Ser Lys
            340                 345                 350

Ala Lys Gly Gln Pro Arg Glu Pro Gln Val Tyr Thr Leu Pro Pro Cys
        355                 360                 365

Arg Asp Glu Leu Thr Lys Asn Gln Val Ser Leu Trp Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Leu His Glu Ala Leu His Ser
        435                 440                 445

His Tyr Thr Gln Lys Ser Leu Ser Leu Ser Pro Gly Lys
    450                 455                 460

<210> SEQ ID NO 37
<211> LENGTH: 461
<212> TYPE: PRT
<213> ORGANISM: Artificial Sequence
<220> FEATURE:
<223> OTHER INFORMATION: Synthetic Peptide

<400> SEQUENCE: 37

Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asn Phe Asp Asp Ala
                20                  25                  30

Trp Met Thr Trp Val Arg Gln Pro Pro Gly Lys Gly Leu Glu Trp Val
            35                  40                  45

Gly Arg Ile Ser Gly Pro Gly Glu Gly Trp Ser Val Asp Tyr Ala Glu
        50                  55                  60

Ser Val Lys Gly Arg Phe Thr Ile Ser Arg Asp Asn Thr Lys Asn Thr
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys His Tyr Asp Phe Trp Ser Gly Tyr Pro
            100                 105                 110

Pro Gly Glu Glu Tyr Phe Gln Asp Trp Gly Gln Gly Thr Lys Val Ile
        115                 120                 125
```

Val Ser Ser Ala Ser Thr Lys Gly Pro Ser Val Phe Pro Leu Ala Pro
            130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Phe Glu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Ser Ile Glu Lys Thr Ile Ser Lys
            340                 345                 350

Ala Lys Gly Gln Pro Arg Glu Pro Gln Val Tyr Thr Leu Pro Pro Cys
        355                 360                 365

Arg Asp Glu Leu Thr Lys Asn Gln Val Ser Leu Trp Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Leu His Glu Ala Leu His Ser
        435                 440                 445

His Tyr Thr Gln Lys Ser Leu Ser Leu Ser Pro Gly Lys
    450                 455                 460

<210> SEQ ID NO 38
<211> LENGTH: 217
<212> TYPE: PRT
<213> ORGANISM: Artificial Sequence
<220> FEATURE:
<223> OTHER INFORMATION: Synthetic Peptide

<400> SEQUENCE: 38

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Leu Tyr Ser
            20                  25                  30

```
Thr Asn Gln Lys Asn Tyr Leu Ala Trp Tyr Gln Gln Lys Pro Gly Gln
             35                  40                  45

Ser Pro Lys Leu Leu Ile Tyr Trp Ala Asn Ser Thr Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Val Ala Val Tyr Tyr Cys Gln Gln
                 85                  90                  95

Tyr Tyr Ser Tyr Arg Thr Phe Gly Gly Gly Thr Lys Leu Glu Ile Lys
                100                 105                 110

Ser Ser Ala Ser Thr Lys Gly Pro Ser Val Phe Pro Leu Ala Pro Ser
                115                 120                 125

Ser Lys Ser Thr Ser Gly Gly Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                    165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
            195                 200                 205

Asp Lys Lys Val Glu Pro Lys Ser Cys
210                 215

<210> SEQ ID NO 39
<211> LENGTH: 461
<212> TYPE: PRT
<213> ORGANISM: Artificial Sequence
<220> FEATURE:
<223> OTHER INFORMATION: Synthetic Peptide

<400> SEQUENCE: 39

Glu Val Arg Leu Val Glu Ser Gly Gly Gly Leu Val Lys Pro Gly Gly
1               5                  10                  15

Ser Leu Arg Leu Ser Cys Ser Ala Ser Gly Phe Asn Phe Asp Asp Ala
                20                  25                  30

Trp Met Thr Trp Val Arg Gln Pro Pro Gly Lys Gly Leu Glu Trp Val
             35                  40                  45

Gly Arg Ile Ser Gly Pro Gly Glu Gly Trp Ser Val Asp Tyr Ala Glu
 50                  55                  60

Ser Val Lys Gly Arg Phe Thr Ile Ser Arg Asp Asn Thr Lys Asn Thr
 65                  70                  75                  80

Leu Tyr Leu Glu Met Asn Asn Val Arg Thr Glu Asp Thr Gly Tyr Tyr
                 85                  90                  95

Phe Cys Ala Arg Thr Gly Lys His Tyr Asp Phe Trp Ser Gly Tyr Pro
                100                 105                 110

Pro Gly Glu Glu Tyr Phe Gln Asp Trp Gly Gln Gly Thr Lys Val Ile
            115                 120                 125

Val Ser Ser Ala Ser Thr Lys Gly Pro Ser Val Phe Pro Leu Ala Pro
            130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175
```

```
Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Phe Glu Gly Gly Pro Ser Val Phe Leu
            245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
            275                 280                 285

Phe Asn Trp Tyr Val Asp Gly Val Glu Val His Asn Ala Lys Thr Lys
        290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
            325                 330                 335

Val Ser Asn Lys Ala Leu Pro Ala Ser Ile Glu Lys Thr Ile Ser Lys
            340                 345                 350

Ala Lys Gly Gln Pro Arg Glu Pro Gln Val Tyr Thr Leu Pro Pro Cys
        355                 360                 365

Arg Asp Glu Leu Thr Lys Asn Gln Val Ser Leu Trp Cys Leu Val Lys
            370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
            405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Leu His Glu Ala Leu His Ser
        435                 440                 445

His Tyr Thr Gln Lys Ser Leu Ser Leu Ser Pro Gly Lys
    450                 455                 460

<210> SEQ ID NO 40
<211> LENGTH: 461
<212> TYPE: PRT
<213> ORGANISM: Artificial Sequence
<220> FEATURE:
<223> OTHER INFORMATION: Synthetic Peptide

<400> SEQUENCE: 40

Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asn Phe Asp Asp Ala
            20                  25                  30

Trp Met Thr Trp Val Arg Gln Pro Pro Gly Lys Gly Leu Glu Trp Val
        35                  40                  45

Gly Arg Ile Ser Gly Pro Gly Glu Gly Trp Ser Val Asp Tyr Ala Glu
    50                  55                  60

Ser Val Lys Gly Arg Phe Thr Ile Ser Arg Lys Asn Ser Ile Asn Thr
65                  70                  75                  80
```

```
Leu Tyr Leu Glu Met Asn Asn Val Arg Thr Glu Asp Thr Gly Tyr Tyr
                 85                  90                  95

Phe Cys Ala Arg Thr Gly Lys His Tyr Asp Phe Trp Ser Gly Tyr Pro
            100                 105                 110

Pro Gly Glu Glu Tyr Phe Gln Asp Trp Gly Gln Gly Thr Lys Val Ile
        115                 120                 125

Val Ser Ser Ala Ser Thr Lys Gly Pro Ser Val Phe Pro Leu Ala Pro
130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Phe Glu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Ser Ile Glu Lys Thr Ile Ser Lys
            340                 345                 350

Ala Lys Gly Gln Pro Arg Glu Pro Gln Val Tyr Thr Leu Pro Pro Cys
        355                 360                 365

Arg Asp Glu Leu Thr Lys Asn Gln Val Ser Leu Trp Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Leu His Glu Ala Leu His Ser
        435                 440                 445

His Tyr Thr Gln Lys Ser Leu Ser Leu Ser Pro Gly Lys
    450                 455                 460

<210> SEQ ID NO 41
<211> LENGTH: 461
<212> TYPE: PRT
<213> ORGANISM: Artificial Sequence
<220> FEATURE:
```

<223> OTHER INFORMATION: Synthetic Peptide

<400> SEQUENCE: 41

```
Glu Val Arg Leu Val Glu Ser Gly Gly Gly Leu Val Lys Pro Gly Gly
  1               5                  10                  15

Ser Leu Arg Leu Ser Cys Ser Ala Ser Gly Phe Asn Phe Asp Asp Ala
             20                  25                  30

Trp Met Thr Trp Val Arg Gln Pro Pro Gly Lys Gly Leu Glu Trp Val
         35                  40                  45

Gly Arg Ile Ser Gly Pro Gly Glu Gly Trp Ser Val Asp Tyr Ala Glu
     50                  55                  60

Ser Val Lys Gly Arg Phe Thr Ile Ser Arg Asp Asn Ser Ile Asn Thr
 65                  70                  75                  80

Leu Tyr Leu Glu Met Asn Asn Val Arg Thr Glu Asp Thr Gly Tyr Tyr
                 85                  90                  95

Phe Cys Ala Arg Thr Gly Lys His Tyr Asp Phe Trp Ser Gly Tyr Pro
            100                 105                 110

Pro Gly Glu Glu Tyr Phe Gln Asp Trp Gly Gln Gly Thr Lys Val Ile
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Phe Glu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Ser Ile Glu Lys Thr Ile Ser Lys
            340                 345                 350

Ala Lys Gly Gln Pro Arg Glu Pro Gln Val Tyr Thr Leu Pro Pro Cys
        355                 360                 365

Arg Asp Glu Leu Thr Lys Asn Gln Val Ser Leu Trp Cys Leu Val Lys
    370                 375                 380

Gly Phe Tyr Pro Ser Asp Ile Ala Val Glu Trp Glu Ser Asn Gly Gln
385                 390                 395                 400
```

```
Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Leu His Glu Ala Leu His Ser
        435                 440                 445

His Tyr Thr Gln Lys Ser Leu Ser Leu Ser Pro Gly Lys
    450                 455                 460

<210> SEQ ID NO 42
<211> LENGTH: 461
<212> TYPE: PRT
<213> ORGANISM: Artificial Sequence
<220> FEATURE:
<223> OTHER INFORMATION: Synthetic Peptide

<400> SEQUENCE: 42

Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asn Phe Asp Asp Ala
            20                  25                  30

Trp Met Thr Trp Val Arg Gln Pro Pro Gly Lys Gly Leu Glu Trp Val
        35                  40                  45

Gly Arg Ile Ser Gly Pro Gly Glu Gly Trp Ser Val Asp Tyr Ala Glu
    50                  55                  60

Ser Val Lys Gly Arg Phe Thr Ile Ser Arg Lys Asn Ser Lys Asn Thr
65                  70                  75                  80

Leu Tyr Leu Glu Met Asn Asn Val Arg Thr Asp Thr Gly Tyr Tyr
                85                  90                  95

Phe Cys Ala Arg Thr Gly Lys His Tyr Asp Phe Trp Ser Gly Tyr Pro
            100                 105                 110

Pro Gly Glu Glu Tyr Phe Gln Asp Trp Gly Gln Gly Thr Lys Val Ile
            115                 120                 125

Val Ser Ser Ala Ser Thr Lys Gly Pro Ser Val Phe Pro Leu Ala Pro
130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
            165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Phe Glu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300
```

```
Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Ser Ile Glu Lys Thr Ile Ser Lys
            340                 345                 350

Ala Lys Gly Gln Pro Arg Glu Pro Gln Val Tyr Thr Leu Pro Pro Cys
        355                 360                 365

Arg Asp Glu Leu Thr Lys Asn Gln Val Ser Leu Trp Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Leu His Glu Ala Leu His Ser
        435                 440                 445

His Tyr Thr Gln Lys Ser Leu Ser Leu Ser Pro Gly Lys
    450                 455                 460
```

<210> SEQ ID NO 43
<211> LENGTH: 461
<212> TYPE: PRT
<213> ORGANISM: Artificial Sequence
<220> FEATURE:
<223> OTHER INFORMATION: Synthetic Peptide

<400> SEQUENCE: 43

```
Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asn Phe Asp Asp Ala
            20                  25                  30

Trp Met Thr Trp Val Arg Gln Pro Pro Gly Lys Gly Leu Glu Trp Val
        35                  40                  45

Gly Arg Ile Ser Gly Pro Gly Glu Gly Trp Ser Val Asp Tyr Ala Glu
    50                  55                  60

Ser Val Lys Gly Arg Phe Thr Ile Ser Arg Asp Asn Ser Lys Asn Thr
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys His Tyr Asp Phe Trp Ser Gly Tyr Pro
            100                 105                 110

Pro Gly Glu Glu Tyr Phe Gln Asp Trp Gly Gln Gly Thr Lys Val Ile
        115                 120                 125

Val Ser Ser Ala Ser Thr Lys Gly Pro Ser Val Phe Pro Leu Ala Pro
130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205
```

Thr Gln Thr Tyr Ile Cys Asn Val Asn His Lys Pro Ser Asn Thr Lys
210                 215                 220

Val Asp Lys Lys Val Glu Pro Lys Ser Cys Asp Lys Thr His Thr Cys
225                 230                 235                 240

Pro Pro Cys Pro Ala Pro Glu Phe Glu Gly Gly Pro Ser Val Phe Leu
            245                 250                 255

Phe Pro Pro Lys Pro Lys Asp Thr Leu Met Ile Ser Arg Thr Pro Glu
        260                 265                 270

Val Thr Cys Val Val Val Asp Val Ser His Glu Asp Pro Glu Val Lys
    275                 280                 285

Phe Asn Trp Tyr Val Asp Gly Val Glu Val His Asn Ala Lys Thr Lys
290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
            325                 330                 335

Val Ser Asn Lys Ala Leu Pro Ala Ser Ile Glu Lys Thr Ile Ser Lys
        340                 345                 350

Ala Lys Gly Gln Pro Arg Glu Pro Gln Val Tyr Thr Leu Pro Pro Cys
    355                 360                 365

Arg Asp Glu Leu Thr Lys Asn Gln Val Ser Leu Trp Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
            405                 410                 415

Ser Phe Phe Leu Tyr Ser Lys Leu Thr Val Asp Lys Ser Arg Trp Gln
        420                 425                 430

Gln Gly Asn Val Phe Ser Cys Ser Val Leu His Glu Ala Leu His Ser
    435                 440                 445

His Tyr Thr Gln Lys Ser Leu Ser Leu Ser Pro Gly Lys
450                 455                 460

<210> SEQ ID NO 44
<211> LENGTH: 215
<212> TYPE: PRT
<213> ORGANISM: Artificial Sequence
<220> FEATURE:
<223> OTHER INFORMATION: Synthetic Peptide

<400> SEQUENCE: 44

Ala Ser Glu Leu Thr Gln Asp Pro Ala Val Ser Val Ala Leu Lys Gln
1               5                   10                  15

Thr Val Thr Ile Thr Cys Arg Gly Asp Ser Leu Arg Ser His Tyr Ala
            20                  25                  30

Ser Trp Tyr Gln Lys Lys Thr Gly Gln Ala Pro Lys Leu Leu Phe Tyr
        35                  40                  45

Gly Lys Asn Asn Arg Pro Ser Gly Val Pro Asp Arg Phe Ser Gly Ser
    50                  55                  60

Ala Ser Gly Asn Arg Ala Ser Leu Thr Ile Ser Gly Ala Gln Ala Glu
65                  70                  75                  80

Asp Asp Ala Glu Tyr Tyr Cys Ser Ser Arg Asp Lys Ser Gly Ser Arg
            85                  90                  95

Leu Ser Val Phe Gly Gly Gly Thr Lys Leu Thr Val Leu Ser Gln Pro
        100                 105                 110

```
Lys Ala Ala Pro Ser Val Thr Leu Phe Pro Pro Ser Ser Glu Glu Leu
            115                 120                 125
Gln Ala Asn Lys Ala Thr Leu Val Cys Leu Ile Ser Asp Phe Tyr Pro
        130                 135                 140
Gly Ala Val Thr Val Ala Trp Lys Ala Asp Ser Ser Pro Val Lys Ala
145                 150                 155                 160
Gly Val Glu Thr Thr Thr Pro Ser Lys Gln Ser Asn Asn Lys Tyr Ala
                165                 170                 175
Ala Ser Ser Tyr Leu Ser Leu Thr Pro Glu Gln Trp Lys Ser His Arg
            180                 185                 190
Ser Tyr Ser Cys Gln Val Thr His Glu Gly Ser Thr Val Glu Lys Thr
        195                 200                 205
Val Ala Pro Thr Glu Cys Ser
    210                 215

<210> SEQ ID NO 45
<211> LENGTH: 461
<212> TYPE: PRT
<213> ORGANISM: Artificial Sequence
<220> FEATURE:
<223> OTHER INFORMATION: Synthetic Peptide

<400> SEQUENCE: 45

Glu Val Arg Leu Val Glu Ser Gly Gly Gly Leu Val Lys Pro Gly Gly
1               5                   10                  15
Ser Leu Arg Leu Ser Cys Ser Ala Ser Gly Phe Asn Phe Asp Asp Ala
            20                  25                  30
Trp Met Thr Trp Val Arg Gln Pro Pro Gly Lys Gly Leu Glu Trp Val
        35                  40                  45
Gly Arg Ile Ser Gly Pro Gly Glu Gly Trp Ser Val Asp Tyr Ala Glu
    50                  55                  60
Ser Val Lys Gly Arg Phe Thr Ile Ser Arg Asp Asn Ser Lys Asn Thr
65                  70                  75                  80
Leu Tyr Leu Glu Met Asn Asn Val Arg Thr Glu Asp Thr Gly Tyr Tyr
                85                  90                  95
Phe Cys Ala Arg Thr Gly Lys His Tyr Asp Phe Trp Ser Gly Tyr Pro
            100                 105                 110
Pro Gly Glu Glu Tyr Phe Gln Asp Trp Gly Gln Gly Thr Lys Val Ile
        115                 120                 125
Val Ser Ser Ala Ser Thr Lys Gly Pro Ser Val Phe Pro Leu Ala Pro
    130                 135                 140
Ser Ser Lys Ser Thr Ser Gly Gly Thr Ala Ala Leu Gly Cys Leu Val
145                 150                 155                 160
Lys Asp Tyr Phe Pro Glu Pro Val Thr Val Ser Trp Asn Ser Gly Ala
                165                 170                 175
Leu Thr Ser Gly Val His Thr Phe Pro Ala Val Leu Gln Ser Ser Gly
            180                 185                 190
Leu Tyr Ser Leu Ser Ser Val Val Thr Val Pro Ser Ser Ser Leu Gly
        195                 200                 205
Thr Gln Thr Tyr Ile Cys Asn Val Asn His Lys Pro Ser Asn Thr Lys
    210                 215                 220
Val Asp Lys Lys Val Glu Pro Lys Ser Cys Asp Lys Thr His Thr Cys
225                 230                 235                 240
Pro Pro Cys Pro Ala Pro Glu Phe Glu Gly Gly Pro Ser Val Phe Leu
                245                 250                 255
```

```
Phe Pro Pro Lys Pro Lys Asp Thr Leu Met Ile Ser Arg Thr Pro Glu
                260                 265                 270

Val Thr Cys Val Val Val Asp Val Ser His Glu Asp Pro Glu Val Lys
            275                 280                 285

Phe Asn Trp Tyr Val Asp Gly Val Glu Val His Asn Ala Lys Thr Lys
        290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Ser Ile Glu Lys Thr Ile Ser Lys
            340                 345                 350

Ala Lys Gly Gln Pro Arg Glu Pro Gln Val Tyr Thr Leu Pro Pro Cys
        355                 360                 365

Arg Asp Glu Leu Thr Lys Asn Gln Val Ser Leu Trp Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Leu His Glu Ala Leu His Ser
        435                 440                 445

His Tyr Thr Gln Lys Ser Leu Ser Leu Ser Pro Gly Lys
450                 455                 460

<210> SEQ ID NO 46
<211> LENGTH: 215
<212> TYPE: PRT
<213> ORGANISM: Artificial Sequence
<220> FEATURE:
<223> OTHER INFORMATION: Synthetic Peptide

<400> SEQUENCE: 46

Ala Ser Glu Leu Thr Gln Asp Pro Ala Val Ser Val Ala Leu Lys Gln
1               5                   10                  15

Thr Val Thr Ile Thr Cys Arg Gly Asp Ser Leu Arg Ser His Tyr Ala
            20                  25                  30

Ser Trp Tyr Gln Lys Lys Thr Gly Gln Ala Pro Lys Leu Leu Phe Tyr
        35                  40                  45

Gly Lys Asn Asn Arg Pro Ser Gly Val Pro Asp Arg Phe Ser Gly Ser
50                  55                  60

Ala Ser Gly Asn Arg Ala Ser Leu Thr Ile Ser Gly Ala Gln Ala Glu
65                  70                  75                  80

Asp Asp Ala Glu Tyr Tyr Cys Ser Ser Arg Asp Lys Ser Gly Ser Arg
                85                  90                  95

Leu Ser Val Phe Gly Gly Gly Thr Lys Leu Thr Val Leu Ser Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
130                 135                 140

Gly Ala Val Thr Val Ala Trp Lys Ala Asp Ser Ser Pro Val Lys Ala
145                 150                 155                 160
```

```
Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 47
<211> LENGTH: 461
<212> TYPE: PRT
<213> ORGANISM: Artificial Sequence
<220> FEATURE:
<223> OTHER INFORMATION: Synthetic Peptide

<400> SEQUENCE: 47

Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asn Phe Asp Asp Ala
            20                  25                  30

Trp Met Thr Trp Val Arg Gln Pro Pro Gly Lys Gly Leu Glu Trp Val
        35                  40                  45

Gly Arg Ile Ser Gly Pro Gly Glu Gly Trp Ser Val Asp Tyr Ala Glu
    50                  55                  60

Ser Val Lys Gly Arg Phe Thr Ile Ser Arg Lys Asn Ser Lys Asn Thr
65                  70                  75                  80

Leu Tyr Leu Glu Met Asn Asn Val Arg Thr Asp Thr Gly Tyr Tyr
                85                  90                  95

Phe Cys Ala Arg Thr Gly Lys His Tyr Asp Phe Trp Ser Gly Tyr Pro
            100                 105                 110

Pro Gly Glu Glu Tyr Phe Gln Asp Trp Gly Gln Gly Thr Lys Val Ile
        115                 120                 125

Val Ser Ser Ala Ser Thr Lys Gly Pro Ser Val Phe Pro Leu Ala Pro
130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Phe Glu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300
```

-continued

```
Pro Arg Glu Glu Gln Tyr Asn Ser Thr Tyr Arg Val Val Ser Val Leu
305                 310                315                 320

Thr Val Leu His Gln Asp Trp Leu Asn Gly Lys Glu Tyr Lys Cys Lys
                325                 330                335

Val Ser Asn Lys Ala Leu Pro Ala Ser Ile Glu Lys Thr Ile Ser Lys
            340                 345                350

Ala Lys Gly Gln Pro Arg Glu Pro Gln Val Tyr Thr Leu Pro Pro Cys
        355                 360                 365

Arg Asp Glu Leu Thr Lys Asn Gln Val Ser Leu Trp Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
            405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Leu His Glu Ala Leu His Ser
        435                 440                 445

His Tyr Thr Gln Lys Ser Leu Ser Leu Ser Pro Gly Lys
    450                 455                 460
```